US006818658B2

(12) United States Patent
Ujjainwalla et al.

(10) Patent No.: US 6,818,658 B2
(45) Date of Patent: Nov. 16, 2004

(54) ACYLATED PIPERIDINE DERIVATIVES AS MELANOCORTIN-4 RECEPTOR AGONISTS

(75) Inventors: Feroze Ujjainwalla, Scotch Plains, NJ (US); Lin Chu, Scotch Plains, NJ (US); Mark T. Goulet, Westfield, NJ (US); Bonnie Louridas, Somerset, NJ (US); Matthew J. Wyvratt, Mountainside, NJ (US); Daniel Warner, Stoneham, MA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/356,879

(22) Filed: Feb. 3, 2003

(65) Prior Publication Data

US 2003/0225060 A1 Dec. 4, 2003

Related U.S. Application Data

(63) Continuation of application No. PCT/US02/05724, filed on Feb. 25, 2002.
(60) Provisional application No. 60/300,118, filed on Jun. 22, 2001, and provisional application No. 60/272,258, filed on Feb. 28, 2001.

(51) Int. Cl.$^7$ ...................... A61K 31/445; C07D 401/06
(52) U.S. Cl. ........................ 514/326; 546/193; 546/208
(58) Field of Search .......................... 514/326; 546/193, 546/208

(56) References Cited

U.S. PATENT DOCUMENTS

| | | |
|---|---|---|
| 5,576,290 A | 11/1996 | Hadley |
| 6,051,555 A | 4/2000 | Hadley |
| 6,166,037 A | 12/2000 | Budhu et al. |
| 6,350,760 B1 | 2/2002 | Bakshi et al. |

FOREIGN PATENT DOCUMENTS

| | | |
|---|---|---|
| WO | WO 99/09984 | 3/1999 |
| WO | WO 99/64002 | 12/1999 |
| WO | WO 00/74649 | 12/2000 |
| WO | WO 01/58891 | 8/2001 |
| WO | WO 01/70337 | 9/2001 |
| WO | WO 01/70708 | 9/2001 |
| WO | WO 01/91752 | 12/2001 |
| WO | WO 02/067869 | 9/2002 |
| WO | WO 02/068387 | 9/2002 |
| WO | WO 03/009847 | 2/2003 |

OTHER PUBLICATIONS

Budhu et al. "preparation of piperidinylpyrrolidins as . . . " CA 130:223167 (1999).*
Getting et al. "MC3–R as a novel target for antiinflammatory therapy" CA133:159566 (2000).*
Uckert et al., Expert Opin. Investig. Drugs (2003), vol. 12(9), pp. 1521–1533, "Current and future trends in the oral pharmacotherapy of male erectile dysfunction".
Corcos et al., Society for Neuroscience, vol. 23 (1997), Abstract 267.9, "HP 228 is a potent agonist of melanocortin receptor 4, and significantly attenuates obesity and diabetes in Zucker fatty rats".
Wessells et al., J. of Urology, vol. 160(2), (1998), pp. 389–393, "Synthetic melanotropic peptide initiates erections in men with psychogenic erectile dysfunction . . . ".
Giraudo et al., Brain Research, vol. 809 (1998), pp. 302–306, "Feeding effects of hypothalamic injection of melanocortin 4 receptor ligands".
Carpino, Exp. Opin. Ther. Patents (2000), vol. 10(6), pp. 819–831, "Patent focus on new anti–obesity agents: Sep. 1999–Feb. 2000".
Chaki et al., Exp. Opin. Ther. Patents (2001), vol. 11(11), pp. 1677–1692, "Recent advances in feeding suppressing agents: Potential therapeutic strategy for the treatment of obesity".
Wessells et al., Urology (2000), vol. 56, pp. 641–646, "Effect of an alpha–melanocyte stimulating hormone analog on penile erection and sexual desire in men with organic erectile dysfunction".
Dorr et al., Life Sciences, vol. 58 (1996), pp. 1777–1784, "Evaluation of melanotan–II, a superpotent cyclic melanotropic peptide in a pilot phase–I clinical study".
Moreland et al., Life Sciences, vol. 62 (1998), pp. 309–318, "Sildenafil, a novel inhibitor of phosphodiesterase type 5 in human corpus cavernosum smooth muscle cells".
Gingell et al., Exp. Opin. Ther. Patents (1999), vol. 9(12), pp. 1689–1696, "Emerging pharamcological therapies for erectile dysfunction".
Dinsmore et al., BMJ, vol. 318 (1999), pp. 387–390, "ABC of sexual health: Erectile dysfunction".
Chen et al., Cell, vol. 91 (1997), pp. 789–798, "Exocrine gland dysfunction in MC5–R–deficient mice . . . ".
Kask et al., Biochem. & Biophys. Res. Comm., vol. 245 (1998), pp. 90–93, "Selective antagonist for the melanocortin 4 receptor (HS014) increases food intake in free–feeding rats".
Huszar et al., Cell, vol. 88 (1997), pp. 131–141, "Targeted disruption of the melanocortin–4 receptor results in obesity in mice".
Pertwee, Exp. Opin. Invest. Drugs, vol. 9(7), (2000), pp. 1553–1571, "Cannabinoid receptor ligands: Clinical and neuropharmacological considerations, relevant to future drug discovery and development".

(List continued on next page.)

*Primary Examiner*—Celia Chang
(74) *Attorney, Agent, or Firm*—Baerbel R. Brown; Catherine D. Fitch; Melvin Winokur

(57) ABSTRACT

Certain novel 4-substituted N-acylated piperidine derivatives are agonists of the human melanocortin receptor(s) and, in particular, are selective agonists of the human melanocortin-4 receptor (MC-4R). They are therefore useful for the treatment, control, or prevention of diseases and disorders responsive to the activation of MC-4R, such as obesity, diabetes, sexual dysfunction, including erectile dysfunction and female sexual dysfunction.

13 Claims, No Drawings

OTHER PUBLICATIONS

Wieland et al., Exp. Opin. Invest. Drugs, vol. 9(6) (2000), pp. 1327–1346, "The role of NPY in metabolic homeostasis: Implications for obesity therapy".

Proietto et al., Exp. Opin. Invest. Drugs, vol. 9(6), (2000), pp. 1317–1326, "Novel anti-obesity drugs".

Olofson et al., J. Org. Chem, vol. 49 (1984), pp. 2081–2082, "A new reagent for the selective, high-yield N-Dealkylation of tertiary amines: Improved syntheses of naltrexone and nalbuphine".

Imai et al., Database STN No. 108:150205, Chem. Pharm. Bull., vol. 35(7), (1987), pp. 2646–2655, "Highly regioselective synthesis of trisubstituted pyrrolidines by 1,3-cycloaddition".

Getting et al., Drug News Perspect, vol. 13(1), (2000), "MC3–R as a novel target for antiinflammatory therapy".

Tomlinson et al., Database STN No. 135:166844 (2001).

Yoram et al., Current Opinion in Urology, vol. 7 (1997), pp. 349–353, "Oral pharmacotherapy in erectile dysfunction".

Peptides: Frontiers of Peptide Science, Fifteenth American Peptide Symposium, Jun. 14–19, 1997 (Nashville, TN).

Heaton et al., Int'l J. of Impotence Research, vol. 9 (1997), pp. 115–121, "A therapeutic taxonomy of treatments for erectile dysfunction: An evolutionary imperative".

Graul, Drug News & Perspectives, vol. 9(9) (1996, pp. 572–575, "Latest findings on the diagnosis and treatment of erectile dysfunction".

* cited by examiner

ACYLATED PIPERIDINE DERIVATIVES AS MELANOCORTIN-4 RECEPTOR AGONISTS

CROSS-REFERENCE TO RELATED APPLICATIONS

This application is a continuation of PCT/US02/05724, filed Feb. 25, 2002, and also claims priority to U.S. provisional applications Ser. Nos. 60/272,258, filed Feb. 28, 2001, and 60/300,118, filed Jun. 22, 2001, both now abandoned, the contents of all of the foregoing of which are hereby incorporated by reference in their entirety.

FIELD OF THE INVENTION

The present invention relates to acylated piperidine derivatives, their synthesis, and their use as melanocortin receptor (MC-R) agonists. More particularly, the compounds of the present invention are selective agonists of the melanocortin-4 receptor (MC-4R) and are thereby useful for the treatment of disorders responsive to the activation of MC-4R, such as obesity, diabetes, male sexual dysfunction, and female sexual dysfunction.

BACKGROUND OF THE INVENTION

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin-4 receptor ligands," *Brain Research*, 80: 302-306 (1998)).

Evidence for the involvement of MC-R's in obesity includes: i) the agouti ($A^{vy}$) mouse which ectopically expresses an antagonist of the MC-1R, MC-3R and -4R is obese, indicating that blocking the action of these three MC-R's can lead to hyperphagia and metabolic disorders; ii) MC-4R knockout mice (D. Huszar et al., *Cell*, 88: 131-141 (1997)) recapitulate the phenotype of the agouti mouse and these mice are obese; iii) the cyclic heptapeptide MT-II (a non-selective MC-1R, -3R, -4R, and -5R agonist) injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R, and -5R and to attenuate food intake and body weight gain over a 12-week period (I. Corcos et al., "HP228 is a potent agonist of melanocortin receptor-4 and significantly attenuates obesity and diabetes in Zucker fatty rats," Society for Neuroscience Abstracts, 23: 673 (1997)).

Five distinct MC-R's have thus far been identified, and these are expressed in different tissues. MC-1R was initially characterized by dominant gain of function mutations at the Extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin-4 receptor (HS014) increases food intake in free-feeding rats," *Biochem. Biophys. Res. Commun.*, 245: 90-93 (1998)). MC-5R is expressed in many tissues, including white fat, placenta and exocrine glands. A low level of expression is also observed in the brain. MC-5R knockout mice reveal reduced sebaceous gland lipid production (Chen et al., *Cell*, 91: 789-798 (1997)).

Erectile dysfunction denotes the medical condition of inability to achieve penile erection sufficient for successful sexual intercourse. The term "impotence" is oftentimes employed to describe this prevalent condition. Approximately 140 million men worldwide, and, according to a National Institutes of Health study, about 30 million American men suffer from impotency or erectile dysfunction. It has been estimated that the latter number could rise to 47 million men by the year 2000. Erectile dysfunction can arise from either organic or psychogenic causes, with about 20% of such cases being purely psychogenic in origin. Erectile dysfunction increases from 40% at age 40, to 67% at age 75, with over 75% occurring in men over the age of 50. In spite of the frequent occurrence of this condition, only a small number of patients have received treatment because existing treatment alternatives, such as injection therapies, penile prosthesis implantation, and vacuum pumps, have been uniformly disagreeable [for a discussion, see "ABC of sexual health—erectile dysfunction," *Brit. Med. J.* 318: 387-390 (1999)]. Only more recently have more viable treatment modalities become available, in particular orally active agents, such as sildenafil citrate, marketed by Pfizer under the brand name of Viagra®. (See "Emerging pharmacological therapies for erectile dysfunction," *Exp. Opin. Ther. Patents* 9: 1689-1696 (1999)). Sildenafil is a selective inhibitor of type V phosphodiesterase (PDE-V), a cyclic-GMP-specific phosphodiesterase isozyme [see R. B. Moreland et al., "Sildenafil: A Novel Inhibitor of Phosphodiesterase Type 5 in Human Corpus Cavernosum Smooth Muscle Cells," *Life Sci.*, 62: 309-318 (1998)]. Prior to the introduction of Viagra on the market, less than 10% of patients suffering from erectile dysfunction received treatment. Sildenafil is also being evaluated in the clinic for the treatment of female sexual dysfunction.

The regulatory approval of Viagra® for the oral treatment of erectile dysfunction has invigorated efforts to discover even more effective methods to treat erectile dysfunction. Several additional selective PDE-V inhibitors are in clinical trials. UK-114542 is a sildenafil backup from Pfizer with supposedly improved properties. Tadalafil or IC-351 (ICOS Corp.) is claimed to have greater selectivity for PDE-V over PDE-VI than sildenafil. Other PDE-V inhibitors include vardenafil from Bayer, M-54033 and M-54018 from Mochida Pharmaceutical Co., and E-4010 from Eisai Co., Ltd.

Other pharmacological approaches to the treatment of erectile dysfunction have been described [see, e.g., "Latest Findings on the Diagnosis and Treatment of Erectile Dysfunction," *Drug News & Perspectives*, 9: 572-575 (1996); "Oral Pharmacotherapy in Erectile Dysfunction," *Current Opinion in Urology*, 7: 349-353 (1997)]. A product under clinical development by Zonagen is an oral formulation of the alpha-adrenoceptor antagonist phentolamine mesylate under the brand name of Vasomax®. Vasomax® is also being evaluated for the treatment of female sexual dysfunction.

Drugs to treat erectile dysfunction act either peripherally or centrally. They are also classified according to whether they "initiate" a sexual response or "facilitate" a sexual response to prior stimulation [for a discussion, see "A Therapeutic Taxonomy of Treatments for Erectile Dysfunction: An Evolutionary Imperative," *Int. J. Impotence Res.*, 9: 115–121 (1997)]. While sildenafil and phentolamine act peripherally and are considered to be "enhancers" or "facilitators" of the sexual response to erotic stimulation, sildenafil appears to be efficacious in both mild organic and psychogenic erectile dysfunction. Sildenafil has an onset of action of 30–60 minutes after an oral dose with the effect lasting about 4 hours, whereas phentolamine requires 5–30 minutes for onset with a duration of 2 hours. Although sildenafil is effective in a majority of patients, it takes a relatively long time for the compound to show the desired effects. The faster-acting phentolamine appears to be less effective and to have a shorter duration of action than sildenafil. Oral sildenafil is effective in about 70% of men who take it, whereas an adequate response with phentolamine is observed in only 35–40% of patients. Both compounds require erotic stimulation for efficacy. Since sildenafil indirectly increases blood flow in the systemic circulation by enhancing the smooth muscle relaxation effects of nitric oxide, it is contraindicated for patients with unstable heart conditions or cardiovascular disease, in particular patients taking nitrates, such as nitroglycerin, to treat angina. Other adverse effects associated with the clinical use of sildenafil include headache, flushing, dyspepsia, and "abnormal vision," the latter the result of inhibition of the type VI phosphodiesterase isozyme (PDE-VI), a cyclic-GMP-specific phosphodiesterase that is concentrated in the retina. "Abnormal vision" is defined as a mild and transient "bluish" tinge to vision, but also an increased sensitivity to light or blurred vision.

Synthetic melanocortin receptor agonists (melanotropic peptides) have been found to initiate erections in men with psychogenic erectile dysfunction [See H. Wessells et al., "Synthetic Melanotropic Peptide Initiates Erections in Men With Psychogenic Erectile Dysfunction: Double-Blind, Placebo Controlled Crossover Study," *J. Urol.*, 160: 389–393 (1998); *Fifteenth American Peptide Symposium*, Jun. 14–19, 1997 (Nashville Tenn.)]. Activation of melanocortin receptors of the brain appears to cause normal stimulation of sexual arousal. In the above study, the. centrally acting α-melanocyte-stimulating hormone analog, melanotan-II (MT-II), exhibited a 75% response rate, similar to results obtained with apomorphine, when injected intramuscularly or subcutaneously to males with psychogenic erectile dysfunction. MT-II is a synthetic cyclic heptapeptide, Ac-Nle-c[Asp-His-DPhe-Arg-Trp-Lys]-$NH_2$, which contains the 4-10 melanocortin receptor binding region common to α-MSH and adrenocorticotropin, but with a lactam bridge. It is a non-selective MC-1R, -3R, -4R, and -5R agonist (Dorr et al., *Life Sciences*, Vol. 58, 1777–1784, 1996). MT-II (also referred to as PT-14) (Erectide®) is presently in clinical development by Palatin Technologies, Inc. and TheraTech, Inc. as a non-penile subcutaneous injection formulation. It is considered to be an "initiator" of the sexual response. The time to onset of erection with this drug is relatively short (10–20 minutes) with a duration of action approximately 2.5 hours. Adverse reactions observed with MT-II include nausea, flushing, loss of appetite, stretching, and yawning and may be the result of activation of MC-1R, MC-2R, MC-3R, and/or MC-5R. MT-II must be administered parenterally, such as by subcutaneous, intravenous, or intramuscular route, since it is not absorbed into the systemic circulation when given by the oral route.

MT-II's erectogenic properties apparently are not limited to cases of psychogenic erectile dysfunction in that men with a variety of organic risk factors developed penile erections upon subcutaneous injection of the compound; moreover, the level of sexual desire was significantly higher after MT-II administration than after placebo [see H. Wessells, "Effect of an Alpha-Melanocyte Stimulating Hormone Analog on Penile Erection and Sexual Desire in Men with Organic Erectile Dysfunction," *Urology*, 56: 641–646 (2000)].

Compositions of melanotropic peptides and methods for the treatment of psychogenic erectile dysfunction are disclosed in U.S. Pat. No. 5,576,290, assigned to Competitive Technologies. Methods of stimulating sexual response in females using melanotropic peptides have been disclosed in U.S. Pat. No. 6,051,555.

Spiropiperidine and piperidine derivatives have been disclosed in WO 99/64002 (Dec. 16, 1999); WO 00/74679 (Dec. 16, 2000); WO 01/70708 (Sep. 27, 2001); WO 01/70337 (Sep. 27, 2001); and WO 01/91752 (Dec. 6, 2001) as agonists of the melanocortin receptor(s) and particularly as selective agonists of the MC-4R receptor and thereby useful for the treatment of diseases and disorders, such as obesity, diabetes, and sexual dysfunction, including erectile dysfunction and female sexual dysfunction.

Because of the unresolved deficiencies of the various pharmacological agents discussed above, there is a continuing need in the medical arts for improved methods and compositions to treat individuals suffering from psychogenic and/or organic sexual dysfunction. Such methods should have wider applicability, enhanced convenience and ease of compliance, short onset of action, reasonably long duration of action, and minimal side effects with few contraindications, as compared to agents now available.

It is therefore an object of the present invention to provide acylated piperidine derivatives which are melanocortin receptor agonists and thereby useful to treat obesity, diabetes, male sexual dysfunction, and female sexual dysfunction.

It is another object of the present invention to provide acylated piperidine derivatives which are selective agonists of the melanocortin-4 (MC-4R) receptor.

It is another object of the present invention to provide pharmaceutical compositions comprising the melanocortin receptor agonists of the present invention with a pharmaceutically acceptable carrier.

It is another object of the present invention to provide methods for the treatment or prevention of disorders, diseases, or conditions responsive to the activation of the melanocortin-4 receptor in a mammal in need thereof by administering the compounds and pharmaceutical compositions of the present invention.

It is another object of the present invention to provide methods for the treatment or prevention of obesity, diabetes mellitus, male sexual dysfunction, and female sexual dysfunction by administering the compounds and pharmaceutical compositions of the present invention to a mammal in need thereof.

It is another object of the present invention to provide methods for the treatment of erectile dysfunction by administering the compounds and pharmaceutical compositions of the present invention to a mammal in need thereof.

These and other objects will become readily apparent from the detailed description that follows.

SUMMARY OF THE INVENTION

The present invention relates to novel 4-substituted N-acylated piperidines of structural formula I:

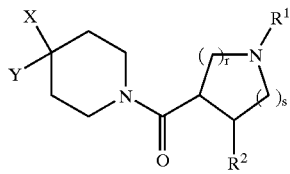

(I)

These acylated piperidine derivatives are effective as melanocortin receptor agonists and are particularly effective as selective melanocortin-4 receptor (MC-4R) agonists. They are therefore useful for the treatment and/or prevention of disorders responsive to the activation of MC-4R, such as obesity, diabetes as well as male and female sexual dysfunction, in particular, male erectile dysfunction.

The present invention also relates to pharmaceutical compositions comprising the compounds of the present invention and a pharmaceutically acceptable carrier.

The present invention also relates to methods for the treatment or prevention of disorders, diseases, or conditions responsive to the activation of the melanocortin-4 receptor in a mammal in need thereof by administering the compounds and pharmaceutical compositions of the present invention.

The present invention also relates to methods for the treatment or prevention of obesity, diabetes mellitus, male sexual dysfunction, and female sexual dysfunction by administering the compounds and pharmaceutical compositions of the present invention.

The present invention also relates to methods for treating erectile dysfunction by administering the compounds and pharmaceutical compositions of the present invention.

The present invention also relates to methods for treating erectile dysfunction by administering the compounds of the present invention in combination with a therapeutically effective amount of another agent known to be useful to treat the condition.

The present invention also relates to methods for treating or preventing obesity by administering the compounds of the present invention in combination with a therapeutically effective amount of another agent known to be useful to prevent or treat the condition.

The present invention also relates to methods for treating or preventing diabetes by administering the compounds of the present invention in combination with a therapeutically effective amount of another agent known to be useful to prevent or treat the condition.

DETAILED DESCRIPTION OF THE INVENTION

The present invention relates to 4-substituted N-acylated piperidine derivatives useful as melanocortin receptor agonists, in particular, as selective MC-4R agonists. Compounds of the present invention are described by structural formula I:

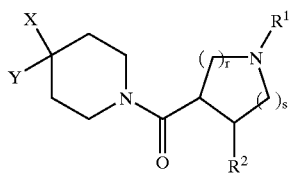

(I)

or a pharmaceutically acceptable salt thereof;
wherein
r is 1 or 2;
s is 0, 1, or 2;
n is 0, 1 or 2;
p is 0, 1, or 2;
$R^1$ is selected from the group consisting of
  hydrogen,
  amidino,
  $C_{1-4}$ alkyliminoyl,
  $C_{1-10}$ alkyl,
  $(CH_2)_n$-$C_{3-7}$ cycloalkyl,
  $(CH_2)_n$-phenyl,
  $(CH_2)_n$-naphthyl, and
  $(CH_2)_n$-heteroaryl wherein heteroaryl is selected from the group consisting of
   (1) pyridinyl,
   (2) furyl,
   (3) thienyl,
   (4) pyrrolyl,
   (5) oxazolyl,
   (6) thiazolyl,
   (7) imidazolyl,
   (8) pyrazolyl,
   (9) isoxazolyl,
   (10) isothiazolyl,
   (11) pyrimidinyl,
   (12) pyrazinyl,
   (13) pyridazinyl,
   (14) quinolyl,
   (15) isoquinolyl,
   (16) benzimidazolyl,
   (17) benzofuryl,
   (18) benzothienyl,
   (19) indolyl,
   (20) benzthiazolyl, and
   (21) benzoxazolyl;
in which phenyl, naphthyl, and heteroaryl are unsubstituted or substituted with one to three groups independently selected from $R^3$; and alkyl and cycloalkyl are unsubstituted or substituted with one to three groups independently selected from $R^3$ and oxo;
$R^2$ is selected from the group consisting of
  phenyl,
  naphthyl, and
  heteroaryl wherein heteroaryl is selected from the group consisting of
   (1) pyridinyl,
   (2) furyl,
   (3) thienyl,
   (4) pyrrolyl,
   (5) oxazolyl,
   (6) thiazolyl,
   (7) imidazolyl,
   (8) pyrazolyl,
   (9) isoxazolyl,

(10) isothiazolyl,
(11) pyrimidinyl,
(12) pyrazinyl,
(13) pyridazinyl,
(14) quinolyl,
(15) isoquinolyl,
(16) benzimidazolyl,
(17) benzofuryl,
(18) benzothienyl,
(19) indolyl,
(20) benzthiazolyl, and
(21) benzoxazolyl;

in which phenyl, naphthyl, and heteroaryl are unsubstituted or substituted with one to three groups independently selected from $R^3$;

each $R^3$ is independently selected from the group consisting of $C_{1-6}$ alkyl,
$(CH_2)_n$-phenyl,
$(CH_2)_n$-naphthyl,
$(CH_2)_n$-heteroaryl,
$(CH_2)_n$-heterocyclyl,
$(CH_2)_n C_{3-7}$ cycloalkyl,
halogen,
$OR^4$,
$(CH_2)_n N(R^4)_2$,
$(CH_2)_n C\equiv N$,
$(CH_2)_n CO_2 R^4$,
$NO_2$,
$(CH_2)_n NR^4 SO_2 R^4$,
$(CH_2)_n SO_2 N(R^4)_2$,
$(CH_2)_n S(O)_p R^4$,
$(CH_2)_n NR^4 C(O)N(R^4)_2$,
$(CH_2)_n C(O)N(R^4)_2$,
$(CH_2)_n NR^4 C(O)R^4$,
$(CH_2)_n NR^4 CO_2 R^4$,
$(CH_2)_n NR^4 C(O)$-heteroaryl,
$(CH_2)_n C(O)NR^4 N(R^4)_2$,
$(CH_2)_n C(O)NR^4 NR^4 C(O)R^4$,
$O(CH_2)_n C(O)N(R^4)_2$,
$CF_3$,
$CH_2 CF_3$,
$OCF_3$, and
$OCH_2 CF_3$;

in which heteroaryl is as defined above; phenyl, naphthyl, heteroaryl, cycloalkyl, and heterocyclyl are unsubstituted or substituted with one to three substituents independently selected from halogen, hydroxy, oxo, $C_{1-4}$ alkyl, trifluoromethyl, and $C_{1-4}$ alkoxy; and wherein any methylene ($CH_2$) carbon atom in $R^3$ is unsubstituted or substituted with one to two groups independently selected from halogen, hydroxy, and $C_{1-4}$ alkyl; or two substituents when on the same methylene ($CH_2$) group are taken together with the carbon atom to which they are attached to form a cyclopropyl group;

each $R^4$ is independently selected from the group consisting of hydrogen,
$C_{1-6}$ alkyl,
$(CH_2)_n$-phenyl,
$(CH_2)_n$-heteroaryl,
$(CH_2)_n$-naphthyl,
$(CH_2)_n$-heterocyclyl,
$(CH_2)_n C_{3-7}$ cycloalkyl, and
$(CH_2)_n C_{3-7}$ bicycloalkyl;

wherein alkyl, phenyl, heteroaryl, heterocyclyl, and cycloalkyl are unsubstituted or substituted with one to three groups independently selected from halogen, $C_{1-4}$ alkyl, hydroxy, and $C_{1-4}$ alkoxy; or two $R^4$ groups together with the atom to which they are attached form a 4- to 8-membered mono- or bicyclic ring system optionally containing an additional heteroatom selected from O, S, and $NC_{1-4}$ alkyl;

each $R^5$ is independently selected from the group consisting of hydrogen,
$C_{1-8}$ alkyl,
$(CH_2)_n$-phenyl,
$(CH_2)_n$-naphthyl,
$(CH_2)_n$-heteroaryl, and
$(CH_2)_n C_{3-7}$ cycloalkyl;

wherein heteroaryl is as defined above; phenyl, naphthyl, and heteroaryl are unsubstituted or substituted with one to three groups independently selected from $R^3$; alkyl and cycloalkyl are unsubstituted or substituted with one to three groups independently selected from $R^3$ and oxo; and wherein any methylene ($CH_2$) in $R^5$ is unsubstituted or substituted with one to two groups independently selected from halogen, hydroxy, and $C_{1-4}$ alkyl; or two $R^5$ groups together with the atom to which they are attached form a 5- to 8-membered mono- or bicyclic ring system optionally containing an additional heteroatom selected from O, S, and $NC_{1-4}$ alkyl;

X is selected from the group consisting of $C_{1-8}$ alkyl,
$(CH_2)_n C_{3-8}$ cycloalkyl,
$(CH_2)_n$-phenyl,
$(CH_2)_n$-naphthyl,
$(CH_2)_n$-heteroaryl,
$(CH_2)_n$heterocyclyl,
$(CH_2)_n C\equiv N$,
$(CH_2)_n CON(R^5 R^5)$,
$(CH_2)_n CO_2 R^5$,
$(CH_2)_n COR^5$,
$(CH_2)_n NR^5 C(O)R^5$,
$(CH_2)_n NR^5 CO_2 R^5$,
$(CH_2)_n NR^5 C(O)N(R^5)_2$,
$(CH_2)_n NR^5 SO_2 R^5$,
$(CH_2)_n S(O)_p R^5$,
$(CH_2)_n SO_2 N(R^5)(R^5)$,
$(CH_2)_n OR^5$,
$(CH_2)_n OC(O)R^5$,
$(CH_2)_n OC(O)OR^5$,
$(CH_2)_n OC(O)N(R^5)_2$,
$(CH_2)_n N(R^5)(R^5)$, and
$(CH_2)_n NR^5 SO_2 N(R^5)(R^5)$;

wherein heteroaryl is as defined above; phenyl, naphthyl, and heteroaryl are unsubstituted or substituted with one to three groups independently selected from $R^3$; alkyl, cycloalkyl, and heterocyclyl are unsubstituted or substituted with one to three groups independently selected from $R^3$ and oxo; and wherein any methylene ($CH_2$) in X is unsubstituted or substituted with one to two groups independently selected from halogen, hydroxy, and $C_{1-4}$ alkyl; and Y is selected from the group consisting of
hydrogen,
$C_{1-8}$ alkyl,
$C_{2-6}$ alkenyl,
$(CH_2)_nC_{3-8}$ cycloalkyl,
$(CH_2)_n$-phenyl,
$(CH_2)_n$-naphthyl,
$(CH_2)_n$-heteroaryl, and
$(CH_2)_n$-heterocyclyl;
wherein heteroaryl is as defined above, and phenyl, naphthyl, and heteroaryl are unsubstituted or substituted with one to three groups independently selected from $R^3$; alkyl, cycloalkyl, and heterocyclyl are optionally substituted with one to three groups independently selected from $R^3$ and oxo; and wherein any methylene ($CH_2$) in Y is unsubstituted or substituted with one to two groups independently selected from halogen, hydroxy, and $C_{1-4}$ alkyl.

In one embodiment of the compounds of structural formula I, $R^1$ is selected from the group consisting of hydrogen, $C_{1-6}$ alkyl, $(CH_2)_{0-1}C_{3-6}$ cycloalkyl, and $(CH_2)_{0-1}$-phenyl; wherein phenyl is unsubstituted or substituted with one to three groups independently selected from $R^3$; and alkyl and cycloalkyl are optionally substituted with one to three groups independently selected from $R^3$ and oxo.

In a second embodiment of the compounds of structural formula I, $R^2$ is phenyl or thienyl optionally substituted with one to three groups independently selected from $R^3$. In a class of this embodiment, $R^2$ is phenyl optionally substituted with one to three groups independently selected from $R^3$.

In a third embodiment of the compounds of structural formula I, X is selected from the group consisting of
$(CH_2)_n$-phenyl,
$(CH_2)_n$-naphthyl,
$(CH_2)_n$-heteroaryl,
$(CH_2)_nC_{3-8}$ cycloalkyl, and
$(CH_2)_n$-heterocyclyl;
wherein heteroaryl is as defined above, and phenyl, naphthyl, and heteroaryl are optionally substituted with one to three groups independently selected from $R^3$; cycloalkyl and heterocyclyl are optionally substituted with one to three groups independently selected from $R^3$ and oxo; and wherein any methylene ($CH_2$) group in X is unsubstituted or substituted with one to two groups independently selected from halogen, hydroxy, and $C_{1-4}$ alkyl. In a class of this embodiment, X is selected from the group consisting of $(CH_2)_{0-1}$-phenyl, $(CH_2)_{0-1}$-heteroaryl, $(CH_2)_{0-1}$-heterocyclyl; wherein phenyl and heteroaryl are optionally substituted with one to three groups independently selected from $R^3$; heterocyclyl is optionally substituted with one to three groups independently selected from $R^3$ and oxo; and $CH_2$ is unsubstituted or substituted with one to two groups independently selected from halogen, hydroxy, and $C_{1-4}$ alkyl. In a subclass of this class, X is phenyl optionally substituted with one to three groups independently selected from $R^3$.

In a fourth embodiment of compounds of formula I, Y is hydrogen.

In yet a further embodiment of compounds of structural formula I, r is 1 or 2 and s is 1.

In yet a further embodiment of the compounds of the present invention, there are provided compounds of structural formula IIa or IIb of the indicated relative stereochemical configurations having the trans orientation of the $R^2$ and piperidinecarbonyl substituents:

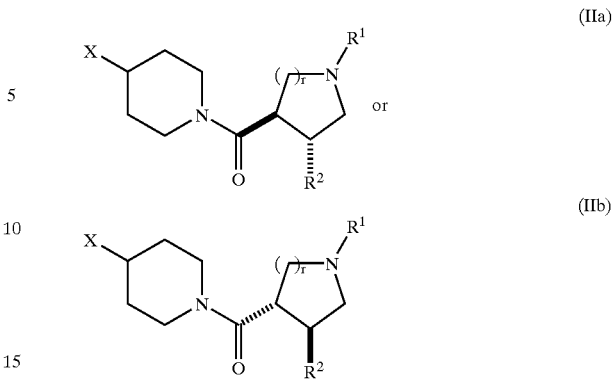

or a pharmaceutically acceptable salt thereof;
wherein
r is 1 or 2;
n is 0, 1, or 2;
p is 0, 1, or 2;
$R^1$ is hydrogen, amidino, $C_{1-4}$ alkyliminoyl, $C_{1-6}$ alkyl, $C_{5-6}$ cycloalkyl, $(CH_2)_{0-1}$ phenyl, $(CH_2)_{0-1}$ heteroaryl; wherein phenyl and heteroaryl are unsubstituted or substituted with one to three groups independently selected from $R^3$, and alkyl and cycloalkyl are unsubstituted or substituted with one to three groups independently selected from $R^3$ and oxo;

$R^2$ is phenyl or thienyl optionally substituted with one to three groups independently selected from $R^3$;

each $R^3$ is independently selected from the group consisting of
$C_{1-6}$ alkyl,
$(CH_2)_n$-heteroaryl,
$(CH_2)_n$-heterocyclyl,
halogen,
$OR^4$,
$(CH_2)_nN(R^4)_2$,
$(CH_2)_nC\equiv N$,
$(CH_2)_nCO_2R^4$,
$(CH_2)_nNR^4SO_2R^4$,
$(CH_2)_nSO_2N(R^4)_2$,
$(CH_2)_nS(O)_pR^4$,
$(CH_2)_nNR^4C(O)N(R^4)_2$,
$(CH_2)_nC(O)N(R^4)_2$,
$(CH_2)_nNR^4C(O)R^4$,
$(CH_2)_nNR^4CO_2R^4$,
$(CH_2)_nNR^4C(O)$-heteroaryl,
$(CH_2)_nC(O)NR^4N(R^4)_2$,
$(CH_2)_nC(O)NR^4NR^4C(O)R^4$,
$O(CH_2)_nC(O)N(R^4)_2$,
$CF_3$,
$CH_2CF_3$,
$OCF_3$, and
$OCH_2CF_3$;
in which heteroaryl is as defined above; phenyl, naphthyl, heteroaryl, cycloalkyl, and heterocyclyl are unsubstituted or substituted with one to three substituents independently selected from halogen, hydroxy, oxo, $C_{1-4}$ alkyl, trifluoromethyl, and $C_{1-4}$ alkoxy; and wherein any methylene ($CH_2$) group in $R^3$ is unsubstituted or substituted with one to two groups independently selected from halogen, hydroxy, and $C_{1-4}$ alkyl; or two substituents when on the same methylene ($CH_2$) group are taken together with the carbon atom to which they are attached to form a cyclopropyl group;

each $R^4$ is independently selected from the group consisting of hydrogen,
$C_{1-8}$ alkyl,
phenyl,
heteroaryl,
$(CH_2)_{0-1}$ heterocyclyl, and
$C_{3-6}$ cycloalkyl;

wherein alkyl, phenyl, heteroaryl, heterocyclyl, and cycloalkyl are unsubstituted or substituted with one to three groups independently selected from halogen, $C_{1-4}$ alkyl, hydroxy, and $C_{1-4}$ alkoxy; or two $R^4$ groups together with the atom to which they are attached form a 4- to 8-membered mono- or bicyclic ring system optionally containing an additional heteroatom selected from O, S, and $NC_{1-4}$ alkyl; and X is phenyl or heteroaryl each of which is optionally substituted with one to three groups independently selected from $R^3$.

In yet a further embodiment of the compounds of the present invention, there are provided compounds of structural formula IIIa or IIIb of the indicated relative stereochemical configurations having the trans orientation of the phenyl and piperidinecarbonyl substituents:

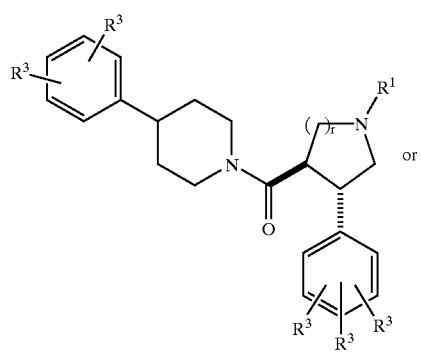

(IIIa)

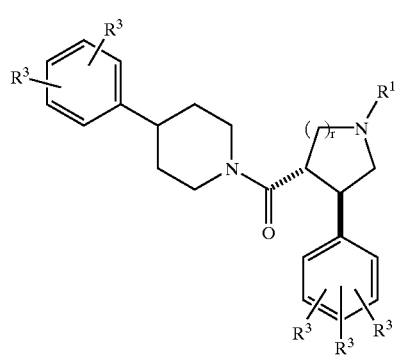

(IIIb)

or a pharmaceutically acceptable salt thereof;
wherein
r is 1 or 2;
$R^1$ is hydrogen, $C_{1-4}$ alkyl, or $(CH_2)_{0-1}$ phenyl;

each $R^3$ is independently selected from the group consisting of $C_{1-6}$ alkyl,
$(CH_2)_{0-1}$-heteroaryl,
$(CH_2)_{0-1}$-heterocyclyl,
halogen,
$OR^4$,
$(CH_2)_{0-1}N(R^4)_2$,
$(CH_2)_{0-1}C\equiv N$,
$(CH_2)_{0-1}CO_2R^4$,
$(CH_2)_{0-1}NR^4SO_2R^4$,
$(CH_2)_{0-1}SO_2N(R^4)_2$,
$(CH_2)_{0-1}S(O)_pR^4$,
$(CH_2)_{0-1}NR^4C(O)N(R^4)_2$,
$(CH_2)_{0-1}C(O)N(R^4)_2$,
$(CH_2)_{0-1}NR^4C(O)R^4$,
$(CH_2)_{0-1}NR^4CO_2R^4$,
$(CH_2)_{0-1}NR^4C(O)$-heteroaryl,
$(CH_2)_{0-1}C(O)NR^4N(R^4)_2$,
$(CH_2)_{0-1}C(O)NR^4NR^4C(O)R^4$,
$O(CH_2)_{0-1}C(O)N(R^4)_2$,
$CF_3$,
$CH_2CF_3$,
$OCF_3$, and
$OCH_2CF_3$;

in which phenyl, naphthyl, heteroaryl, cycloalkyl, and heterocyclyl are unsubstituted or substituted with one to two substituents independently selected from halogen, hydroxy, oxo, $C_{1-4}$ alkyl, trifluoromethyl, and $C_{1-4}$ alkoxy; and wherein any methylene ($CH_2$) group in $R^3$ is unsubstituted or substituted with one to two groups independently selected from halogen, hydroxy, and $C_{1-4}$ alkyl; or two substituents when on the same methylene ($CH_2$) group are taken together with the carbon atom to which they are attached to form a cyclopropyl group; and each $R^4$ is independently selected from the group consisting of hydrogen,
$C_{1-8}$ alkyl,
phenyl,
heteroaryl,
$(CH_2)_{0-1}$ heterocyclyl, and
$C_{3-6}$ cycloalkyl;

wherein alkyl, phenyl, heteroaryl, heterocyclyl, and cycloalkyl are unsubstituted or substituted with one to three groups independently selected from halogen, $C_{1-4}$ alkyl, hydroxy, and $C_{1-4}$ alkoxy; or two $R^4$ groups together with the atom to which they are attached form a 4- to 8-membered mono- or bicyclic ring system optionally containing an additional heteroatom selected from O, S, and $NC_{1-4}$ alkyl.

Illustrative but nonlimiting examples of compounds of the present invention that are useful as melanocortin-4 receptor agonists are the following:

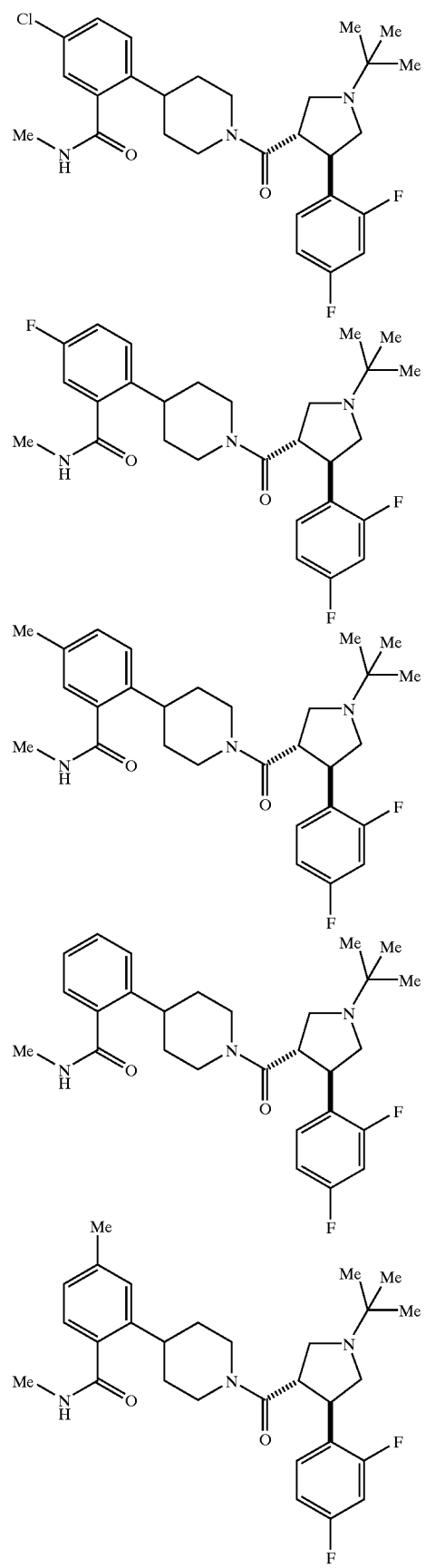
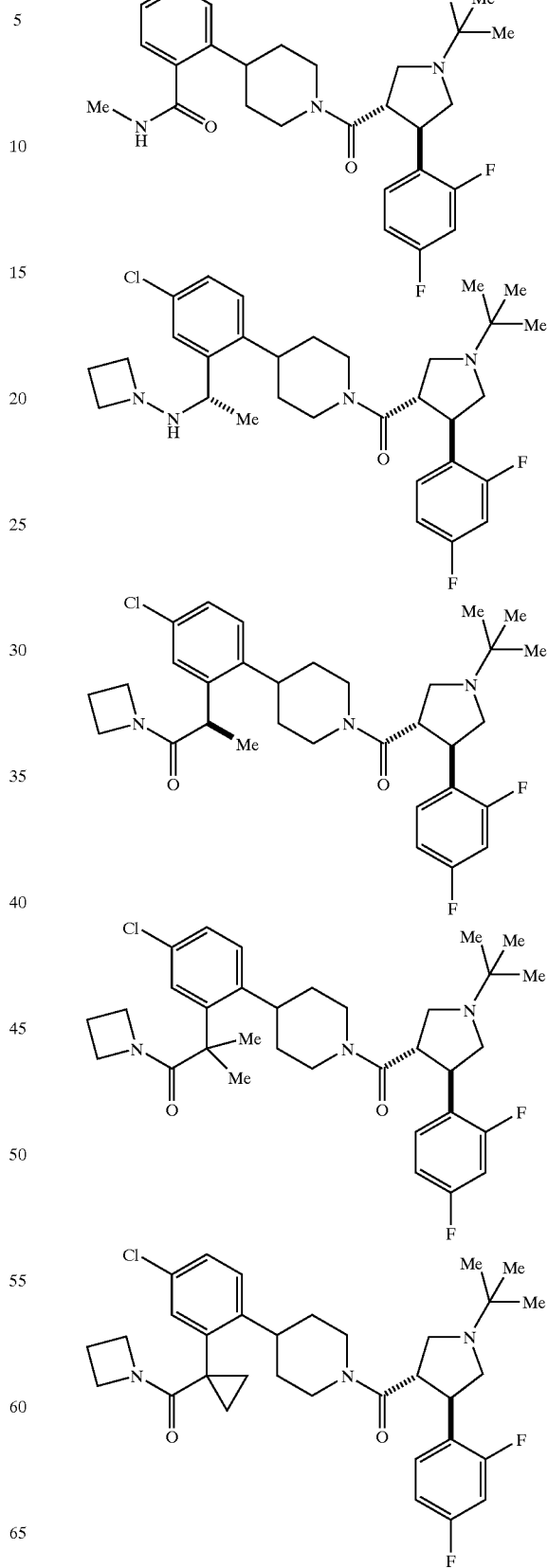

-continued
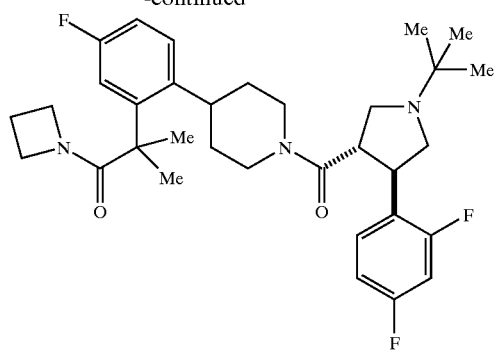
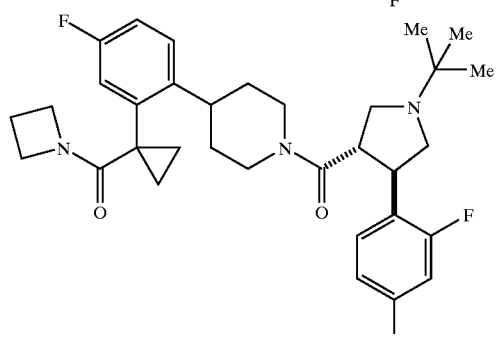
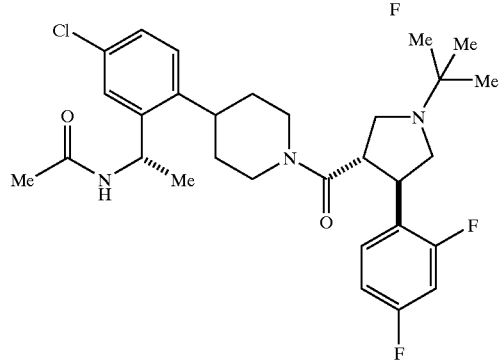
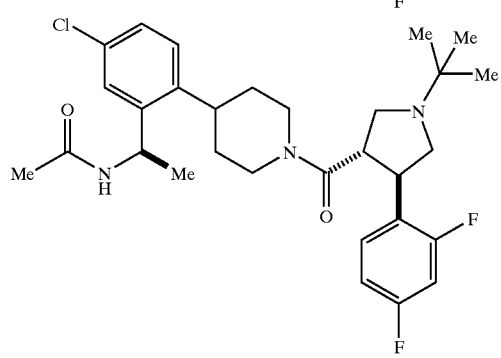
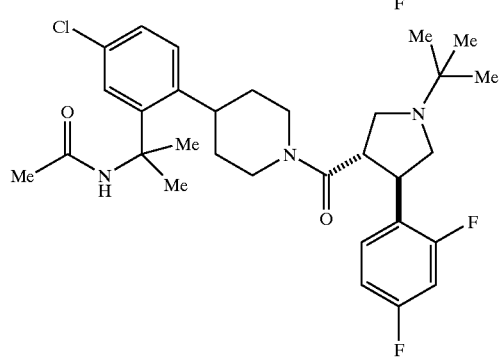
-continued
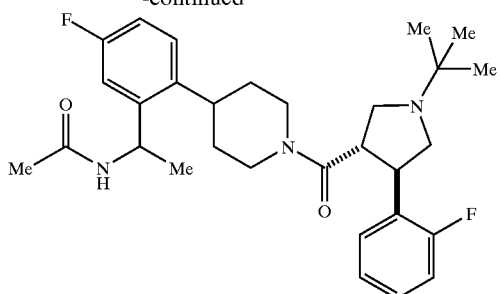
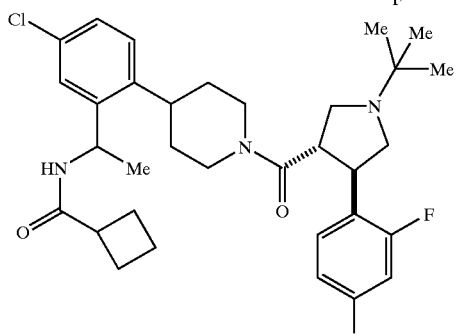
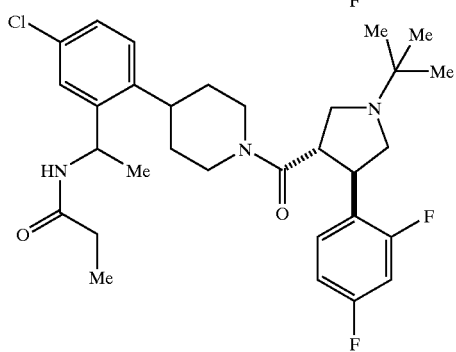
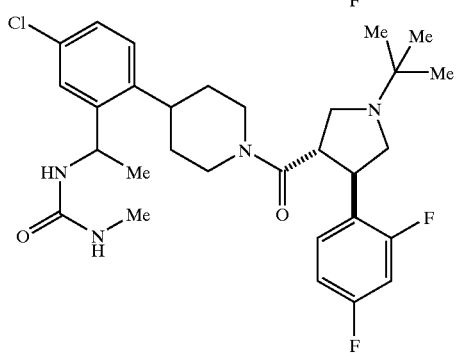
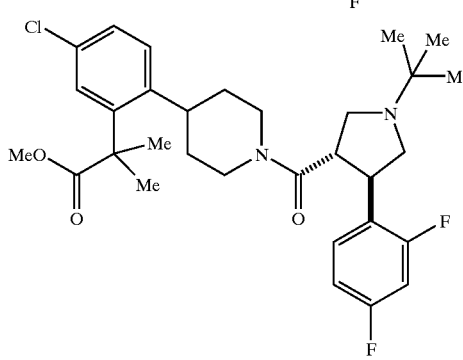

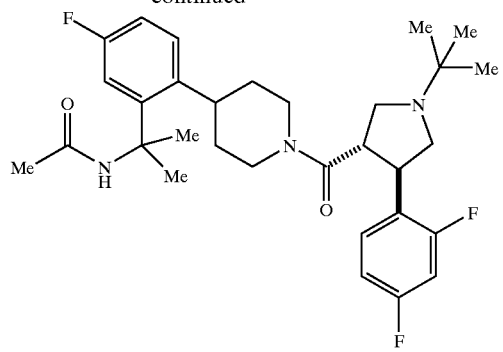
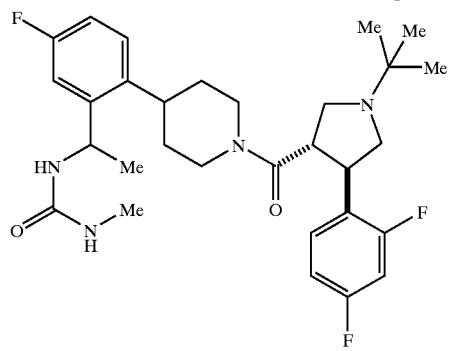
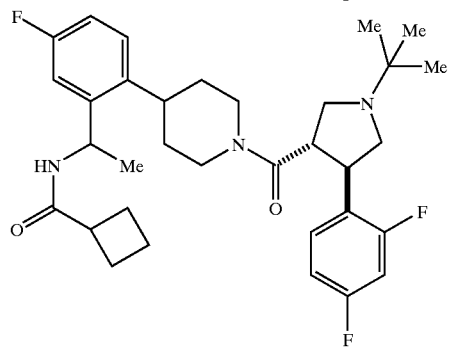
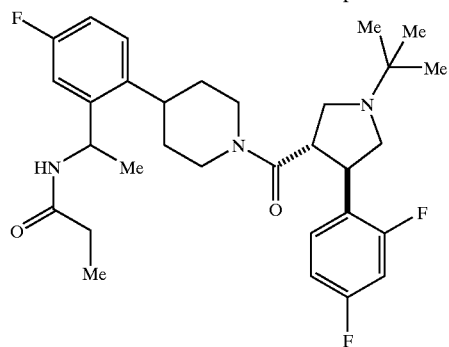
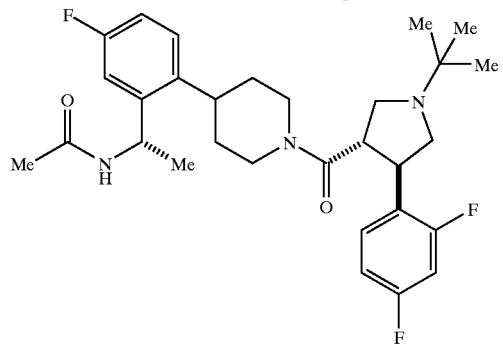
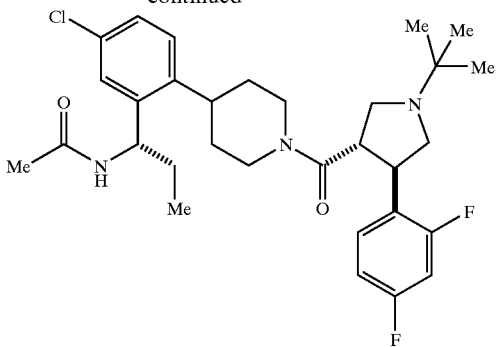
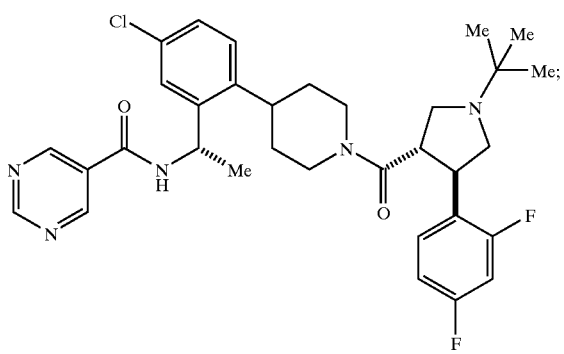
or a pharmaceutically acceptable salt thereof.
Further illustrative of the present invention are the compounds selected from the group consisting of:
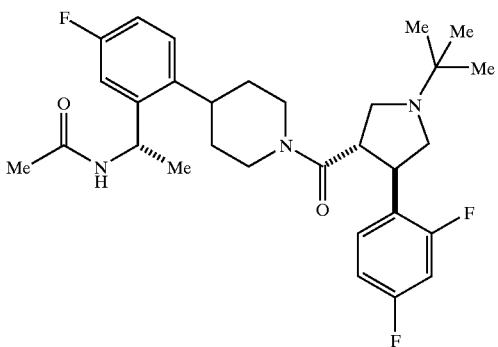
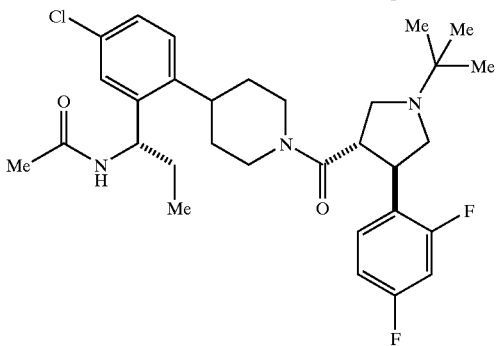

-continued

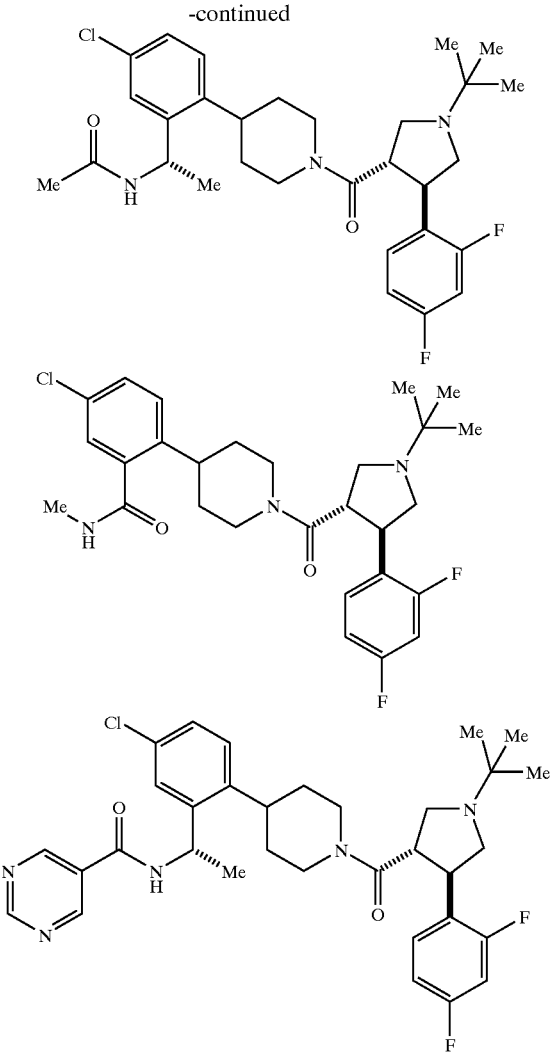

and

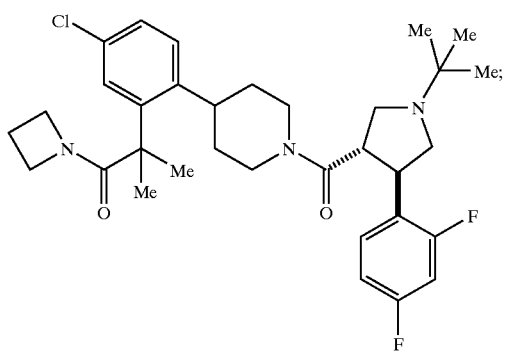

or a pharmaceutically acceptable salt thereof.

The compounds of structural formula I are effective as melanocortin receptor agonists and are particularly effective as selective agonists of MC-4R. They are therefore useful for the treatment and/or prevention of disorders responsive to the activation of MC-4R, such as obesity, diabetes as well as male and/or female sexual dysfunction, in particular, erectile dysfunction, and further in particular, male erectile dysfunction.

Another aspect of the present invention provides a method for the treatment or prevention of obesity or diabetes in a mammal in need thereof which comprises administering to said mammal a therapeutically or prophylactically effective amount of a compound of structural formula I.

Another aspect of the present invention provides a method for the treatment or prevention of male or female sexual dysfunction including erectile dysfunction which comprises administering to a mammal in need of such treatment or prevention a therapeutically or prophylactically effective amount of a compound of structural formula I.

Another aspect of the present invention provides a pharmaceutical composition comprising a compound of structural formula I and a pharmaceutically acceptable carrier.

Yet another aspect of the present invention provides a method for the treatment or prevention of male or female sexual dysfunction including erectile dysfunction which comprises administering to a mammal in need of such treatment or prevention a therapeutically or prophylactically effective amount of a compound of structural formula I in combination with a therapeutically effective amount of another agent known to be useful for the treatment of these conditions.

Yet another aspect of the present invention provides a method for the treatment or prevention of obesity which comprises administering to a mammal in need of such treatment or prevention a therapeutically or prophylactically effective amount of a compound of structural formula I in combination with a therapeutically effective amount of another agent known to be useful for the treatment of this condition.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "halogen" is intended to include the halogen atoms fluorine, chlorine, bromine and iodine.

The term "$C_{1-4}$ alkyliminoyl" means $C_{1-3}C(=NH)-$.

The term "aryl" includes phenyl and naphthyl.

The term "heteroaryl" includes mono- and bicyclic aromatic rings containing from 1 to 4 heteroatoms selected from nitrogen, oxygen and sulfur. "5- or 6-Membered heteroaryl" represents a monocyclic heteroaromatic ring; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

The term "5- or 6-membered carbocyclyl" is intended to include non-aromatic rings containing only carbon atoms such as cyclopentyl and cyclohexyl.

The term "5 and 6-membered heterocyclyl" is intended to include non-aromatic heterocycles containing one to four heteroatoms selected from nitrogen, oxygen and sulfur. Examples of a 5 or 6-membered heterocyclyl include piperidine, morpholine, thiamorpholine, pyrrolidine, imidazolidine, tetrahydrofuran, piperazine, and the like.

Certain of the above defined terms may occur more than once in the above formula and upon such occurrence each term shall be defined independently of the other; thus for example, $NR^4R^4$ may represent $NH_2$, $NHCH_3$, $N(CH_3)CH_2CH_3$, and the like.

An embodiment of the term "mammal in need thereof" is a "human in need thereof," said human being either male or female.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction is often associated with age and is generally caused by a physical disease or as a side-effect of drug treatment.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by another bioactive agent. The "agonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the the present instance, the ability of a compound of structural formula I to bind to a melanocortin receptor. Binding affinities for the compounds of the present invention were measured in the binding assay described below and are expressed as $IC_{50}$'s.

"Efficacy" describes the relative intensity with which agonists vary in the response they produce even when they occupy the same number of receptors and with the same affinity. Efficacy is the property that enables drugs to produce responses. Properties of compounds/drugs can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as EC50's and the "agonist efficacy" for the compounds of the present invention at a particular concentration were measured in the functional assay described below.

Optical Isomers—Diastereomers—Geometric Isomers—Tautomers

Compounds of structural formula I contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed within the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general formula I, IIa, IIb, IIIa, and IIIb may be obtained by stereospecific synthesis using optically pure starting materials or reagents of known absolute configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Formula I are meant to also include the pharmaceutically acceptable salts, such as the hydrochloride salts.

Utility

Compounds of formula I are melanocortin receptor agonists and as such are useful in the treatment, control or prevention of diseases, disorders or conditions responsive to the activation of one or more of the melanocortin receptors including, but are not limited to, MC-1, MC-2, MC-3, MC-4, or MC-5. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immunemodulation, rheumatoid arthritis, skin tanning, acne and other skin disorders, neuroprotective and cognitive and memory enhancement including the treatment of Alzheimer's disease. Some compounds encompassed by formula I show highly selective affinity for the melanocortin-4 receptor (MC-4R) relative to MC-1R, MC-2R, MC-3R, and MC-5R, which makes them especially useful in the prevention and treatment of obesity, as well as male and/or female sexual dysfunction, including erectile dysfunction.

"Male sexual dysfunction" includes impotence, loss of libido, and erectile dysfunction.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders.

"Female sexual dysfunction" can be seen as resulting from multiple components including dysfunction in desire, sexual arousal, sexual receptivity, and orgasm related to disturbances in the clitoris, vagina, periurethral glans, and other trigger points of sexual function. In particular, anatomic and functional modification of such trigger points may diminish the orgasmic potential in breast cancer and gynecologic cancer patients. Treatment of female sexual dysfunction with an MC-4 receptor agonist can result in improved blood flow, improved lubrication, improved sensation, facilitation of reaching orgasm, reduction in the refractory period between orgasms, and improvements in arousal and desire. In a broader sense, "female sexual dysfunction" also incorporates sexual pain, premature labor, and dysmenorrhea.

Administration and Dose Ranges

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally or topically.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of the present invention are administered at a daily dosage of from about 0.001 milligram to about 100 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

For the treatment of sexual dysfunction compounds of the present invention are given in a dose range of 0.001 milligram to about 100 milligram per kilogram of body weight, preferably as a single dose orally or as a nasal spray.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Examples of other active ingredients that may be combined with a compound of Formula I for the treatment or prevention of obesity and/or diabetes, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas, such as tolbutaride and glipizide;

(d) α-glucosidase inhibitors (such as acarbose), (e) cholesterol lowering agents such as (i) HMG-CoA reductase inhibitors (lovastatin, simvastatin, pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption for example beta-sitosterol and (acyl CoA:cholesterol acyltransferase) inhibitors for example melinamide, (v) probucol, (vi) vitamin E, and (vii) thyromimetics;

(f) PPARδ agonists, such as those disclosed in WO97/28149;

(g) anti-obesity serotonergic agents, such as fenfluramine, dexfenfluramine, phentermine, and sibutramine;

(h) β3-adrenoreceptor agonists;

(i) pancreatic lipase inhibitors, such as orlistat;

(j) feeding behavior modifying agents, such as neuropeptide Y1 and Y5 antagonists, such as those disclosed in WO 97/19682, WO 97/20820, WO 97/20821, WO 97/20822, WO 97/20823, WO 01/14376, and U.S. Pat. No. 6,191,160; melanin-concentrating hormone (MCH) receptor antagonists, such as those disclosed in WO 01/21577 and WO 01/21169; and orexin-1 receptor antagonists;

(k) PPARα agonists such as described in WO 97/36579 by Glaxo;

(l) PPARγ antagonists as described in WO97/10813;

(m) serotonin reuptake inhibitors such as fluoxetine, paroxetine, and sertraline;

(n) growth hormone secretagogues, such as MK-0677;

(o) cannabinoid receptor ligands, such as cannabinoid $CB_1$ receptor antagonists or inverse agonists; and (p) protein tyrosine phosphatase-1B (PTP-1B) inhibitors.

Examples of anti-obesity agents that can be employed in combination with a compound of Formula I are disclosed in "Patent focus on new anti-obesity agents," *Exp. Opin. Ther. Patents,* 10: 819–831 (2000); "Novel anti-obesity drugs," *Exp. Opin. Invest. Drugs,* 9: 1317–1326 (2000); and "Recent advances in feeding suppressing agents: potential therapeutic strategy for the treatment of obesity, *Exp. Opin. Ther. Patents,* 11: 1677–1692 (2001). The role of neuropeptide Y in obesity is discussed in *Exp. Opin. Invest. Drugs,* 9: 1327–1346 (2000). Cannabinoid receptor ligands are discussed in *Exp. Opin. Invest. Drugs,* 9: 1553–1571 (2000).

Examples of other active ingredients that may be combined with a compound of Formula I for the treatment or prevention of male or female sexual dysfunction, in particular, male erectile dysfunction, either administered separately or in the same pharmaceutical compositions, include, but are not limited to (a) type V cyclic-GMP-specific phosphodiesterase (PDE-V) inhibitors, including sildenafil and (6R, 12aR)-2,3,6,7,12,12a-hexahydro-2-methyl-6-(3,4-methylenedioxyphenyl)pyrazino[2',1':6,1]pyrido[3,4-b]indole-1,4-dione (IC-351); (b) alpha-adrenergic receptor antagonists, including phentolamine and yohimbine or pharmaceutically acceptable salts thereof; (c) dopamine receptor agonists, such as apomorphine or pharmaceutically acceptable salts thereof; and (d) nitric oxide (NO) donors.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Preparation of Compounds of the Invention

The compounds of structural formula I of the present invention can be prepared according to the procedures of the following Schemes and Examples, using appropriate materials and are further exemplified by the following specific examples. Moreover, by utilizing the procedures described in detail in PCT International Application Publications WO 99/64002 (Dec. 16, 1999) and WO 00/74679 (Dec. 14, 2000), which are incorporated by reference herein in their entirety, in conjunction with the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Abbreviations Used in the Description of the Preparation of the Compounds of the Present Invention:

| | |
|---|---|
| BOC (boc) | t-butyloxycarbonyl |
| BOP | benzotriazol-1-yloxytris(dimethylamino)phosphonium hexafluorophosphate |
| Bu | butyl |
| calc. | calculated |
| CBZ (Cbz) | benzyloxycarbonyl |
| c-hex | cyclohexyl |
| c-pen | cyclopentyl |
| c-pro | cyclopropyl |
| DEAD | diethyl azodicarboxylate |
| DIEA | diisopropylethylamine |
| DMAP | 4-dimethylaminopyridine |
| DMF | N,N-dimethylformamide |
| EDC | 1-(3-dimethylaminopropyl)3-ethylcarbodiimide HCl |
| eq. | equivalent(s) |
| ES-MS | electron spray ion-mass spectroscopy |
| Et | ethyl |
| EtOAc | ethyl acetate |
| HATU | O-(7-azabenzotriazol-1-yl)-1,1,3,3-tetramethyluronium hexafluorophosphate |
| HOAt | 1-hydroxy-7-azabenzotriazole |
| HOBt | 1-hydroxybenzotriazole hydrate |
| HPLC | high performance liquid chromatography |
| LDA | lithium diisopropylamide |
| MC-xR | melanocortin receptor (x being a number) |
| Me | methyl |
| MF | molecular formula |
| MS | mass spectrum |
| Ms | methanesulfonyl |
| OTf | trifluoromethanesulfonyl |
| Ph | phenyl |
| Phe | phenylalanine |
| Pr | propyl |
| prep. | prepared |
| PyBrop | bromo-tris-pyrrolidino-phosphonium hexafluorophosphate |
| r.t. | room temperature |
| TFA | trifluoroacetic acid |
| THF | tetrahydrofuran |
| TLC | thin-layer chromatography. |

Reaction Schemes A–L illustrate the methods employed in the synthesis of the compounds of the present invention of structural formula I. All substituents are as defined above unless indicated otherwise.

Reaction Scheme A illustrates a key step in the synthesis of the novel compounds of structural formula I of the present invention. As shown in reaction Scheme A, the reaction of a 4-substituted piperidine or 4-substituted tetrahydropyridine of type 1 with a carboxylic acid derivative of formula 2 affords a title compound of structural formula I. The amide bond coupling reaction illustrated in reaction Scheme A is conducted in an appropriate inert solvent such as dimethylformamide (DMF), methylene chloride or the like and may be performed with a variety of reagents suitable for amide coupling reactions such as O-(7-azabenzotriazol-1-yl)-1,1,3,3-tetramethyluronium hexafluorophosphate (HATU), 1-(3-dimethylaminopropyl)-3-ethylcarboduimide hydrochloride (EDC) or benzotriazol-1-yloxytripyrrolidinephosphonium hexafluorophosphate (PyBOP). Preferred conditions for the amide bond coupling reaction shown in reaction Scheme A are known to those skilled in organic synthesis. Such modifications may include, but are not limited to, the use of basic reagents such as triethylamine (TEA) or N-methylmorpholine (NMM), or the addition of an additive such as 1-hydroxy-7-azabenzotriazole (HOAt) or 1-hydroxybenzotriazole (HOBt). Alternatively, 4-substituted piperidines or 4-substituted tetrahydropyridines of formula 1 may be treated with an active ester or acid chloride derived from carboxylic acid 2 which also affords compounds of structural formula I. The amide bond coupling shown in reaction Scheme A is usually conducted at temperatures between 0° C. and room temperature, occasionally at elevated temperatures, and the coupling reaction is typically conducted for periods of 1 to 24 hours.

When 1 is a 4-substituted tetrahydropyridine, the amide coupling product can be reduced to form the corresponding piperidine derivative (I) by hydrogenation in a solvent such as ethanol, ethyl acetate, acetic acid or mixtures thereof using a noble metal catalyst on carbon such as platinum (IV) oxide, palladium-on-carbon, or palladium hydroxide.

If it is desired to produce a compound of structural formula I wherein $R^1$ is a hydrogen, the N-BOC protected analogs of structural formula I may be used in the synthesis and deprotected under acidic conditions, for instance using trifluoroacetic acid in a solvent like methylene chloride or hydrogen chloride in a solvent such as ethyl acetate at room temperature.

When it is desired to prepare compounds of structural formula I wherein $R^1$ is not a hydrogen, the compounds of general formula I ($R^1$=H) may be further modified using the methodology described below in reaction Scheme M.

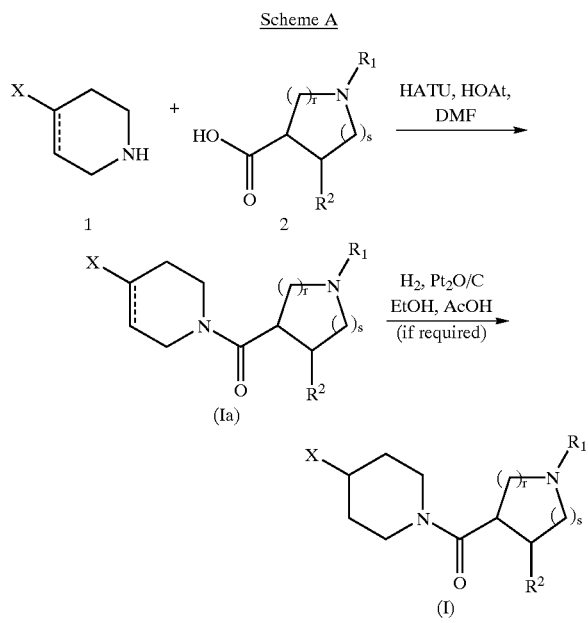

Reaction Schemes B-I illustrate methods for the synthesis of the carboxylic acids of general formula 2 that are utilized in the amide bond coupling reaction shown in reaction Scheme A. Reaction Schemes J-L illustrate additional methods for the synthesis of 4-substituted piperidines of general formula 1 that are used in that same step.

Reaction Scheme B illustrates a preferred method for the synthesis of compounds of general formula 2 wherein r is 2 and s is 1 such that the resulting heterocycle is a 3-aryl-4-piperidine carboxylic acid derivative 10. The synthesis of 10 begins with a commercially available β-keto ester such as 3. Generally a protecting group interchange of an N-BOC group for the N-benzyl group is performed initially. Thus a β-keto ester of formula 3 is subjected to debenzylation by hydrogenolysis using a palladium-on-carbon catalyst in a solvent system such as 1:1 ethanol-water under a hydrogen atmosphere. The resulting piperidone 4 is then protected as its tert-butyl carbamate using BOC anhydride in the presence of a base and a suitable solvent. For example, this can be accomplished in a two phase mixture of chloroform and aqueous sodium bicarbonate as shown. Incorporation of the 3-aryl substituent is then performed in two steps. First, the β-keto ester group is converted to the corresponding vinyl triflate 6 using trifluoromethanesulfonic anhydride and an organic base like N,N-diisopropylethylamine in an aprotic solvent such as methylene chloride. The resulting vinyl triflate 6 is then subjected to a palladium-catalyzed cross-coupling reaction with an aryl boronic acid (7) using a palladium (II) catalyst such as [1,1'-bis(diphenylphosphino)-ferrocene]dichloropalladium(II). Preferred conditions for this reaction are the use of a toluene-ethanol-aqueous sodium carbonate solvent system at an elevated temperature, for instance 50–100° C., for a period of 2–24 hours. The resulting aryl-substituted tetrahydropyridine derivative 8 can be reduced to a piperidine such as 9 using a variety of known techniques and the method chosen will determine the stereochemical outcome of the product. For instance, hydrogenation of 8 with a palladium on carbon catalyst in a solvent such as ethanol affords cis-3,4-disubstituted piperidines of general formula 9. Alternatively, a dissolving metal reduction using a metal, such as magnesium in methanol, reduces the double bond of 8 and produces a mixture of both cis and trans 3,4-disubstituted piperidines of formula 9. The resulting mixture of cis and trans diastereoisomers may be separated chromatographically or it may be subsequently epimerized to afford the pure trans isomer of 9 by treating the mixture with a base like sodium methoxide in methanol. Finally, hydrolysis of either the cis or trans 3-aryl-4-piperidine carboxylic ester 9 affords either a cis or trans 3-aryl-4-piperidine carboxylic acid of general formula 10, corresponding to an acid of general formula 2 wherein r is 2 and s is 1. The cis or trans carboxylic acids of general formula 10 are produced as racemates and either may be resolved to afford enantiomerically pure compounds by methods known in organic synthesis. Preferred methods include resolution by crystallization of diastereoisomeric salts derived from acids 10 and a chiral amine base or the use of chiral stationary phase liquid chromatography columns.

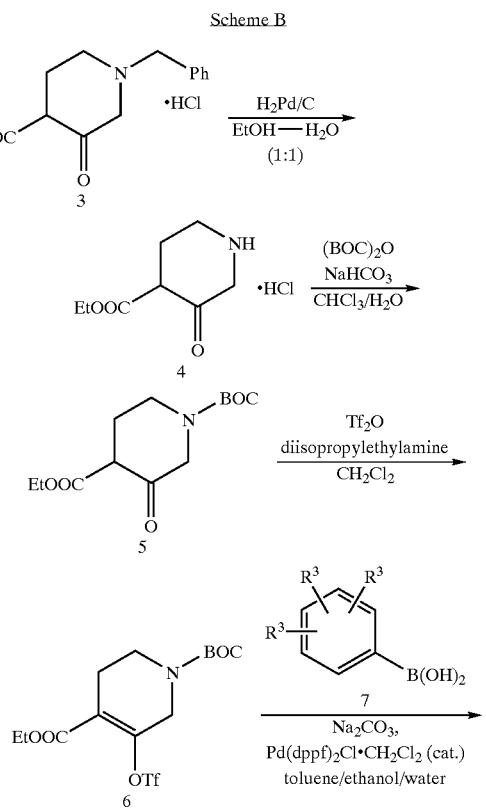

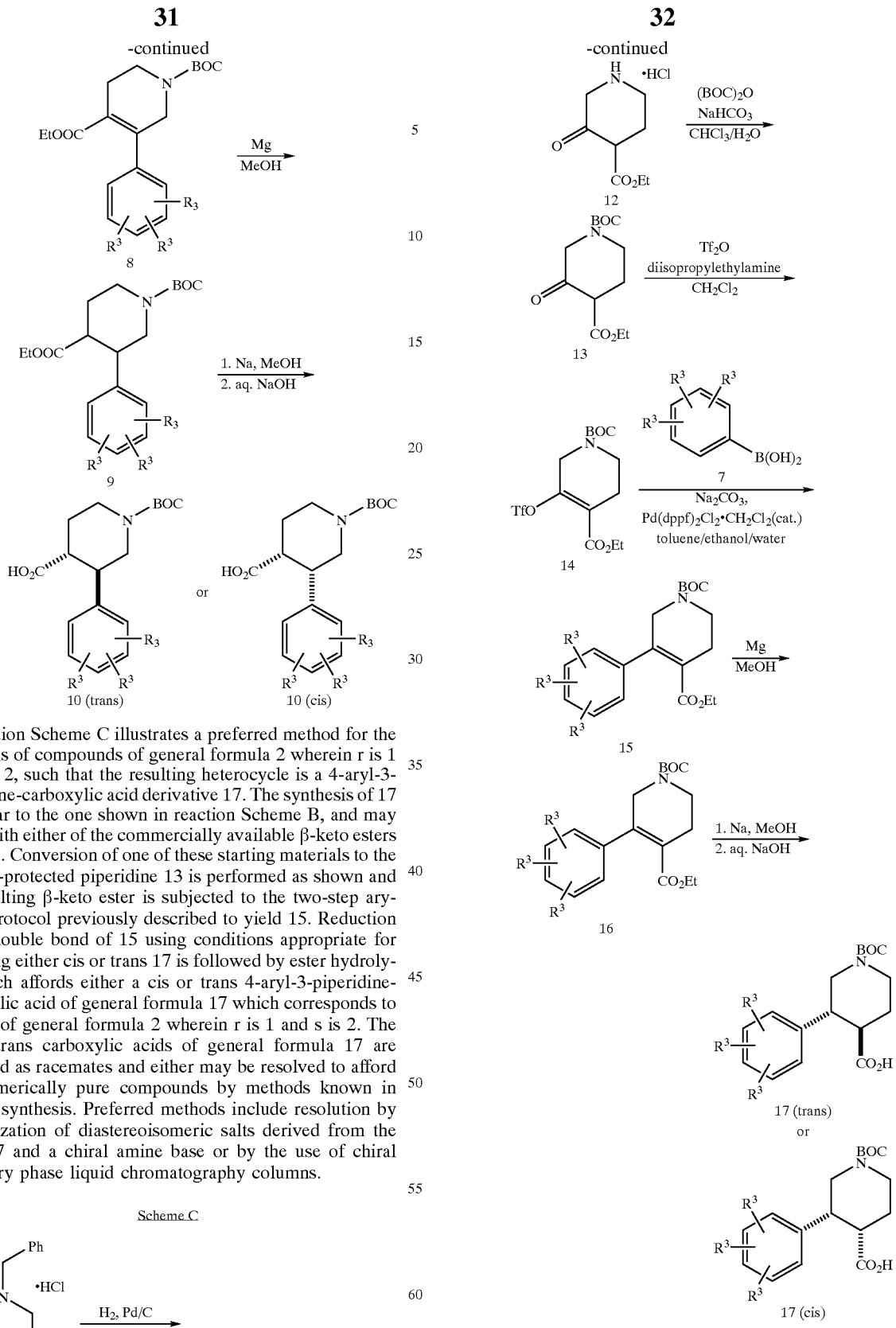

Reaction Scheme C illustrates a preferred method for the synthesis of compounds of general formula 2 wherein r is 1 and s is 2, such that the resulting heterocycle is a 4-aryl-3-piperidine-carboxylic acid derivative 17. The synthesis of 17 is similar to the one shown in reaction Scheme B, and may begin with either of the commercially available β-keto esters 11 or 12. Conversion of one of these starting materials to the N-BOC-protected piperidine 13 is performed as shown and the resulting β-keto ester is subjected to the two-step arylation protocol previously described to yield 15. Reduction of the double bond of 15 using conditions appropriate for obtaining either cis or trans 17 is followed by ester hydrolysis which affords either a cis or trans 4-aryl-3-piperidine-carboxylic acid of general formula 17 which corresponds to an acid of general formula 2 wherein r is 1 and s is 2. The cis or trans carboxylic acids of general formula 17 are produced as racemates and either may be resolved to afford enantiomerically pure compounds by methods known in organic synthesis. Preferred methods include resolution by crystallization of diastereoisomeric salts derived from the acids 17 and a chiral amine base or by the use of chiral stationary phase liquid chromatography columns.

Scheme C

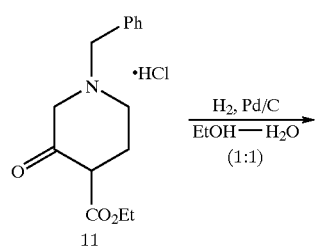

The synthesis of the N-BOC protected carboxylic acids of general formula 10 and 17 illustrated in reaction Schemes B and C are useful for the preparation of title compounds of structural formula I bearing a variety of $R^1$ substituents as noted above. For the synthesis of certain title compounds of structural formula I, for instance when it is desired that $R^1$ be a tert-butyl group, it is preferable to incorporate that $R^1$ substituent at an earlier stage of the synthesis. The synthesis of a 1-substituted-3-ketopiperidine-4-carboxylic ester (21) is shown in reaction Scheme D. A primary amine 18 bearing a desired $R^1$ substituent like a tert-butyl group is reacted with ethyl 4-bromobutyrate at elevated temperature in the absence of a solvent to afford the N-substituted ethyl 4-aminobutyrate 19. The amino ester 19 is then alkylated a second time with ethyl bromoacetate in a high boiling inert solvent such as toluene and in the presence of a base such as powdered potassium carbonate. The resulting aminodiesters of general formula 20 are then cyclized using an intramolecular Dieckmann reaction to afford piperidines such as 21. The Dieckmann reaction is performed using a strong base such as potassium tert-butoxide or the like, in an aprotic solvent such as THF at temperatures between room temperature and the boiling point of the solvent. The resulting 1-substituted-3-ketopiperidine-4-carboxylic ester 21 corresponds to a compound of general formula 5 shown in reaction Scheme B, where the BOC group is replaced with the desired $R^1$ substituent. The compounds of general formula 21 may then be converted to compounds of general formula 2 where the $R^1$ substituent replaces the BOC group using the reaction sequence illustrated in reaction Scheme B.

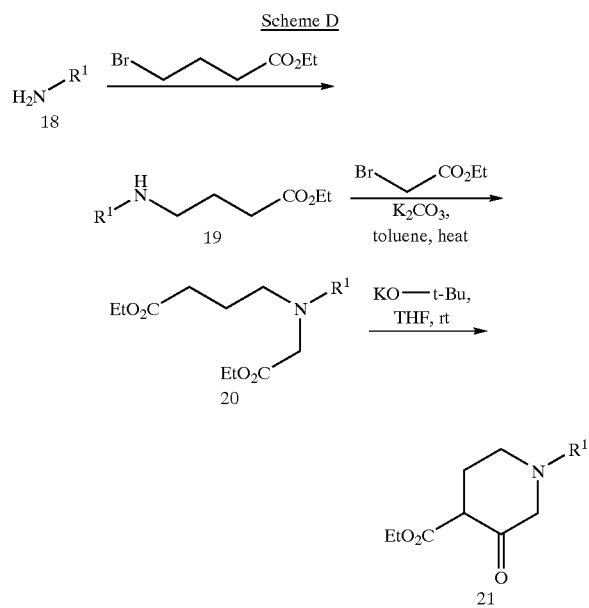

When it is desirable to synthesize a compound of general formula 17 wherein the BOC group is replaced with a substituent group $R^1$, a reaction sequence similar to the one illustrated in reaction Scheme C may be employed as shown in reaction Scheme E. An amine 18 bearing the desired $R^1$ substituent is first subjected to a Michael addition with excess ethyl acrylate in the presence of a solvent such as THF or ethanol. The resulting diester 22 is then converted to a 1-substituted-4-ketopiperidine-3-carboxylic ester 23 using an intramolecular Dieckmann reaction under conditions similar to those illustrated in reaction Scheme C. The substituted piperidine 23 corresponds to a compound of general formula 13 shown in reaction Scheme C, wherein the BOC group is replaced with the desired $R^1$ substituent. The compounds of general formula 23 may then be converted to compounds of general formula 2 where the $R^1$ substituent replaces the BOC group using the methodology illustrated in reaction Scheme C.

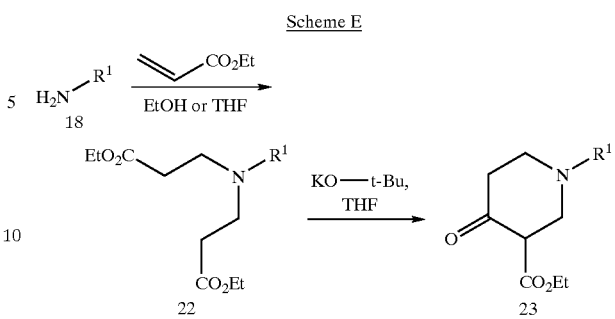

Reaction Scheme F illustrates a strategy for the synthesis of compounds of general formula 2 when the values of r and s are selected such that the resulting heterocycle is a 3-aryl-4-pyrrolidine carboxylic acid derivative (29). The preferred method for the synthesis of compounds of general formula 29 involves the azomethine ylid 3+2 cycloaddition reaction of an azomethine ylid precursor of general formula 25 and a substituted cinnamic ester 24. The azomethine cycloaddition reaction of 24 and 25 affords the 3,4-disubstituted pyrrolidine 26, and the stereochemical relationship of the substituents on the newly formed pyrrolidine ring is determined by the stereochemistry of the double bond in the cinnamate ester 24. Thus the trans ester 24 affords a trans 3,4-disubstituted pyrrolidine of formula 26 as shown. The corresponding cis cinnamate ester affords a cis 3,4-disubstituted pyrrolidine of general formula 26. Cis or trans 3-arylpyrrolidine-4-carboxylic esters of general formula 26 may be resolved to afford enantiomerically pure compounds using a method such as resolution by crystallization of the diastereoisomeric salts derived from 26 and a chiral carboxylic acid, or directly by the use of chiral stationary phase liquid chromatography columns. Reaction Scheme F illustrates the case where a trans cinnamic ester 24 is converted to a trans 3,4-disubstituted pyrrolidine 26 and its subsequent resolution affords the enantiomerically pure trans pyrrolidine esters 27 and 28. Finally, the esters of general formula 26 (or their pure enantiomers 27 and 28) are hydrolyzed to the corresponding amino acid hydrochlorides of general formula 29 as shown at the bottom of reaction Scheme F.

Amino acids of general formula 29 are zwitterionic. Therefore it is in some cases difficult to achieve efficient separation and purification of these compounds from aqueous reactions or workups. In these cases it is preferred to effect the hydrolysis using a reagent such potassium trimethylsilanolate in diethyl ether. Under these conditions the potassium salt of the carboxylic acid is produced which affords an easily isolated precipitate in ether. The resulting salt is then converted to the corresponding amino acid hydrochloride by treatment with excess hydrogen chloride in a suitable solvent such as ethyl acetate. Alternatively, esters such as 26 may be converted directly to the amino acid hydrochlorides 29 under acidic hydrolysis conditions. The hydrolysis of the ester 26 is achieved by prolonged reaction with concentrated hydrochloric acid at an elevated temperature. For example, this reaction may be conducted in 8 M hydrochloric acid at reflux overnight. The reaction mixture is then cooled and evaporated in vacuo to afford the amino acid hydrochloride 29. The amino acid hydrochlorides of general formula 29 correspond to an amino acid hydrochloride of general formula 2 wherein both r and s are 1 and may be employed directly in the amide bond coupling step illustrated in reaction Scheme A to produce the compounds of the present invention of structural formula I.

Scheme F

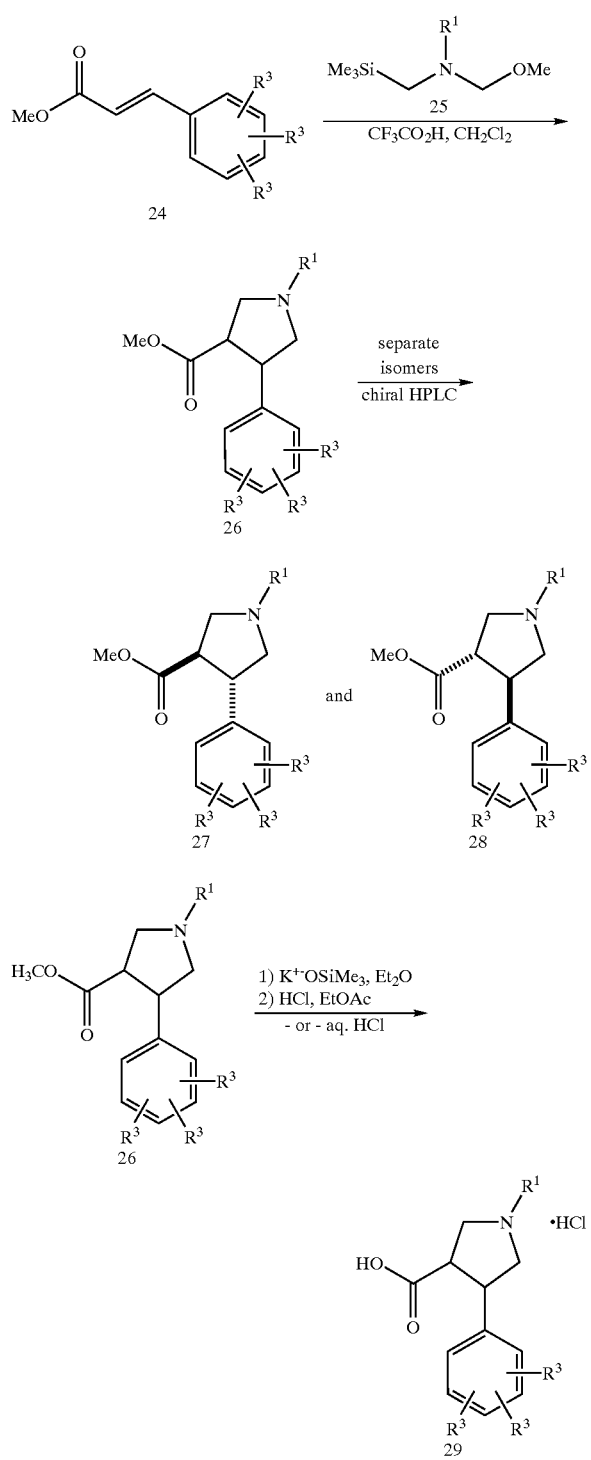

Typically acids of general formula 29 are reacted with an acid chloride such as pivaloyl chloride in the presence of a base such as triethylamine and in a suitable aprotic solvent such as THF. The intermediate cinnamyl-pivaloyl anhydride is converted to the product 31 by reaction with the oxazolidinone 30 in the presence of lithium chloride, an amine base such as triethylamine and in a solvent such as THF, and the reaction is conducted at temperatures between −20° C. and room temperature for periods of 1–24 hours. Alternatively, the oxazolidinone 30 may be deprotonated with a strong base such as n-butyllithium in THF at low temperatures such as −78° C. and then reacted with a mixed anhydride obtained from acid 29 and an acid chloride like pivaloyl chloride as noted above. The cinnamyl oxazolidinone of general formula 31, which is produced by either of these methods, is then reacted with the azomethine ylid precursor 25 in a manner similar to that described in reaction Scheme F, and the products of the reaction are the substituted pyrrolidines of general formulas 33 and 34 as shown. The products 33 and 34 are diastereoisomers of each other and may therefore be separated by standard methods such as recrystallization or by liquid chromatography on a solid support such as silica gel. As discussed above, if the trans isomer of the cinnamic acid of general formula 29 is employed in the first step of reaction Scheme G, then a trans isomer of the substituted cinnamyl oxazolidinone 31 is produced. If such a trans cinnamyl oxazolidinone is then subjected to the azomethine ylid cycloaddition with an azomethine ylid precursor of formula 25, the products are the diastereoisomeric trans- disubstituted pyrrolidines related to 33 and 34.

Scheme G

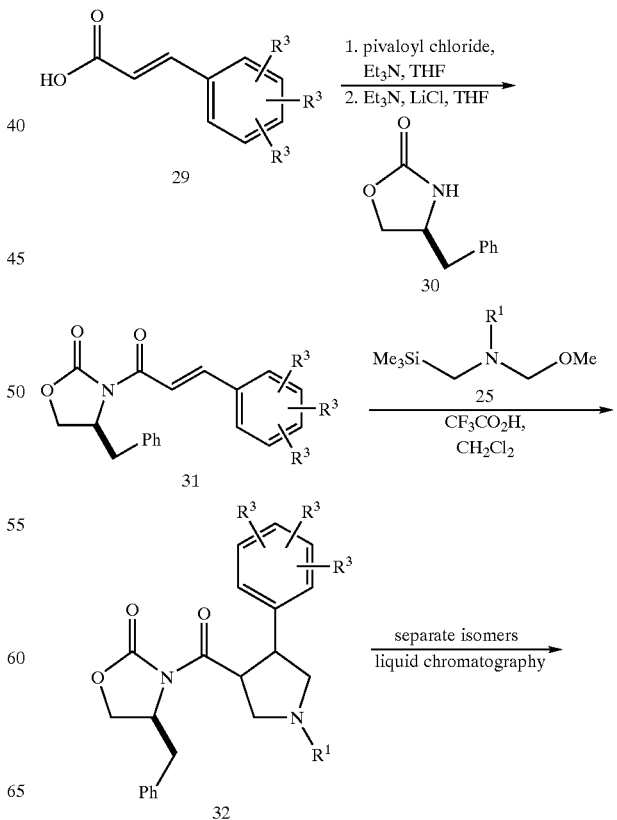

Another preferred method for the synthesis of enantiomerically pure 3-arylpyrrolidine-4-carboxylic acid derivatives is illustrated in reaction Scheme G. In this synthetic method, a substituted cinnamic acid of general formula 29 is first derivatized with a chiral auxilliary such as (S)-(−)-4-benzyl-2-oxazolidinone (30). The acylation of chiral auxiliary 30 with cinnamic acids of formula 29 is performed by initial activation of the acid to afford a mixed anhydride.

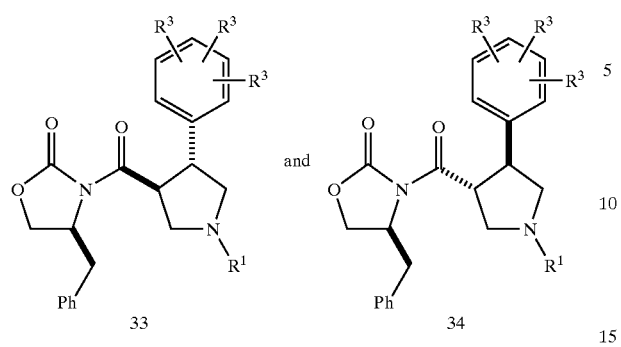

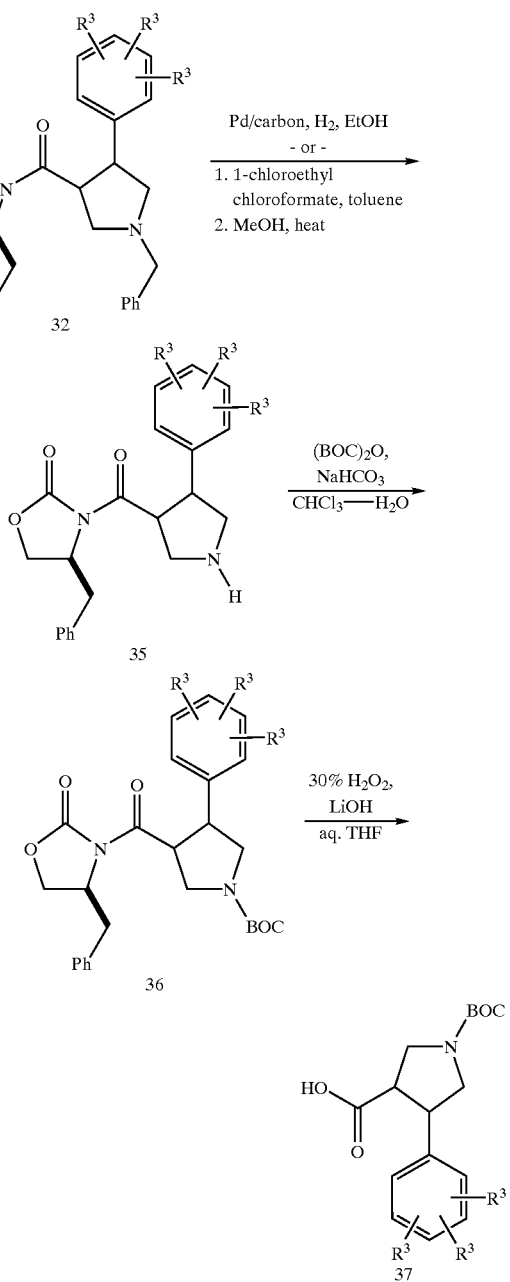

Scheme H

The azomethine ylid cycloaddition reactions shown in reaction Schemes F and G are generally conducted with the commercially available azomethine ylid precursor N-(methoxymethyl)-N-(trimethylsilylmethyl)-benzylamine (25, $R^1$=—$CH_2Ph$). When the $R^1$ substituent in the title compounds of structural formula I is chosen to be a group other than benzyl, it is generally preferable to remove the benzyl group from the substituted pyrrolidine compound at this point, and replace it with a more readily removed protecting group such as an N-BOC group. Reaction Scheme H illustrates this process with a generalized 3,4-disubstituted pyrrolidine of formula 32. The preferred method for removal of the N-benzyl group from compounds of general formula 32 will depend upon the identity of the $R^3$ substituents. If these substituents are unaffected by hydrogenation conditions, then the N-benzyl group may be removed by hydrogenolysis using a palladium on carbon catalyst in a solvent such as ethanol and in the presence of hydrogen gas or a hydrogen donor such as formic acid. Occasionally it may be preferred that one of the substituents $R^3$ be a halogen or another substituent defined above which would be reactive under hydrogenation conditions. In these cases, the compound of general formula 32 is reacted with 1-chloroethyl chloroformate in an inert solvent such as toluene at temperatures between room temperature and 110° C. (Olafson, R. A. et al. *J. Org. Chem.* 1984, 49, 2081). The toluene is then removed, and the residue is heated in methanol for a period of 15–60 minutes, and the product is the debenzylated pyrrolidine of general formula 35. The resulting pyrrolidine 35 is then protected as its tert-butyl carbamate (36) using BOC anhydride in the presence of a base and a suitable solvent. For example, this can be accomplished in a two phase mixture of chloroform and aqueous sodium bicarbonate as shown in reaction Scheme H.

The oxazolidinone chiral auxilliary is next hydrolyzed from the pyrrolidines of general formula 36 as shown at the bottom of reaction Scheme H. The hydrolysis reaction is accomplished using lithium hydroperoxide generated in situ from lithium hydroxide and 30% aqueous hydrogen peroxide. The reaction is typically conducted in a solvent system such as aqueous THF, and the reaction is performed at temperatures between 0° C. and room temperature for a period of 1–6 hours. The resulting carboxylic acids of general formula 37 correspond to carboxylic acids of general formula 2 where both r and s are 1. Using the methodology presented in reaction Scheme A, the compounds of general formula 37 may then be converted to the compounds of the present invention of structural formula I.

As noted previously in the discussion of reaction Scheme D, it may occasionally be preferable to incorporate the $R^1$ substituent into the substituted pyrrolidine of general formula 37 at an earlier stage of the synthesis, for instance when it is desired that $R^1$ be a tert-butyl group. In such cases, it is possible to utilize an azomethine ylid precursor (25) bearing the desired $R^1$ substituent in the cycloaddition reactions illustrated in reaction Schemes F and G. Reaction Scheme I illustrates the preparation of azomethine precursors of formula 25 starting with amines of general formula 18. Reaction of the amine of formula 18 with chloromethyltrimethylsilane at high temperature and in the absence of solvent affords the N-trimethylsilylmethyl-substituted amine of general formula 38. Subsequent reaction of 38 with aqueous formaldehyde in the presence of methanol and a base such as potassium carbonate then affords the generalized ylid precursor 25 which can be utilized in the cycloaddition reactions discussed above.

Scheme I

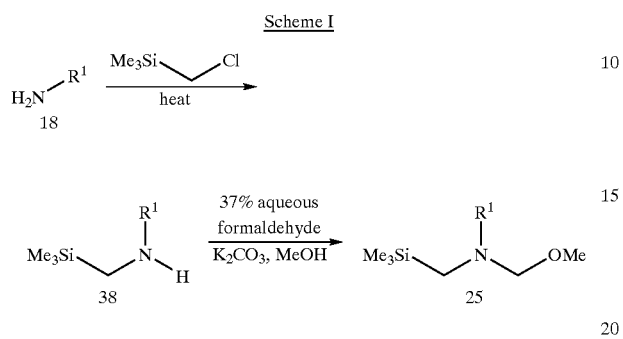

Reaction Schemes J–L illustrate additional methods for the synthesis of the 4-substituted piperidines of general formula 1 which are required in the amide bond coupling step illustrated in reaction Scheme A. As shown in Reaction Scheme J, treatment of enoltriflate 39 (prepared as described in: Rohr, M.; Chayer, S.; Garrido, F.; Mann, A.; Taddei, M.; Wermuth, C-G. *Heterocycles* 1996, 43, 2131–2138.) with bis(pinacolato)diboron reagent in the presence of a suitable palladium (II) catalyst such as [1,1'-bis(diphenylphosphino)-ferrocene]dichloropalladium (II) (Pd(dppf)Cl$_2$) and potassium acetate in a polar, inert organic solvent such as methyl sulfoxide at about 80° C. under an inert atmosphere for a period of 6–24 hours provided the vinyl dioxaborolane 40. Borolane 40 can be further reacted with an aryl halide such as 41 in the presence of a palladium catalyst such as tetrakis(triphenylphosphine)palladium (0) (Pd(Ph$_3$)$_4$) and potassium phosphate in an inert solvent such as N,N-dimethylformamide to give the coupled 4-aryl tetrahydropyridine product 42. The tert-butyloxycarbonyl protecting group can be removed by any of the known methods such as treatment with a protic acid such as hydrogen chloride in an inert organic solvent such as ethyl acetate or trifluoroacetic acid in methylene chloride to give amine 43. Alternatively, it is sometimes desirable to reduce the double bond in synthetic intermediate 42. This can be effected by treatment with hydrogen at atmospheric or elevated pressure and a noble metal catalyst on carbon such as palladium (0) or platinum(IV) oxide in an inert organic solvent such as ethanol, ethyl acetate, acetic acid or mixtures thereof to give the 4-arylpiperidine 44. Removal of the tert-butyloxycarbonyl protecting group as described above provides amine 45. Both amine intermediates, 43 and 45, may be used as coupling partners in Reaction Scheme A.

Scheme J

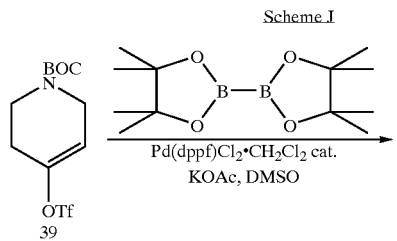

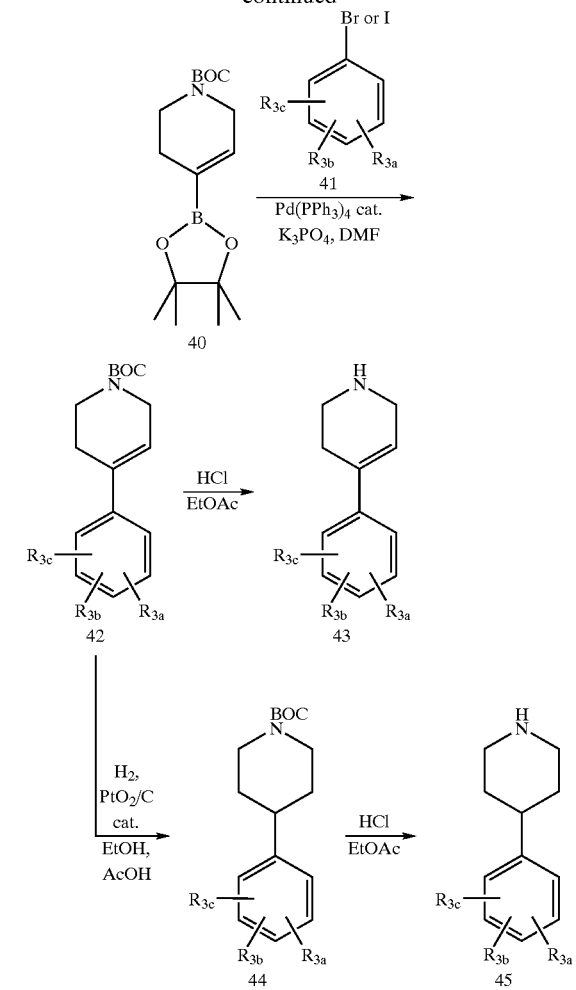

As shown in Reaction Scheme K, aryl groups containing substituents with acidic hydrogens (e.g. 46 and 48) can modified by alkylation under known protocols. For instance, treatment of esters 46 or 48 with a strong base such a lithium diisopropylamide at low temperature in an inert organic solvent such as tetrahydrofuran can form an intermediate enolate which can be reacted in a second step with any alkylating agent (B-LG) such as iodomethane, iodoethane, 1,2-dibromoethane or the like to form the corresponding alkylated product. In addition to ester groups, related amides and functionalities that promote the formation of a stable anion can be alkylated under similar protocols.

Scheme K

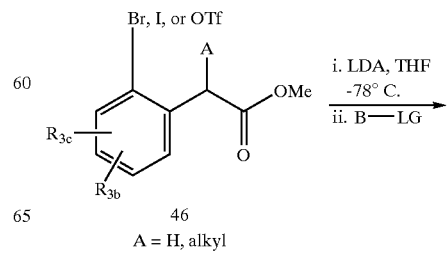

A = H, alkyl

-continued

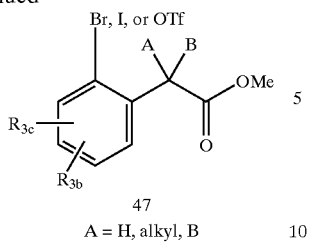

47
A = H, alkyl, B

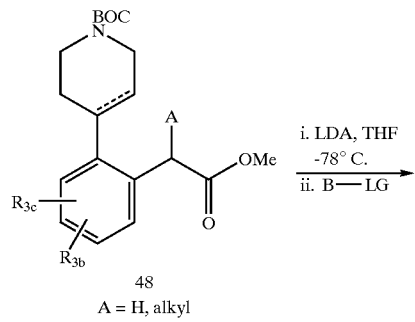

48
A = H, alkyl i. LDA, THF
-78° C.
ii. B—LG

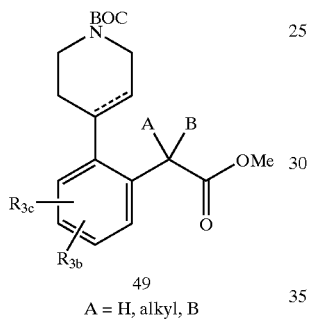

49
A = H, alkyl, B

-continued

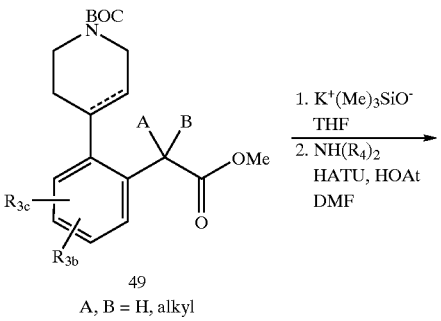

50
A, B = H, alkyl

1. K⁺(Me)₃SiO⁻
   THF
2. NH(R₄)₂
   HATU, HOAt
   DMF

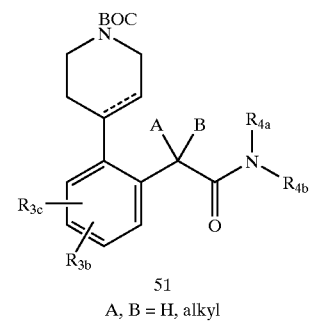

51
A, B = H, alkyl

Ester intermediates such as 47 and 49 may be further modified by conversion to the corresponding carboxylic acids and coupled with amines to form amides as described in Reaction Scheme L. Conversion of the methyl esters 47 and 49 to the carboxylic acid can be effected by dealkylation using potassium trimethylsilanolate at room temperature in an inert organic solvent such as tetrahydrofuran for a period of about one to about 24 hours to provide, after acidification, the corresponding carboxylic acids. In certain cases, a base-catalyzed hydrolysis known to those skilled in the art may be used to effect this same transformation. These acids may be reacted further to form amides by treatment with a primary or secondary amine under a variety of amide coupling protocols such as described in Scheme A to provide intermediates 50 and 51.

Scheme L

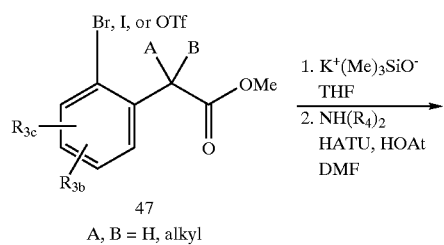

47
A, B = H, alkyl

1. K⁺(Me)₃SiO⁻
   THF
2. NH(R₄)₂
   HATU, HOAt
   DMF

Reaction Scheme M illustrates general methods for the elaboration of an $R^1$ substituent following assembly of a compound of structural formula I (wherein $R^1$=BOC) as described in reaction Scheme A. The N-BOC protected compound of structural formula I is first deprotected under acidic conditions for instance by treatment with hydrogen chloride in ethyl acetate or using trifluoroacetic acid in dichloromethane. The resulting heterocyclic compound of structural formula I ($R^1$=H) may then be subjected to one of several alkylation strategies known in organic chemistry. For instance, compounds (I) ($R^1$=H) may be utilized in a reductive amination reaction with a suitable carbonyl containing partner (52). The reductive amination is achieved by initial formation of an imine between the amine of formula I ($R^1$=H) and either an aldehyde or ketone of formula 52. The intermediate imine is then treated with a reducing agent capable of reducing carbon-nitrogen double bonds such as sodium cyanoborohydride or sodium triacetoxyborohydride and an alkylated product of structural formula I is produced. Alternatively, a heterocyclic compound of structural formula (I) ($R^1$=H) may be directly alkylated using an alkylating agent such as 53 in a polar aprotic solvent such as DMF. In this reaction, the substituent Z of compound 53 is a good leaving group such as a halide, mesylate or triflate and the product is the compound of structural formula I bearing the $R^1$ substituent.

Scheme M

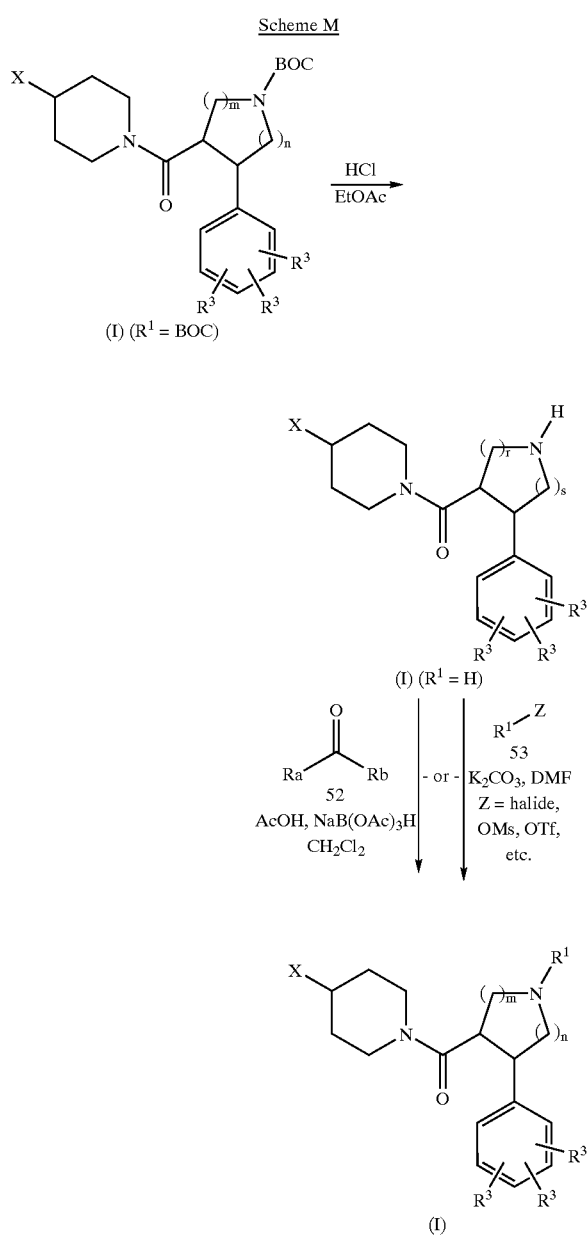

The following Examples are provided to illustrate the invention and are not to be construed as limiting the scope of the invention in any manner. Intermediate 1–7 was prepared as described in Scheme N following the general procedure described in Scheme F.

Scheme N

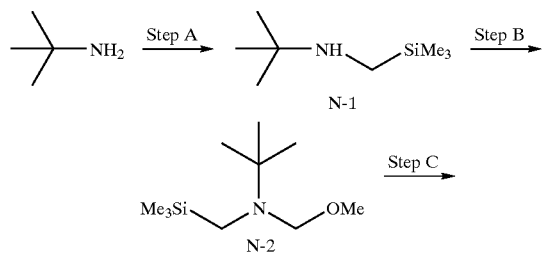

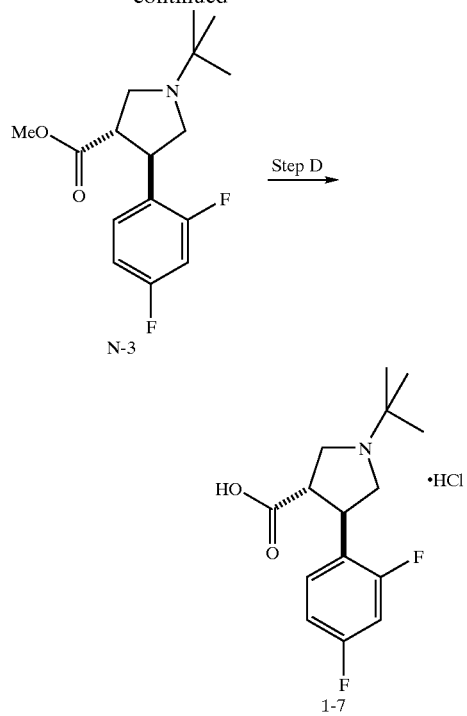

Step A: Preparation of N-Tert-Butyl-N-(Trimethylsilylmethyl)Amine (N-1)

A mixture of tert-butylamine (18.0 mL, 171 mmol) and (chloromethyl)trimethylsilane (7.00 g, 57.1 mmol) was heated in a thick-walled glass tube at 200° C. overnight. After cooling to ambient temperature, the reaction mixture was poured into 1 N NaOH and extracted three times with diethyl ether. The combined organic extracts were washed with brine, dried (MgSO$_4$), and the volatiles evaporated in vacuo. Distillation (atmospheric pressure; ~135° C.) of the residual liquid gave the title compound as a colorless liquid (7.67 g).

Step B: Preparation of N-Tert-Butyl-N-(Methoxymethyl)-N-(Trimethylsilylmethyl)Amine (N-2)

N-tert-Butyl-N-(trimethylsilylmethyl)amine (N-1) (8.47 g, 53.1 mmol) was added dropwise, over approximately 30 min, via a pressure equalizing addition funnel to a stirred solution of aqueous formaldehyde (5.98 mL of a 37 wt. % solution in water, 79.7 mmol) at 0° C. (ice cooling). After 45 min, methanol (6.45 mL, 159.3 mmol) was added and the resulting solution was saturated with potassium carbonate. After stirring vigorously for approximately 5 h, the aqueous phase was removed. The organic phase was saturated with potassium carbonate and stirred overnight. The reaction mixture was poured into water and extracted three times with diethyl ether. The combined organic extracts were washed with brine, dried (MgSO$_4$) and the volatiles evaporated in vacuo. Distillation (high vacuum; ~70° C.) of the residual liquid afforded the title compound as a colorless liquid (3.50 g).

Step C: Preparation of Methyl (3R,4S)-1-Tert-Butyl-4-(2,4-Difluorophenyl)Pyrrolidine-3-Carboxylate and Methyl (3S,4R)-1-Tert-Butyl-4-(2,4-Difluorophenyl)Pyrrolidine-3-Carboxylate (N-3)

Trifluoroacetic acid (116 µL, 1.51 mmol) was added to a solution of the product of step B (3.07 g, 15.1 mmol) and methyl (2E)-3-(2,4-difluorophenyl)prop-2-enoate (2.99 g, 15.1 mmol) in methylene chloride (60 mL) at ambient temperature. After 18 h, the reaction mixture was poured into saturated aqueous sodium bicarbonate and extracted three times with methlene chloride. The combined organic extracs were washed with brine, dried (Na$_2$SO$_4$) and concentrated in vacuo. Purification of the residue by normal phase medium pressure liquid chromatography on silica gel (gradient elution; 0–9% methanol (containing 10% v/v ammonium hydroxide)/methylene chloride as eluent) gave the title compound as a colorless liquid (3.50 g, 78%). The racemic titled compound was resolved into its enantiomeric components using preparative chiral high pressure liquid chromatography on CHIRALPAK AD Phase (5% isopropanol/heptanes as eluent) to give in order of elution: methyl (3S,4R)-1-tert-butyl-4-(2,4-difluorophenyl) pyrrolidine-3-carboxylate enantiomer (1.37 g) as a colorless oil followed by the methyl (3R,4S)-1-tert-butyl-4-(2,4-difluorophenyl)pyrrolidine-3-carboxylate enantiomer (1.18 g) as a colorless oil.

Step D: Preparation of (3S,4R)-1-Tert-Butyl-4-(2,4-Difluorophenyl)Pyrrolidine-3-Carboxylic Acid Hydrochloride Salt (1-7)

A mixture of the methyl (3S,4R)-1-tert-butyl-4-(2,4-difluorophenyl)pyrrolidine-3-carboxylate enantiomer of Step C (1.37 g, 4.61 mmol) and potassium trimethylsilanolate (0.68 g, 5.30 mmol) in diethyl ether (23 mL) was stirred at room temperature overnight. A saturated solution of hydrogen chloride in ethyl acetate was then added, the volatiles were evaporated and the residual solid used without further purification in the preparation of Examples detailed below.

SCHEME 1

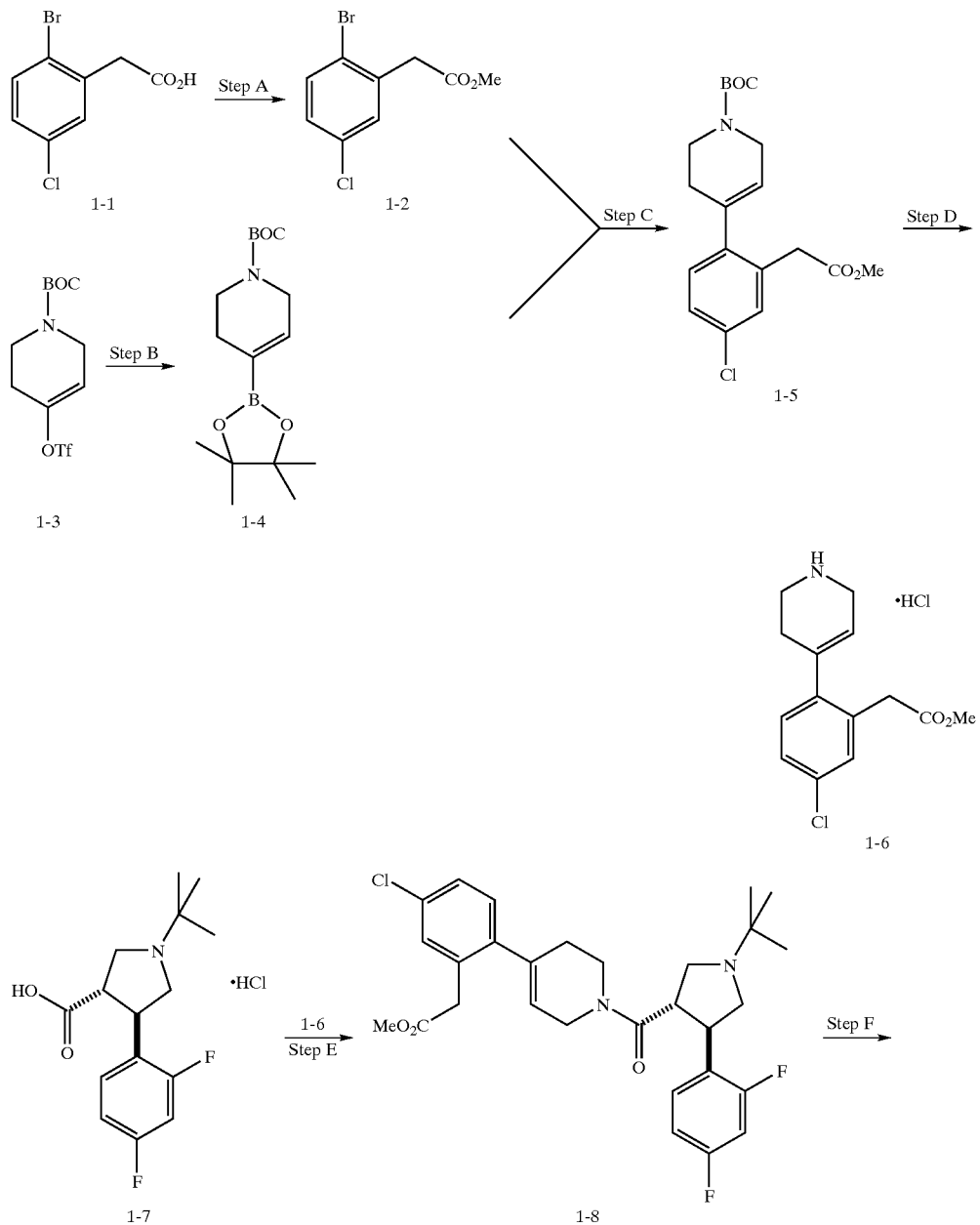

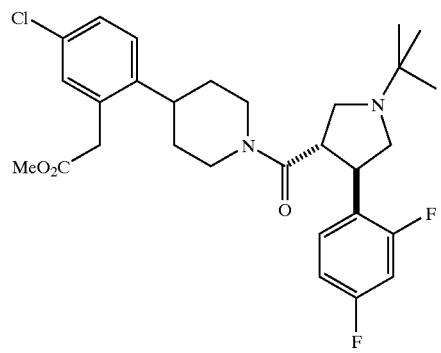

1-9

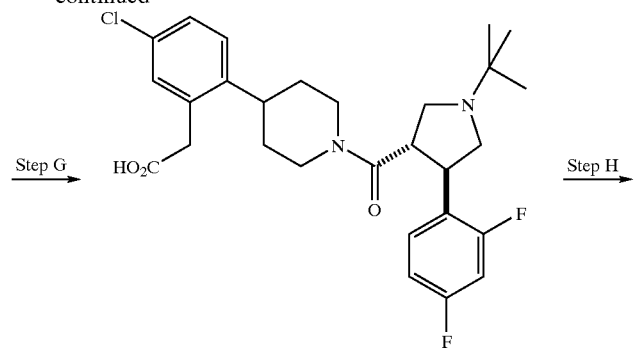

1-10

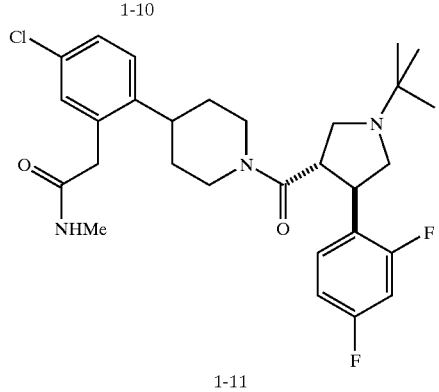

1-11

EXAMPLE 1

2-[2-(1-{[(3S,4R)-1-Tert-Butyl-4-(2,4-Difluorophenyl) Pyrrolidin-3-yl]Carbonyl}Piperidin-4-yl)-5-Chlorophenyl]-N-Methylacetamide (1-11)

Step A: Preparation of Methyl(2-Bromo-5-Chlorophenyl) Acetate (1-2)

A solution of (2-bromo-5-chlorophenyl)acetic acid (1-1) (15.0 g, 60.1 mmol) and concentrated sulfuric acid (0.150 mL of a 36N solution) in methanol (120 mL) was heated at reflux for approximately 15 h. After cooling to room temperature, the reaction mixture was concentrated in vacuo and the residue partitioned between methylene chloride and saturated aqueous sodium bicarbonate. The organic layer was separated and the aqueous phase re-extracted twice with methylene chloride. The combined organic extracts were washed with water, brine, dried (MgSO$_4$) and the volatiles evaporated. The residual colorless liquid (15.9 g) was used without further purification in the Step C below.

Step B: Preparation of Tert-Butyl 4-(4,4,5,5-Tetramethyl-1,3,2-Dioxaborolan-2-yl)-3,6-Dihydropyridine-1(2H)-Carboxylate (1-4)

A vigorously stirred suspension of the tert-butyl 4-{[(trifluoromethyl)sulfonyl]oxy}-3,6-dihydropyridine-1(2H)-carboxylate (1-3) (1.00 g, 3.02 mmol; prepared as described in Rohr, M.; Chayer, S.; Garrido, F.; Mann, A.; Taddei, M.; Wermuth, C-G. *Heterocycles* 1996, 43, 2131–2138), bis(pinacolato)diboron (0.844 g 3.32 mmol), potassium acetate (0.889 g, 9.06 mmol) and [1,1'-bis(diphenylphosphino)-ferrocene]dichloropalladium(II) (0.123 g of a 1:1 complex with methylene chloride, 0.151 mmol) in methyl sulfoxide (20 mL) was degassed via three vacuum/nitrogen ingress cycles and then heated at 80° C. for approximately 15 h. After cooling to ambient temperature, the reaction mixture was filtered through celite® eluting copiously with ethyl acetate. The filtrate was poured into water/brine (1:1) and the organic phase separated. The aqueous phase was re-extracted three times with ethyl acetate and the combined organic extracts were washed with brine, dried (MgSO$_4$) and concentrated in vacuo. Purification of the crude residue by flash chromatography on silica gel (gradient elution; 0%–25% ethyl acetate/hexanes as eluent) furnished 1-4 as a white solid (0.660 g).

Step C: Preparation of Tert-Butyl 4-[4-Chloro-2-(2-Methoxy-2-Oxoethyl)Phenyl]-3,6-Dihydropyridine-1(2H)-Carboxylate (1-5)

A vigorously stirred mixture of the tert-butyl 4-(4,4,5,5-tetramethyl-1,3,2-dioxaborolan-2-yl)-3,6-dihydropyridine-1(2H)-carboxylate (1-4) (1.40 g, 4.53 mmol), methyl(2-bromo-5-chlorophenyl)acetate (1-2) (1.31 g, 4.98 mmol), potassium phosphate tribasic (2.85 g, 13.6 mmol) and tetrakis(triphenylphosphine)palladium(0) (0.262 g, 0.227 mmol) in N,N-dimethylformamide (22 mL) was degassed via three vacuum/nitrogen ingress cycles and then heated at 100° C. for approximately 18 h. After cooling to room temperature, the reaction mixture was poured into water and extracted three times with ethyl acetate. The combined organic extracts were washed with brine, dried (MgSO$_4$) and concentrated in vacuo. Purification of the crude residue by flash chromatography on silica gel (gradient elution; 0%–25% ethyl acetate/hexanes as eluent) afforded 1-5 (0.967 g) as a colorless oil.

Step D: Preparation of Methyl [5-Chloro-2-(1,2,3,6-Tetrahydropyridin-4-yl)Phenyl]Acetate Hydrochloride (1-6)

A saturated solution of hydrogen chloride in ethyl acetate (6 mL) was added to a solution of tert-butyl 4-[4-chloro-2-(2-methoxy-2-oxoethyl)phenyl]-3,6-dihydropyridine-1(2H)-carboxylate (1-5) (0.950 g, 2.60 mmol) in methylene chloride (6 mL) at 0° C. After 1 h, the volatiles were evaporated in vacuo, and the crude residue triturated twice with dry diethyl ether to give 1-6 (0.690 g) as a flocculent pale yellow solid (m/z (ES) 266 (MH$^+$).

Step E: Preparation of Methyl [2-(1-{[(3S,4R)-1-Tert-Butyl-4-(2,4-Difluorophenyl)Pyrrolidin-3-yl]Carbonyl}-1,2,3,6-Tetrahydropyridin-4-yl)-5-Chlorophenyl]Acetate (1-8)

N,N-diisopropylethylamine (1.36 mL, 7.80 mmol) was added to a stirred suspension of (3S,4R)-1-tert-butyl-4-(2,4-difluorophenyl)pyrrolidine-3-carboxylic acid (1-7) (0.831 g, 2.60 mmol), methyl [5-chloro-2-(1,2,3,6-tetrahydropyridin-4-yl)phenyl]acetate hydrochloride (1-6) (0.690 g, 2.60 mmol), O-(7-azabenzotriazol-1-yl)-1,1,3,3-tetramethyluronium hexafluorophosphate (1.19 g, 3.12 mmol) and 1-hydroxy-7-azabenzotriazole (0.425 g, 3.12 mmol) in N,N-dimethylformamide (5.2 mL) at ambient temperature. After approximately 18 h, the reaction mixture was poured into saturated aqueous sodium bicarbonate and extracted three times with ethyl acetate. The combined organic extracts were washed with water, brine, dried ($Na_2SO_4$) and concentrated in vacuo. Purification of the crude residue by flash chromatography on silica gel (gradient elution; 0%–15% methanol (containing 10% v/v ammonium hydroxide)/methylene chloride as eluent) provided 1-8 as a pale yellow oil (m/z (ES) 531 ($MH^+$)).

Step F: Preparation of Methyl [2-(1-{[(3S,4R)-1-Tert-Butyl-4-(2,4-Difluorophenyl)Pyrrolidin-3-yl]Carbonyl}Piperidin-4-yl)-5-Chlorophenyl]acetate (1-9)

A mixture of methyl [2-(1-{[(3S,4R)-1-tert-butyl-4-(2,4-difluorophenyl)pyrrolidin-3-yl]carbonyl}-1,2,3,6-tetrahydropyridin-4-yl)-5-chlorophenyl]acetate (1-8) (2.60 mmol) and platinum (IV) oxide (0.300 g) in ethanol/glacial acetic acid (1:1, 20 mL) was hydrogenated at atmospheric pressure for approximately 15 h. The resulting mixture was filtered through a short column of celite®, eluting copiously with ethanol. The filtrate was evaporated and the residue was partitioned between methylene chloride and saturated aqueous sodium bicarbonate. The organic layer was separated and the aqueous phase was re-extracted twice with methylene chloride. The combined organic extracts were washed with water, brine, dried ($Na_2SO_4$), and concentrated in vacuo. Purification of the crude residue by flash chromatography on silica gel (gradient elution; 0%–15% methanol (containing 10% v/v ammonium hydroxide)/methylene chloride as eluent) furnished 1-9 (1.25 g) as a colorless foam (m/z (ES) 533 ($MH^+$)).

Step G: Preparation of [2-(1-{[(3S,4R)-1-Tert-Butyl-4-(2,4-Difluorophenyl)Pyrrolidin-3-yl]Carbonyl}Piperidin-4-yl)-5-Chlorophenyl]Acetic Acid (1-10)

Potassium trimethylsilanolate (0.900 g, 7.05 mmol) was added to a stirred solution of methyl [2-(1-{[(3S,4R)-1-tert-butyl-4-(2,4-difluorophenyl)pyrrolidin-3-yl]carbonyl}-piperidin-4-yl)-5-chlorophenyl]acetate (1-9) (1.25 g, 2.35 mmol) in tetrahydrofuran (24 mL) at room temperature. After approximately 15 h, the volatiles were evaporated in vacuo and the crude residue was treated with a saturated solution of hydrogen chloride in ethyl acetate. After approximately 5 min, the reaction mixture was concentrated under reduced pressure and the crude residue triturated twice with dry diethyl ether to give 1-10 as an amorphous white solid (m/z (ES) 519 ($MH^+$)).

Step H: Preparation of 2-[2-(1-{[(3S,4R)-1-Tert-Butyl-4-(2,4-Difluorophenyl)Pyrrolidin-3-yl]Carbonyl}Piperidin-4-yl)-5-Chlorophenyl]-N-Methylacetamide (1-11)

N,N-diisopropylethylamine (0.166 mL, 0.953 mmol) was added to a stirred suspension of [2-(1-{[(3S,4R)-1-tert-butyl-4-(2,4-difluorophenyl)pyrrolidin-3-yl]carbonyl}piperidin-4-yl)-5-chlorophenyl]acetic acid (1-10) (40.0 mg), methylamine.HCl (42.9 mg, 0.635 mmol), O-(7-azabenzotriazol-1-yl)-1,1,3,3-tetramethyluronium hexafluorophosphate (48.3 mg, 0.127 mmol) and 1-hydroxy-7-azabenzotriazole (17.3 mg, 0.127 mmol) in N,N-dimethylformamide (0.65 mL) at ambient temperature. After approximately 18 h, the reaction mixture was poured into saturated aqueous sodium bicarbonate and extracted three times with ethyl acetate. The combined organic extracts were washed with water, brine, dried ($Na_2SO_4$) and concentrated in vacuo. Purification of the residue by preparative reversed phase high pressure liquid chromatography on YMC Pack Pro C18 phase (gradient elution; 0%–100% acetonitrile/water as eluent, 0.1% TFA modifier) gave 1-11 as a buff white solid (m/z (ES) 532 ($MH^+$)).

Following procedures similar to that described above for Example 1, the following compounds were prepared:

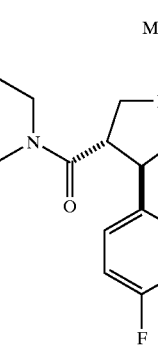

| Ex. # | $R^{3a}$ | $R^{3b}$ | Parent Ion m/z (M + H) |
|---|---|---|---|
| 2 | H | 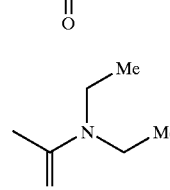 | 498 |
| 3 | H | 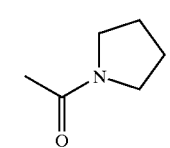 | 526 |
| 4 | H | 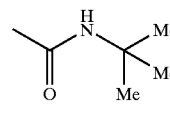 | 524 |
| 5 | H | 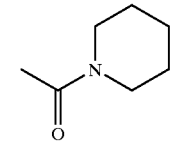 | 526 |
| 6 | H | 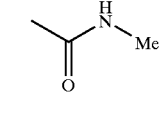 | 538 |
| 7 | H |  | 484 |

-continued
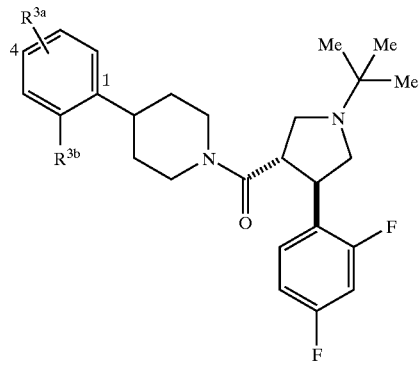
| Ex. # | R3a | R3b | Parent Ion m/z (M + H) |
|---|---|---|---|
| 8 | H | -C(O)NH-Et | 498 |
| 9 | H | -C(O)NH-propyl | 512 |
| 10 | H | -C(O)-azetidinyl | 510 |
| 11 | H | -C(O)NH2 | 470 |
| 12 | 4-F | CN | 470 |
| 13 | 4-Cl | -C(O)NH2 | 504 |
| 14 | 4-Cl | -C(O)NHMe | 518 |
| 15 | H | -C(O)OMe (propanoate) | 499 |
| 16 | H | -CH2C(O)NHMe | 498 |
| 17 | H | -CH2C(O)NMe2 | 512 |
-continued
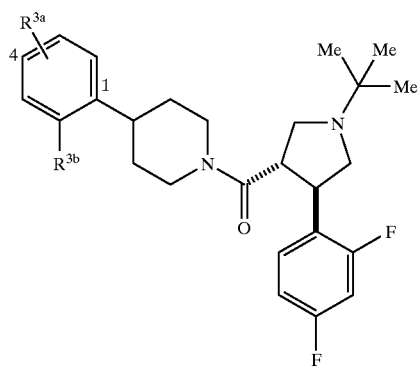
| Ex. # | R3a | R3b | Parent Ion m/z (M + H) |
|---|---|---|---|
| 18 | H | -CH2C(O)NH-Et | 512 |
| 19 | H | -CH2C(O)NH-CH(Me)2 | 526 |
| 20 | H | -CH2C(O)NH-cyclobutyl | 538 |
| 21 | H | -CH2C(O)-azetidinyl | 524 |
| 22 | H | -CH2C(O)NH-C(Me)3 | 540 |
| 23 | H | -CH2C(O)N(Me)Et | 526 |
| 24 | H | -CH2C(O)N(Me)CH(Me)2 | 540 |
| 25 | H | -CH2C(O)N(Et)2 | 540 |

-continued
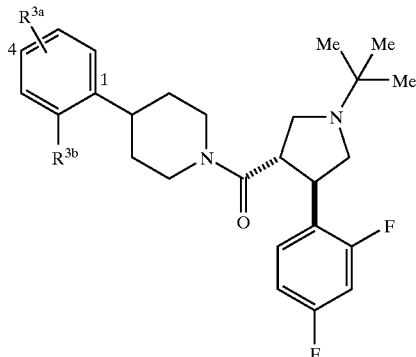
| Ex. # | R³ᵃ | R³ᵇ | Parent Ion m/z (M + H) |
|---|---|---|---|
| 26 | H | 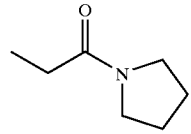 | 538 |
| 27 | 4-Cl | 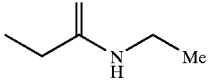 | 546 |
| 28 | 4-Cl | 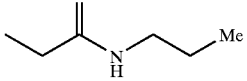 | 560 |
| 29 | 4-Cl | 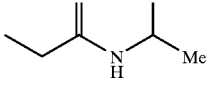 | 560 |
| 30 | 4-Cl | 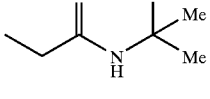 | 574 |
| 31 | 4-Cl | 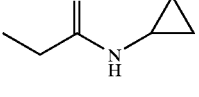 | 558 |
| 32 | 4-Cl | 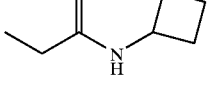 | 572 |
| 33 | 4-Cl | 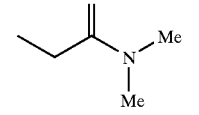 | 546 |
| 34 | 4-Cl | 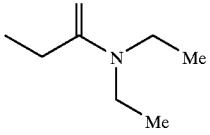 | 574 |
-continued
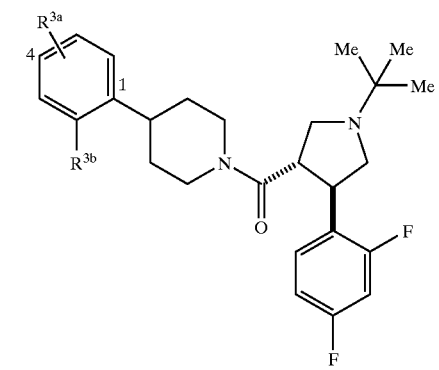
| Ex. # | R³ᵃ | R³ᵇ | Parent Ion m/z (M + H) |
|---|---|---|---|
| 35 | 4-Cl | 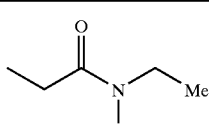 | 560 |
| 36 | 4-Cl | 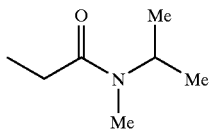 | 574 |
| 37 | 4-Cl | 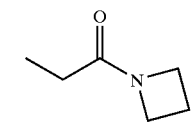 | 558 |
| 38 | 4-Cl | 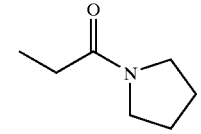 | 572 |
| 39 | 4-Cl | 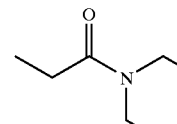 | 586 |
| 40 | 4-Cl | 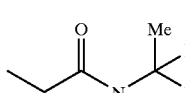 | 588 |
| 41 | 4-Cl | 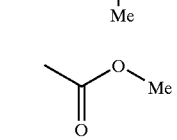 | 519 |
| 42 | 4-Cl | 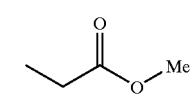 | 533 |

-continued
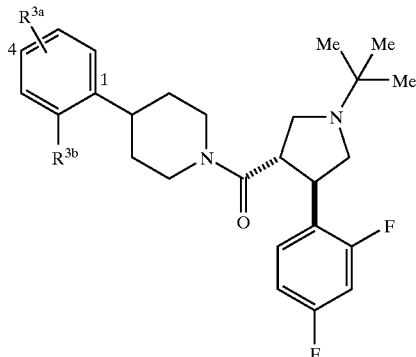
| Ex. # | R3a | R3b | Parent Ion m/z (M + H) |
|---|---|---|---|
| 43 | H | Me-N(Me)-SO2- | 534 |
| 44 | 5-F | MeNH-C(O)- | 503 |
| 45 | 3-CH3 | MeO-C(O)- | 499 |
| 46 | 3-CH3 | MeNH-C(O)- | 498 |
| 47 | 3-CH3 | Me2N-C(O)- | 512 |
| 48 | 4-CH3 | EtO-C(O)- | 513 |
| 49 | 4-CH3 | MeNH-C(O)- | 498 |
| 50 | 4-Cl | tBuO-C(O)- | 561 |
| 51 | 5-Me | MeNH-C(O)- | 498 |
| 52 | 4-F | MeNH-C(O)- | 503 |
-continued
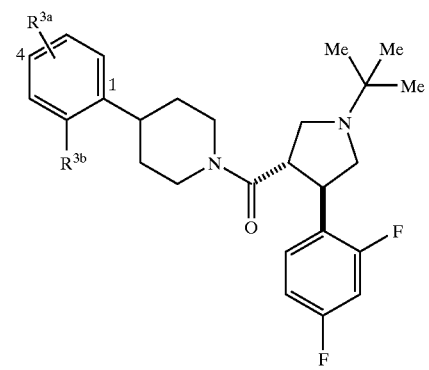
| Ex. # | R3a | R3b | Parent Ion m/z (M + H) |
|---|---|---|---|
| 53 | 4-Cl | Me2N-C(O)- | 532 |
| 54 | 4-Cl | EtNH-C(O)- | 532 |
| 55 | 4-Cl | Et2N-C(O)- | 560 |
| 56 | 4-Cl | iPrNH-C(O)- | 546 |
| 57 | 4-Cl | azetidinyl-C(O)- | 544 |
| 58 | 4-Cl | cyclopropyl-NH-C(O)- | 544 |
| 59 | 4,5-di-F | MeNH-C(O)- | 520 |
| 60 | 4-F | azabicyclo-C(O)- | 568 |

-continued
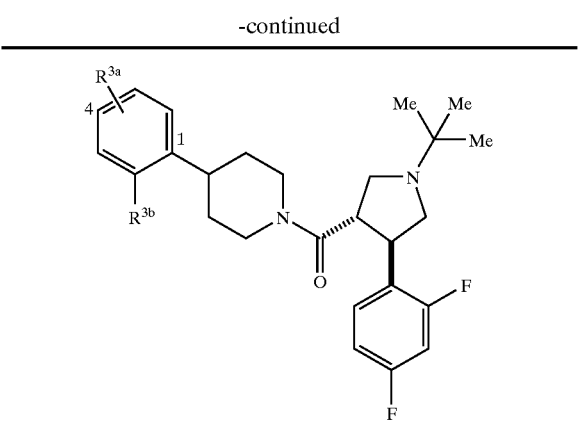
| Ex. # | R³ᵃ | R³ᵇ | Parent Ion m/z (M + H) |
|---|---|---|---|
| 61 | 4-CF₃ | 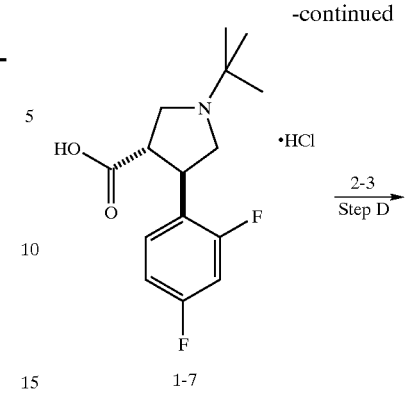 | 552 |
SCHEME 2
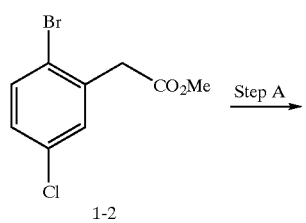
Step A →
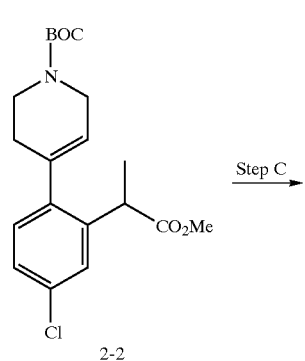
-continued
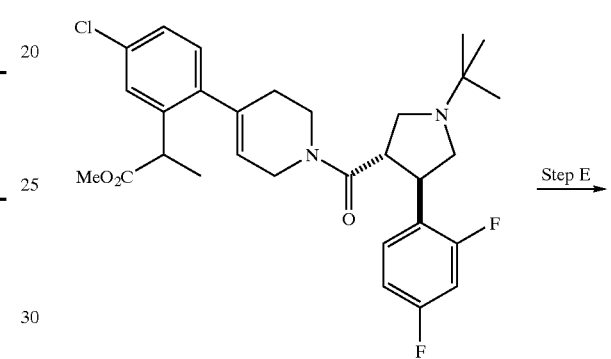
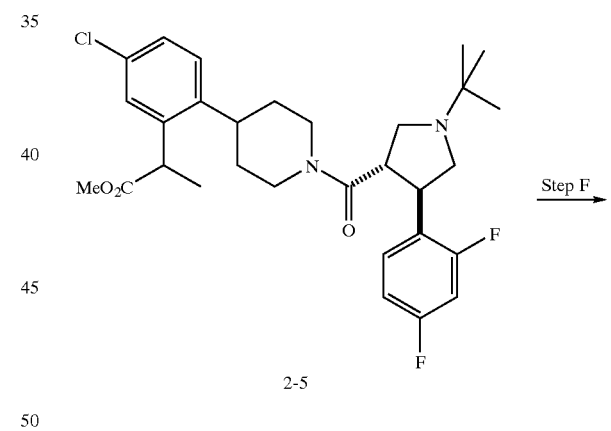
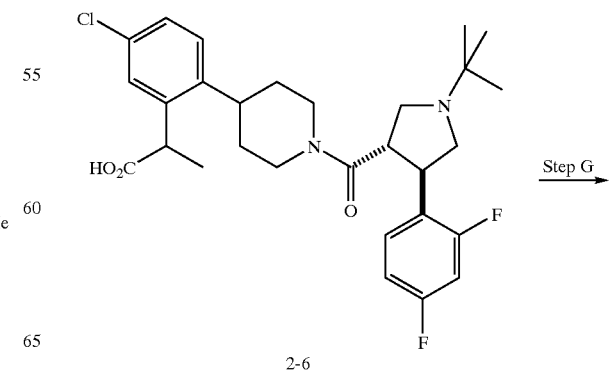

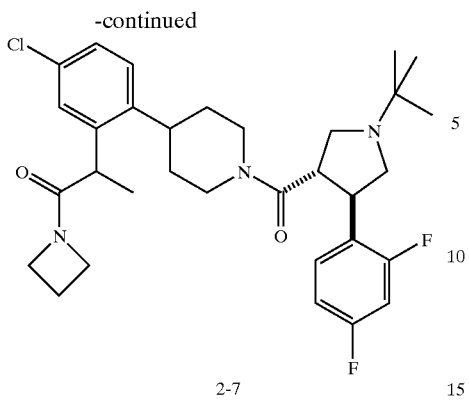

2-7

EXAMPLE 62

4-[2-(2-Azetidin-1-yl-1-Methyl-2-Oxoethyl)-4-Chlorophenyl]-1-{[(3S,4R)-1-Tert-Butyl-4-(2,4-Difluorophenyl)Pyrrolidin-3-yl]Carbonyl}Piperidine (2-7)

Step A: Preparation of Methyl 2-(2-Bromo-5-Chlorophenyl) Propanoate (2-1)

A solution of n-butyllithium (1.67 mL of a 2.5 M solution in hexanes, 4.17 mmol) was added dropwise via syringe to a stirred solution of diisopropylamine (0.61 mL, 4.36 mmol) in tetrahydrofuran (10 mL) at −78° C. After approximately 10 min, the reaction mixture was warmed to 0° C. and aged for another 10 min. After re-cooling to −78° C., a solution of methyl (2-bromo-5-chlorophenyl)acetate (1-2) (1.00 g, 3.79 mmol) in tetrahydrofuran (10 mL) was added dropwise via syringe and the resulting yellow mixture was stirred at −78° C. for approximately 30 min. Iodomethane (0.35 mL, 5.69 mmol) was added and after 1 h, the reaction mixture was warmed to ambient temperature and quenched with saturated aqueous ammonium chloride. The resulting mixture was poured into water and extracted three times with ethyl acetate. The combined organic extracts were washed with brine, dried (MgSO$_4$) and concentrated in vacuo. Purification of the crude residue by flash chromatography on silica gel (gradient elution; 0–20% ethyl acetate/hexanes as eluent) furnished 2-1 as a colorless oil (1.00 g).

Step B: Preparation of Tert-Butyl 4-[4-Chloro-2-(2-Methoxy-1-Methyl-2-Oxoethyl)Phenyl]-3,6-Dihydropyridine-1(2H)-Carboxylate (2-2)

A vigorously stirred mixture of tert-butyl 4-(4,4,5,5-tetramethyl-1,2,3-dioxaborolan-2-yl)-3,6-dihydropyridine-1(2H)-carboxylate (1.01 g, 3.27 mmol), methyl 2-(2-bromo-5-chlorophenyl)propanoate (2-1) (1.00 g, 3.60 mmol), potassium phosphate tribasic (2.08 g, 9.81 mmol) and tetrakis(triphenylphosphine)palladium(0) (0.189 g, 0.164 mmol) in N,N-dimethylformamide (13 mL) was degassed via three vacuum/nitrogen ingress cycles and then heated at 100° C. for approximately 18 h. After cooling to room temperature, the reaction mixture was poured into water and extracted three times with ethyl acetate. The combined organic extracts were washed with brine, dried (MgSO$_4$) and concentrated in vacuo. Purification of the crude residue by flash chromatography on silica gel (gradient elution; 0–25% ethyl acetate/hexanes as eluent) afforded 2-2 (0.73 g) as a colorless oil.

Step C: Preparation of Methyl 2-[5-Chloro-2-(1,2,3,6-Tetrahydropyridin-4-yl)Phenyl]Propanoate (2-3)

A saturated solution of hydrogen chloride in ethyl acetate (6 mL) was added to a solution of tert-butyl 4-[4-chloro-2-(2-methoxy-1-methyl-2-oxoethyl)phenyl]-3,6-dihydropyridine-1(2H)-carboxylate (0.730 g, 1.92 mmol) in methylene chloride (6 mL) at 0° C. After 1 h, the volatiles were evaporated in vacuo, and the crude residue triturated twice with dry diethyl ether to give 2-3 (0.605 g) (m/z (ES) 280 (MH$^+$).

Step D: Preparation of Methyl 2-[2-(1-{[(3S,4R)-1-Tert-Butyl-4-(2,4-Difluorophenyl)Pyrrolidin-3-yl]Carbonyl}-1,2,3,6-Tetrahydropyridin-4-yl)-5-Chlorophenyl]Propanoate (2-4)

N,N-diisopropylethylamine (1.00 mL, 5.76 mmol) was added to a stirred suspension of (3S,4R)-1-tert-butyl-4-(2,4-difluorophenyl)pyrrolidine-3-carboxylic acid (1-7) (0.614 g, 1.92 mmol), methyl 2-[5-chloro-2-(1,2,3,6-tetrahydropyridin-4-yl)phenyl]propanoate (2-3) (0.605 g, 1.92 mmol), O-(7-azabenzotriazol-1-yl)-1,1,3,3-tetramethyluronium hexafluorophosphate (0.876 g, 2.30 mmol) and 1-hydroxy-7-azabenzotriazole (0.314 g, 2.30 mmol) in N,N-dimethylformamide (3.8 mL) at ambient temperature. After approximately 18 h, the reaction mixture was poured into saturated aqueous sodium bicarbonate and extracted three times with ethyl acetate. The combined organic extracts were washed with water, brine, dried (Na$_2$SO$_4$) and concentrated in vacuo. Purification of the crude residue by flash chromatography on silica gel (gradient elution; 0–15% methanol (containing 10% v/v ammonium hydroxide)/methylene chloride as eluent) provided 2-4 as a pale yellow oil; (m/z (ES) 545 (MH$^+$).

Step E: Preparation of Methyl 2-[2-(1-{[(3S,4R)-1-Tert-Butyl-4-(2,4-Difluorophenyl)Pyrrolidin-3-yl]Carbonyl}Piperidin-4-yl)-5-Chlorophenyl]Propanoate (2-5)

A mixture of methyl 2-[2-(1-{[(3S,4R)-1-tert-butyl-4-(2,4-difluorophenyl)pyrrolidin-3-yl]carbonyl}-1,2,3,6-tetrahydropyridin-4-yl)-5-chlorophenyl]propanoate (2-4) (1.92 mmol) and platinum (TV) oxide (0.350 g) in ethanol/glacial acetic acid (1:1, 20 mL) was hydrogenated at atmospheric pressure for approximately 15 h. The resulting mixture was filtered through a short column of celite®, eluted copiously with ethanol. The filtrate was evaporated and the residue was partitioned between methylene chloride and saturated aqueous sodium bicarbonate. The organic layer was separated and the aqueous phase was re-extracted twice with methylene chloride. The combined organic extracts were washed with water, brine, dried (Na$_2$SO$_4$), and concentrated in vacuo. Purification of the crude residue by flash chromatography on silica gel (gradient elution; 0–15% methanol (containing 10% v/v ammonium hydroxide)/methylene chloride as eluent) furnished 2-5 (0.95 g) as a colorless foam (m/z (ES) 547 (MH$^+$).

Step F: Preparation of 2-[2-(1-{[(3S,4R)-1-Tert-Butyl-4-(2,4-Difluorophenyl)Pyrrolidin-3-yl]Carbonyl}-1,2,3,6-Tetrahydropyridin-4-yl)-5-Chlorophenyl]Propanoic Acid (2-6)

Potassium trimethylsilanolate (0.645 g, 5.03 mmol) was added to a stirred solution of methyl 2-[2-(1-{[(3S,4R)-1-tert-butyl-4-(2,4-difluorophenyl)pyrrolidin-3-yl]carbonyl}piperidin-4-yl)-5-chlorophenyl]propanoate (2-5) (1.10 g, 2.01 mmol) in tetrahydrofuran (10 mL) at room temperature. After approximately 15 h, the volatiles were evaporated in vacuo and the crude residue was treated with a saturated solution of hydrogen chloride in ethyl acetate. After approximately 5 min, the reaction mixture was concentrated under reduced pressure and the crude residue triturated twice with dry diethyl ether to give 2-6 as an amorphous white solid m/z 533 (MH$^+$).

Step G: 4-[2-(2-Azetidin-1-yl-1-Methyl-2-Oxoethyl)-4-Chlorophenyl]-1-{[(3S,4R)-1-Tert-Butyl-4-(2,4-Difluorophenyl)Pyrrolidin-3-yl]Carbonyl}Piperidine (2-7)

N,N-diisopropylethylamine (0.162 mL, 0.931 mmol) was added to a stirred suspension of 2-[2-(1-{[(3S,4R)-1-tertbutyl-4-(2,4-difluorophenyl)pyrrolidin-3-yl]carbonyl}-1,2,3,6-tetrahydropyridin-4-yl)-5-chlorophenyl]propanoic acid (2-6) (50.0 mg), azetidine.HCl (72.6 mg, 0.776 mmol), O-(7-azabenzotriazol-1-yl)-1,1,3,3-tetramethyluronium hexafluorophosphate (59.0 mg, 0.155 mmol) and 1-hydroxy-7-azabenzotriazole (21.1 mg, 0.155 mmol) in N,N-dimethylformamide (0.8 mL) at ambient temperature. After approximately 18 h, the reaction mixture was poured into saturated aqueous sodium bicarbonate and extracted three times with ethyl acetate. The combined organic extract was washed with water, brine, dried ($Na_2SO_4$) and concentrated in vacuo. Purification of the crude residue by preparative reversed phase high pressure liquid chromatography on YMC Pack Pro C18 phase (gradient elution; 0–100% acetonitrile/water as eluent, 0.1% TFA modifier) gave 2-7 as the trifluoroacetate salt (m/z (ES) 572 ($MH^+$)).

Following a procedure similar to that described above for Example 62, the following compounds were prepared:

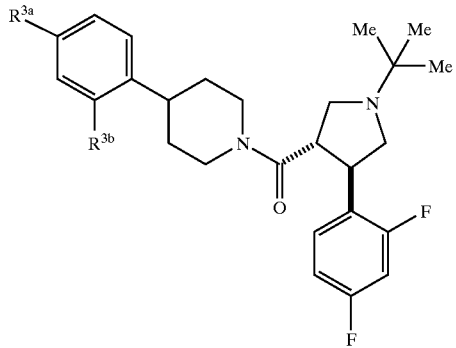

| Ex. # | $R^{3a}$ | $R^{3b}$ | Parent Ion m/z (M + H) |
|---|---|---|---|
| 63 | Cl | (isobutyramide, NHMe) | 546 |
| 64 | F | (isobutyramide, NHMe) | (blank) |
| 65 | Cl | (isobutyramide, NHEt) | 560 |
| 66 | Cl | (isobutyramide, NH-n-propyl) | 574 |
| 67 | Cl | (isobutyramide, NH-iPr) | 574 |
| 68 | Cl | (isobutyramide, NH-tBu) | 588 |
| 69 | Cl | (isobutyramide, NH-cyclopropyl) | 572 |
| 70 | Cl | (isobutyramide, NH-cyclobutyl) | 586 |
| 71 | Cl | (isobutyramide, NH-cyclopentyl) | 600 |
| 72 | Cl | (isobutyramide, NH-cyclohexyl) | 614 |
| 73 | Cl | (isobutyramide, NMe$_2$) | 560 |
| 74 | Cl | (isobutyramide, NEt$_2$) | 588 |

-continued
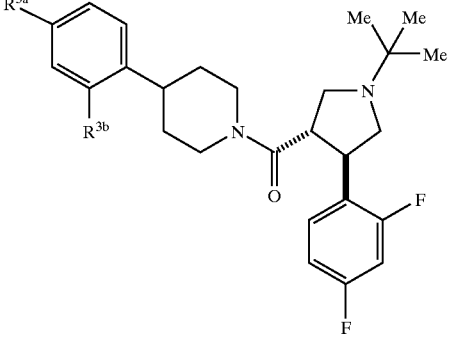
| Ex. # | R³ᵃ | R³ᵇ | Parent Ion m/z (M + H) |
|---|---|---|---|
| 75 | Cl | 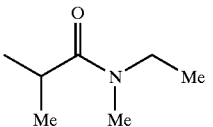 | 574 |
| 76 | Cl | 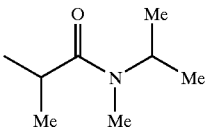 | 588 |
| 77 | Cl | 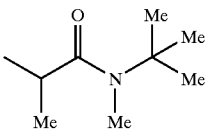 | 602 |
| 78 | Cl | 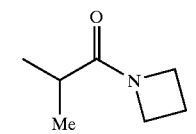 | 572 |
| 79 | Cl | 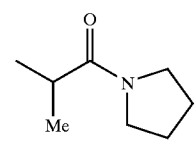 | 586 |
| 80 | Cl | 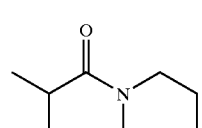 | 600 |
| 81 | Cl | 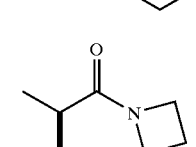 | 572 |
| 82 | Cl | 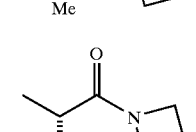 | 572 |
-continued
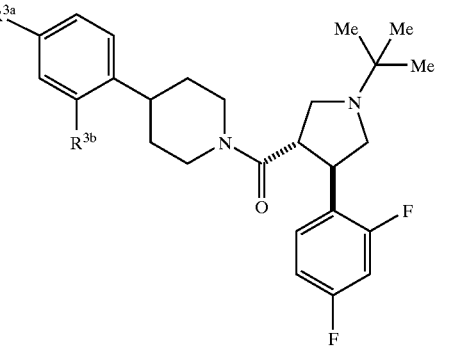
| Ex. # | R³ᵃ | R³ᵇ | Parent Ion m/z (M + H) |
|---|---|---|---|
| 83 | Cl | 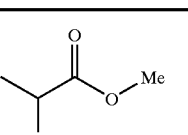 | |
| 84 | Cl | 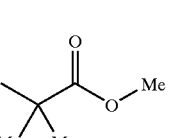 | 561 |
| 85 | H | 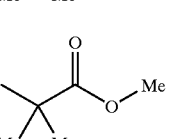 | 527 |
| 86 | Cl | 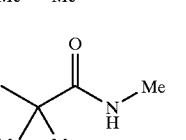 | |
| 87 | H | 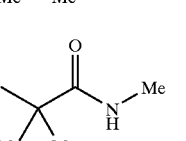 | 526 |
| 88 | Cl | 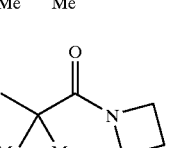 | 586 |
| 89 | F | 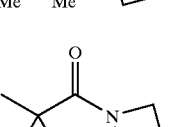 | 570 |
| 90 | H | 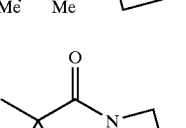 | 552 |

-continued

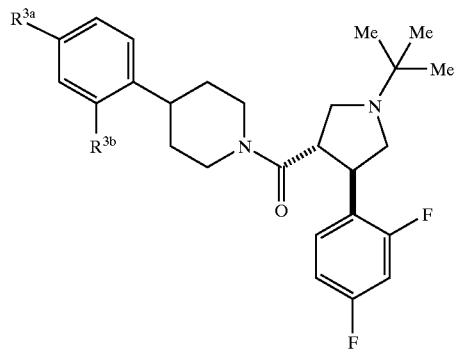

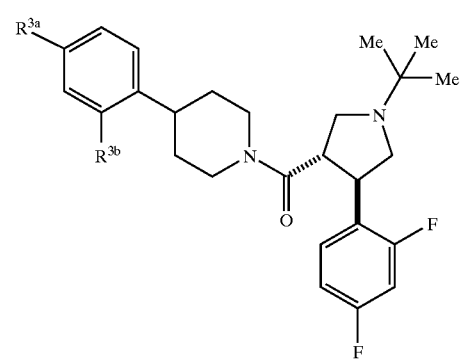

| Ex. # | R³ᵃ | R³ᵇ | Parent Ion m/z (M + H) |
|---|---|---|---|
| 91 | Cl | 1-methylcyclopropyl-C(O)-azetidinyl | 584 |
| 92 | F | 1-methylcyclopropyl-C(O)-azetidinyl | |
| 93 | Cl | 1-methylcyclopropyl-C(O)-NHMe | 558 |
| 94 | Cl | 1-methylcyclopropyl-C(O)-NMe₂ | |
| 95 | F | 1-methylcyclopropyl-C(O)-NMe₂ | 556 |
| 96 | Cl | C(Me)₂OH | 519 |
| 97 | Cl | C(Me)₂C(O)NH₂ | 530 |
| 98 | 5-F | C(Me)₂C(O)NHMe | 544 |

| Ex. # | R³ᵃ | R³ᵇ | Parent Ion m/z (M + H) |
|---|---|---|---|
| 99 | F | C(Me)₂C(O)N(Me)CH₂CH₂OH | 588 |
| 100 | F | C(Me)₂C(O)-morpholinyl | 600 |
| 101 | Cl | C(Me)₂C(O)NHNH₂ | 561 |
| 102 | Cl | C(Me)₂C(O)NHNH-CH(Me)₂ | 603 |
| 103 | Cl | C(Me)₂C(O)NHNHC(O)Me | 603 |

Scheme 3

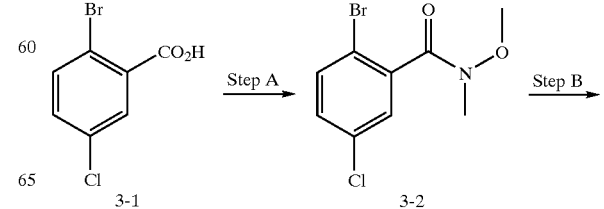

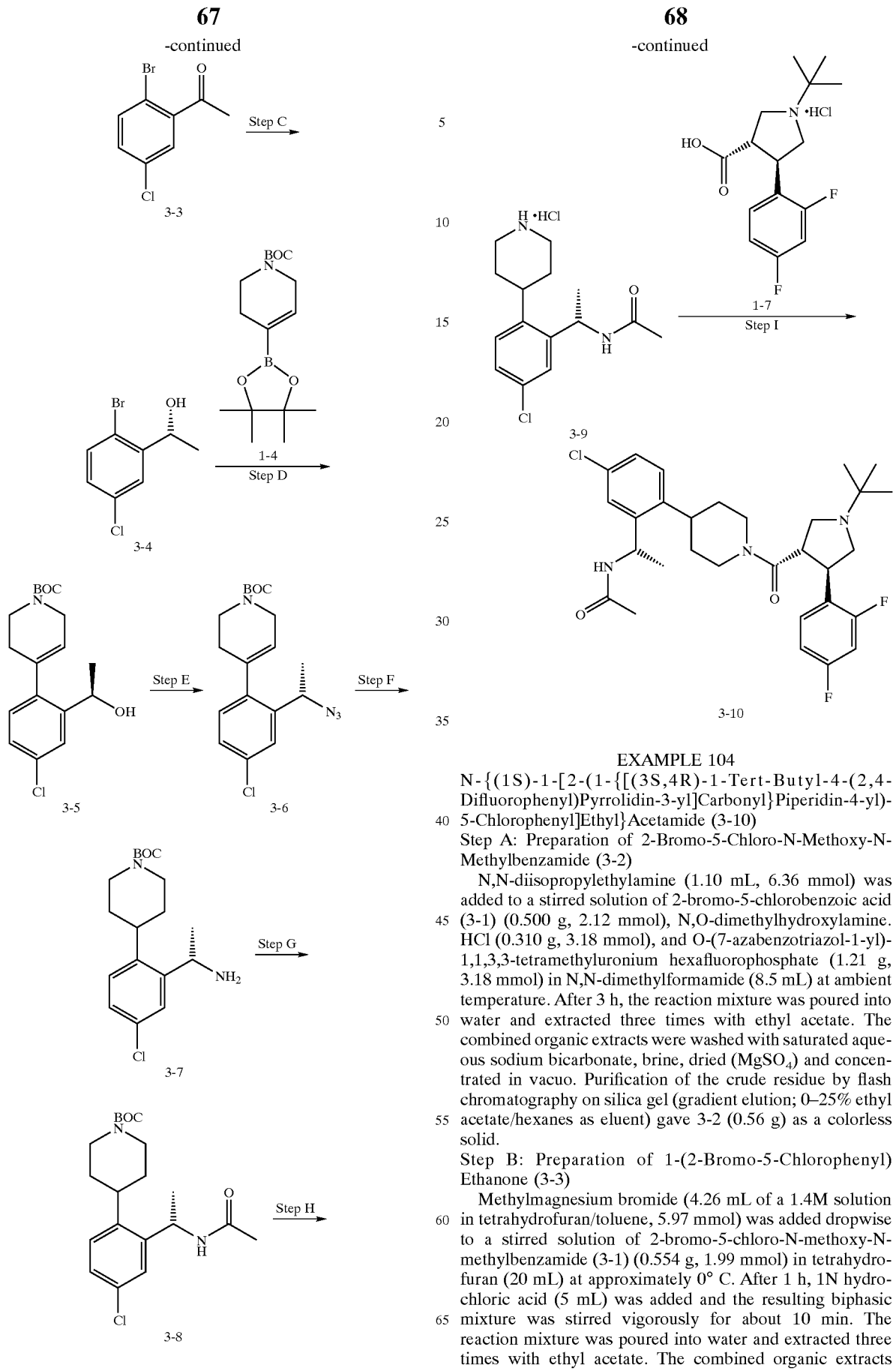

EXAMPLE 104

N-{(1S)-1-[2-(1-{[(3S,4R)-1-Tert-Butyl-4-(2,4-Difluorophenyl)Pyrrolidin-3-yl]Carbonyl}Piperidin-4-yl)-5-Chlorophenyl]Ethyl}Acetamide (3-10)

Step A: Preparation of 2-Bromo-5-Chloro-N-Methoxy-N-Methylbenzamide (3-2)

N,N-diisopropylethylamine (1.10 mL, 6.36 mmol) was added to a stirred solution of 2-bromo-5-chlorobenzoic acid (3-1) (0.500 g, 2.12 mmol), N,O-dimethylhydroxylamine. HCl (0.310 g, 3.18 mmol), and O-(7-azabenzotriazol-1-yl)-1,1,3,3-tetramethyluronium hexafluorophosphate (1.21 g, 3.18 mmol) in N,N-dimethylformamide (8.5 mL) at ambient temperature. After 3 h, the reaction mixture was poured into water and extracted three times with ethyl acetate. The combined organic extracts were washed with saturated aqueous sodium bicarbonate, brine, dried (MgSO$_4$) and concentrated in vacuo. Purification of the crude residue by flash chromatography on silica gel (gradient elution; 0–25% ethyl acetate/hexanes as eluent) gave 3-2 (0.56 g) as a colorless solid.

Step B: Preparation of 1-(2-Bromo-5-Chlorophenyl) Ethanone (3-3)

Methylmagnesium bromide (4.26 mL of a 1.4M solution in tetrahydrofuran/toluene, 5.97 mmol) was added dropwise to a stirred solution of 2-bromo-5-chloro-N-methoxy-N-methylbenzamide (3-1) (0.554 g, 1.99 mmol) in tetrahydrofuran (20 mL) at approximately 0° C. After 1 h, 1N hydrochloric acid (5 mL) was added and the resulting biphasic mixture was stirred vigorously for about 10 min. The reaction mixture was poured into water and extracted three times with ethyl acetate. The combined organic extracts were washed with brine, dried (MgSO$_4$) and concentrated in vacuo. Purification of the crude residue by flash chromatography on silica gel (gradient elution; 0–10% ethyl acetate/hexanes as eluent) provided 3-3 (0.44 g) as a colorless oil.

Step C: Preparation of (1R)-1-(2-Bromo-5-Chlorophenyl) Ethanol (3-4)

Trimethylborate (1.74 mL, 15.4 mmol) was added to a stirred solution of (S)-(−)-alpha,alpha-diphenyl-2-pyrrolidinemethanol (3.24 g, 12.8 mol) in tetrahydrofuran (350 mL) at room temperature. After 1.25 h, borane-methyl sulfide complex (70.4 mL of a 2M solution in tetrahydrofuran, 0.141 mol) was added slowly and a gentle effervesence was observed. The resulting solution was cooled to approximately 0° C. and a solution of 1-(2-bromo-5-chlorophenyl)ethanone (3-3) (30.0 g, 0.128 mmol) in tetrahydrofuran (150 mL) was then added uniformly over 1 h. After the addition, the resulting mixture was allowed to warm to ambient temperature and aged overnight. The reaction mixture was concentrated under reduced pressure to approximately one quarter of its original volume, poured into 1N hydrochloric acid and extracted three times with ethyl acetate. The combined organic extracts were washed with brine, dried (MgSO$_4$) and concentrated in vacuo. Purification of the crude residue by flash chromatography on silica gel (9% ethyl acetate/hexanes as eluent) afforded 3-4 as a colorless solid (25.8 g; 98:2 S/R enantiomeric ratio).

Step D: Preparation of Tert-Butyl 4-{4-Chloro-2-[(1R)-1-Hydroxyethyl]Phenyl}-3,6-Dihydropyridine-1(2H)-Carboxylate (3-5)

A vigorously stirred mixture of tert-butyl 4-(4,4,5,5-tetramethyl-1,2,3-dioxaborolan-2-yl)-3,6-dihydropyridine-1(2H)-carboxylate (1-4) (34.0 g, 0.110 mol), (1R)-1-(2-bromo-5-chlorophenyl)ethanol (3-4) (25.8 g, 0.110 mmol), potassium phosphate tribasic (70.0 g, 0.330 mol) and tetrakis(triphenylphosphine)palladium(0) (2.54 g, 2.20 mmol) in N,N-dimethylformamide (440 mL) was degassed via three vacuum/nitrogen ingress cycles and then heated at 100° C. for approximately 18 h. After cooling to room temperature, the reaction mixture was poured into ice/water (~1:1) and extracted three times with ethyl acetate. The combined organic extracts were washed with brine, dried (MgSO$_4$) and concentrated in vacuo. Purification of the crude residue by flash chromatography on silica gel (25% ethyl acetate/hexanes as eluent) afforded 3-5 (27.7 g) as a pale yellow foam.

Step E: Preparation of Tert-Butyl 4-{4-Chloro-2-[(1S)-1-(Azido)Ethyl]Phenyl}-3,6-Dihydropyridine-1-Carboxylate (3-6)

A solution of diethyl azodicarboxylate (49.6 mL, 0.315 mol) was added dropwise to a stirred mixture of tert-butyl 4-{4-chloro-2-[(1R)-1-hydroxyethyl]phenyl}-3,6-dihydropyridine-1(2H)-carboxylate (3-5) (26.7 g, 78.9 mmol), Zn(N$_3$)$_2$.2Py (prepared according to the method described by Viaud, M-C; Rollin, P. in *Synthesis*, 1990: 130–131) (48.5 g, 0.158 mol), triphenylphosphine (82.7 g, 0.315 mol) and imidazole (21.5 g, 0.315 mol) in dichloromethane at approximately 0° C. After the addition, the resulting mixture was allowed to warm to ambient temperature and stirred vigorously for 3 d. The reaction mixture was filtered through a short column of silica gel eluted with the appropriate volume of dichloromethane to remove excess salts and polar byproducts. The filtrate was concentrated in vacuo and the crude residue was purified by flash chromatography on silica gel (12.5% ethyl acetate/hexanes as eluent) to furnish 3-6 (23.9 g) as a viscous pale yellow oil.

Step F: Preparation of Tert-Butyl 4-{2-[(1S)-1-Aminoethyl]-4-Chlorophenyl}Piperidine-1-Carboxylate (3-7)

A mixture of tert-butyl 4-{4-chloro-2-[(1S)-1-(azido)ethyl]phenyl}-3,6-dihydropyridine-1-carboxylate (3-6) (22.9 g, 63.1 mmol) and platinum (IV) oxide (1.08 g, 4.73 mmol) in ethanol/glacial acetic acid (1:1, 200 mL) was hydrogenated at atmospheric pressure for approximately 15 h. The resulting mixture was degassed via three vacuum/hydrogen ingress cycles to remove the liberated nitrogen and the hydrogenation was then continued for a further 24 h. The reaction mixture was filtered through a short column of celite®, eluted copiously with ethanol. The filtrate was evaporated and the residue was partitioned between methylene chloride and 1N sodium hydroxide. The organic layer was separated and the aqueous phase was re-extracted twice with methylene chloride. The combined organic extracts were washed with water, brine, dried (Na$_2$SO$_4$), and concentrated in vacuo to give crude (~70% pure) 3-7 as a colorless foam.

Step G: Preparation of Tert-Butyl 4-{2-[(1S)-1-(Acetylamino)Ethyl]-4-Chlorophenyl}Piperidine-1-Carboxylate (3-8)

Acetyl chloride (1.71 mL, 24.0 mmol) was added to a solution of crude tert-butyl 4-{2-[(1S)-1-aminoethyl]-4-chlorophenyl}piperidine-1-carboxylate (3-7) (5.42 g of ~70% pure material, 11.2 mmol) and triethylamine (6.69 mL, 48.0 mmol) in dichloromethane at approximately 0° C. After 2 h, the reaction mixture was poured into water and extracted three times with ethyl acetate. The combined organic extracts were washed with brine, dried (MgSO$_4$) and concentrated in vacuo. Purification of the crude residue by flash chromatography on silica gel (gradient elution; 35 to 50% ethyl acetate/hexanes as eluent) provided tert-butyl 4-{2-[(1S)-1-(acetylamino)ethyl]-4-chlorophenyl}piperidine-1-carboxylate (3-8) as a pale yellow foam (4.1 g). If desired, traces of the minor R-enantiomer could be removed using preparative chiral high pressure liquid chromatography on CHIRALPAK AD Phase, (7.5% ethano/heptanes as eluent) to give in order of elution: R-enantiomer as a colorless solid followed by the S-enantiomer as a colorless solid.

Step H: Preparation of N-[(1S)-1-(5-Chloro-2-Piperidin-4-Ylphenyl)Ethyl]Acetamide Hydrochloride (3-9)

A saturated solution of hydrogen chloride in ethyl acetate (15 mL) was added to a stirred solution of tert-butyl 4-{2-[(1S)-1-(acetylamino)ethyl]-4-chlorophenyl}piperidine-1-carboxylate (3-8) (3.66 g, 9.61 mmol) in methylene chloride (15 mL) at 0° C. After 3 h, the volatiles were evaporated in vacuo, and the crude residue triturated twice with dry diethyl ether to give 3-9 (3.05 g) as a colorless solid.

Step I: Preparation of N-{(1S)-1-[2-(1-{[(3S,4R)-1-Tert-Butyl-4-(2,4-Difluorophenyl)Pyrrolidin-3-yl]Carbonyl}Piperidin-4-yl)-5-Chlorophenyl]ethyl}Acetamide (3-10)

N,N-diisopropylethylamine (5.86 mL, 33.6 mmol) was added to a stirred suspension of (3S,4R)-1-tert-butyl-4-(2,4-difluorophenyl)pyrrolidine-3-carboxylic acid hydrochloride (3-9) (3.07 g, 9.61 mmol), N-[(1S)-1-(5-chloro-2-piperidin-4-ylphenyl)ethyl]acetamide hydrochloride (3.05 g, 9.61 mmol), and O-(7-azabenzotriazol-1-yl)-1,1,3,3-tetramethyluronium hexafluoro-phosphate (4.38 g, 11.5 mmol) in N,N-dimethylfoimamide (20 mL) at ambient temperature. After approximately 18 h, the reaction mixture was poured water and extracted three times with ethyl acetate. The combined organic extracts were washed with brine, dried (Na$_2$SO$_4$) and concentrated in vacuo. Purification of the residue by flash chromatography on silica gel (gradient elution; 0–9% methanol (containing 10% v/v ammonium hydroxide)/methylene chloride as eluent) provided 3-10 (5.2 g) as a foam m/z (ES) 546 (MH$^+$).

High resolution mass spectrum: calcd. for $C_{30}H_{39}ClF_2N_3O_2$: (MH+): m/z 546.2699; Found: m/z 546.2693.

The hydrochloride salt of 3-10 was prepared as follows: A saturated solution of hydrogen chloride in ethyl acetate (20 mL) was added to a stirred solution of 3-10 (5.20 g, 9.52 mmol) in methylene chloride (20 mL) at 0° C. After 10 min, the volatiles were evaporated in vacuo, and the crude residue was triturated twice with dry diethyl ether to give 3-10 HCl (5.55 g) as a colorless solid.

Following procedures similar to that described above and for Example 1, the following compounds were prepared:

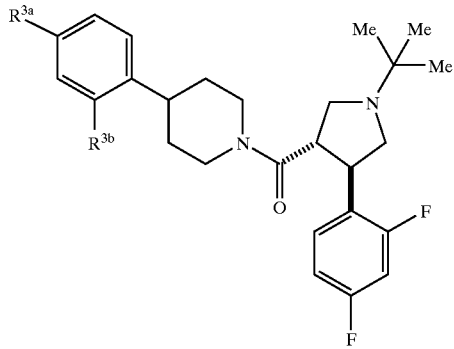

-continued

| Ex. # | R³ᵃ | R³ᵇ | Parent Ion m/z (M + H) |
|---|---|---|---|
| 105 | H | NH₂ | 442 |
| 106 | H | (N-methylacetamide) | 484 |
| 107 | H | (N-methylpropanamide) | 498 |
| 108 | H | (N-methylisobutyramide) | 512 |
| 109 | H | (N-methylpivalamide) | 526 |
| 110 | H | (N-methylcyclohexanecarboxamide) | 552 |
| 111 | H | (N-methyl-3-methylpentanamide) | 540 |
| 112 | H | (N-methylcyclopentanecarboxamide) | 538 |
| 113 | H | (N-methyl-2-methylcyclohexanecarboxamide) | 566 |
| 114 | H | (N-methylnorbornanecarboxamide) | 564 |
| 115 | H | (N-methylbenzamide) | 546 |
| 116 | H | (N-methylmethanesulfonamide) | 520 |
| 117 | H | NH₂ (ethylamine) | 456 |
| 118 | H | (urea derivative) | 541 |
| 119 | H | (urea derivative) | 541 |

| Ex. # | R³ᵃ | R³ᵇ | Parent Ion m/z (M + H) |
|---|---|---|---|
| 120 | H | (ethyl-NH-C(O)-NH-Me urea) | 513 |
| 121 | H | (ethyl-NH-C(O)-N(Me)₂ urea) | 513 |
| 122 | H | (ethyl-NH-C(O)-NH-C(Me)₃ urea) | 555 |
| 123 | H | (ethyl-NH-C(O)-Me acetamide) | 498 |
| 124 | H | (ethyl-NH-C(O)-Et propionamide) | 512 |
| 125 | H | (ethyl-NH-C(O)-CH(Me)₂ isobutyramide) | 526 |
| 126 | H | (ethyl-NH-C(O)-C(Me)₃ pivalamide) | 540 |
| 127 | H | (3-ethyl-4,4-dimethyl-oxazolidin-2-one) | 555 |

| Ex. # | R³ᵃ | R³ᵇ | Parent Ion m/z (M + H) |
|---|---|---|---|
| 128 | H | (3-ethyl-oxazolidin-2-one) | 526 |
| 129 | H | (3-isopropyl-oxazolidin-2-one) | 541 |
| 130 | H | (3-tert-butyl-oxazolidin-2-one) | |
| 131 | H | (3,5-dimethyl-isoxazole-4-sulfonamide, N-Me) | 601 |
| 132 | H | (furazan-3-carboxamide, N-Me) | 538 |
| 133 | H | (1,2,5-thiadiazole-3-carboxamide, N-Me) | 537 |
| 134 | H | (oxazole-4-carboxamide, N-Me) | 554 |

| Ex. # | R3a | R3b | Parent Ion m/z (M + H) |
|---|---|---|---|
| 135 | H | N-methyl oxazole-5-carboxamide | 537 |
| 136 | H | N-methyl 5-methyl-1,3,4-oxadiazole-2-carboxamide | 552 |
| 137 | H | N-methyl isoxazole-4-carboxamide | 537 |
| 138 | H | N-methyl 3-methyl-1H-1,2,4-triazole-5-carboxamide | 551 |
| 139 | H | isopropylamine | 468 |
| 140 | Cl | isopropylamine | 504 |
| 141 | Cl | N-isopropyl acetamide | 546 |
| 142 | F | N-isopropyl acetamide | 530 |

| Ex. # | R3a | R3b | Parent Ion m/z (M + H) |
|---|---|---|---|
| 143 | Cl | N-isopropyl acetamide | 546 |
| 144 | Cl | N-isopropyl acetamide | 546 |
| 145 | Cl | N-isopropyl cyclobutanecarboxamide | 586 |
| 146 | F | N-isopropyl cyclobutanecarboxamide | |
| 147 | Cl | N-isopropyl propionamide | 560 |
| 148 | F | N-isopropyl propionamide | |
| 149 | Cl | N-isopropyl 2-methylpropanamide | 574 |
| 150 | Cl | N-isopropyl pivalamide | 588 |
| 151 | Cl | N-isopropyl-N'-methylurea | 561 |

-continued
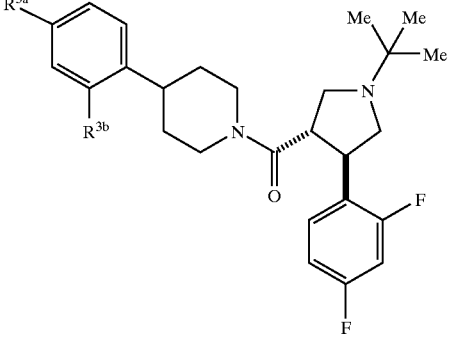
| Ex. # | R3a | R3b | Parent Ion m/z (M + H) |
|---|---|---|---|
| 152 | F | 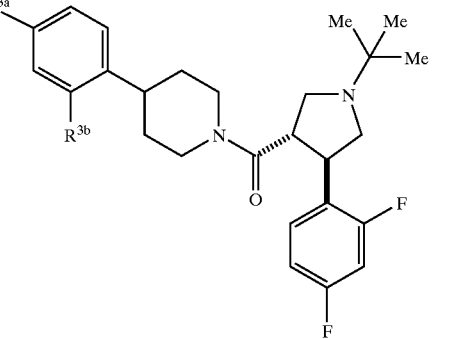 | |
| 153 | Cl | 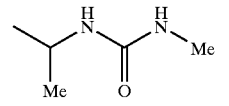 | 603 |
| 154 | Cl | 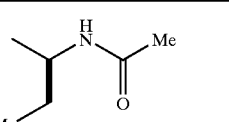 | |
| 155 | F | 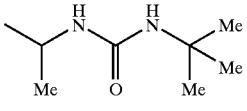 | 544 |
| 156 | H | 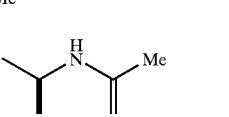 | |
| 157 | H | 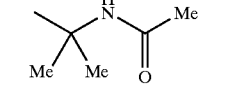 | 512 |
| 158 | Cl | 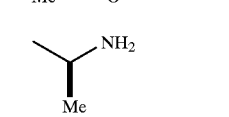 | 544 |
| 159 | Cl | 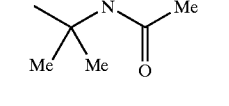 | 544 |
| 160 | F | 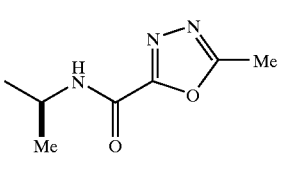 | 544 |
| 161 | CF3 | 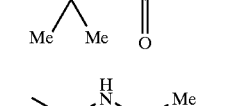 | 580 |
-continued
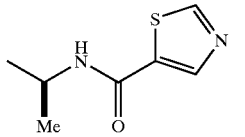
| Ex. # | R3a | R3b | Parent Ion m/z (M + H) |
|---|---|---|---|
| 162 | Cl | 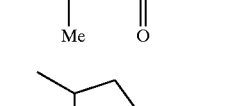 | 560 |
| 163 | Et | 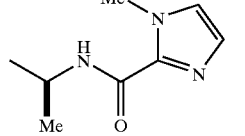 | 540 |
| 164 | Cl | 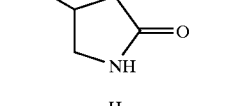 | 504 |
| 165 | Cl | 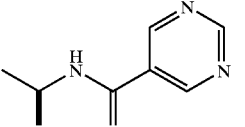 | 614 |
| 166 | Cl | 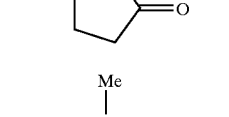 | 615 |
| 167 | Cl | 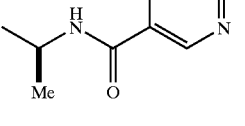 | 612 |
| 168 | Cl | 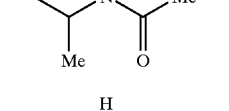 | 610 |
| 169 | Cl | 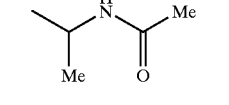 | 574 |

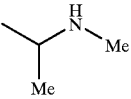

| Ex. # | R³ᵃ | R³ᵇ | Parent Ion m/z (M + H) |
|---|---|---|---|
| 170 | Cl | 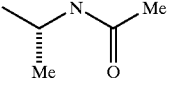 | 610 |
| 171 | Cl | 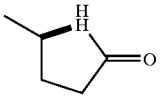 | 544 |
| 172 | Cl | 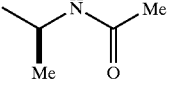 | 544 |
| 173 | Cl | 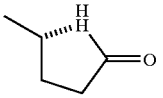 | 546 |
| 174 | Cl | 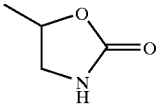 | 558 |
| 175 | Cl | 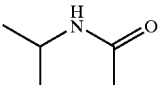 | 544 |
| 176 | Cl | 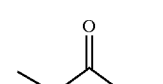 | 544 |
| 177 | Cl | 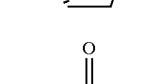 | 546 |
| 178 | Cl | 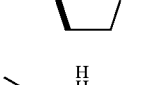 | 546 |

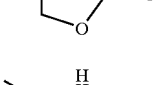

| Ex. # | R³ᵃ | R³ᵇ | Parent Ion m/z (M + H) |
|---|---|---|---|
| 179 | F | 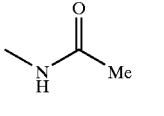 | 530 |
| 180 | F |  | 530 |

EXAMPLES 181–184

Following a procedure similar to that described above for Example 1 but using the corresponding 1-(t-butyl)-3-(2,4-difluorophenyl)-piperidine-4-carboxylic acid intermediate for the peptide coupling reaction with an appropriately substituted 4-phenyl-piperidine intermediate, the following compounds were prepared:

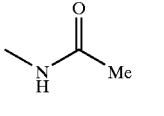

| Ex. # | R³ᵃ | R³ᵇ | Parent Ion m/z (M + H) |
|---|---|---|---|
| 181 | H | COOMe | 499 |
| 182 | H |  | 498 |
| 183 | H | CH₂CH₂CN | |
| 184 | Cl | COOMe | 533 |

EXAMPLE 185

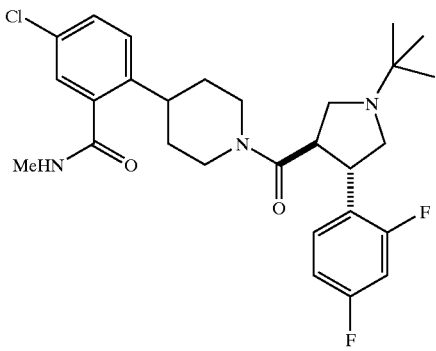

This example was prepared following a procedure similar to that described above for Example 1 but using (3R,4S)-1-tert-butyl-4-(2,4-pyrrolidine-3-carboxylic acid for the peptide coupling reaction; mass spectrum: m/z 518 (M+H).

EXAMPLE 186

Following procedures similar to that decribed above for Example 1, the following compound was also prepared:

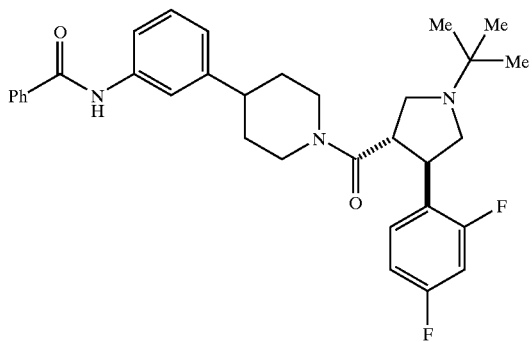

Biological Assays

A. Binding Assay. The membrane binding assay was used to identify competitive inhibitors of $^{125}$I-NDP-alpha-MSH binding to cloned human MCRs expressed in mouse L- or Chinese hamster ovary (CHO)-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BR1); 100 ml 10% heat-inactivated fetal bovine serum (Sigma); 10 mL 10,000 unit/mL penicillin & 10,000 μg/mL streptomycin (Gibco/BR1); 10 ml 200 mM L-glutamine (Gibco/BR1); 1 mg/mL geneticin (G418) (Gibco/BR1). The cells were grown at 37° C. with $CO_2$ and humidity control until the desired cell density and cell number was obtained.

The medium was poured off and 10 mls/monolayer of enzyme-free dissociation media (Specialty Media Inc.) was added. The cells were incubated at 37° C. for 10 min or until cells sloughed off when flask was banged against hand.

The cells were harvested into 200 mL centrifuge tubes and spun at 1000 rpm, 4° C., for 10 min. The supernatant was discarded and the cells were resuspended in 5 mls/monolayer membrane preparation buffer having the composition: 10 mM Tris pH 7.2–7.4; 4 μg/mL Leupeptin (Sigma); 10 μM Phosphoramidon (Boehringer Mannheim); 40 μg/mL Bacitracin (Sigma); 5 μg/mL Aprotinin (Sigma); 10 mM Pefabloc (Boehringer Mannheim). The cells were homogenized with motor-driven dounce (Talboy setting 40), using 10 strokes and the homogenate centrifuged at 6,000 rpm, 4° C., for 15 min.

The pellets were resuspended in 0.2 mls/monolayer membrane prep buffer and aliquots were placed in tubes (500–1000 μL/tube) and quick frozen in liquid nitrogen and then stored at −80° C.

Test compounds or unlabelled NDP-α-MSH was added to 100 μL of membrane binding buffer to a final concentration of 1 μM. The membrane binding buffer had the composition: 50 mM Tris pH 7.2; 2 mM $CaCl_2$; 1 mM $MgCl_2$; 5 mM KCl; 0.2% BSA; 4 μg/mL Leupeptin (SIGMA); 10 μM Phosphoramidon (Boehringer Mannheim); 40 μg/mL Bacitracin (SIGMA); 5 μg/mL Aprotinin (SIGMA); and 10 mM Pefabloc (Boehringer Mannheim). One hundred μL of membrane binding buffer containing 10–40 μg membrane protein was added, followed by 100 μM $^{125}$I-NDP-α-MSH to final concentration of 100 pM. The resulting mixture was vortexed briefly and incubated for 90–120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 mL per well) with room temperature of filter wash having the composition: 50 mM Tris-HCl pH 7.2 and 20 mM NaCl. The filter was dried, and the bottom sealed and 50 μL of Packard Microscint-20 was added to each well. The top was sealed and the radioactivity quantitated in a Packard Topcount Microplate Scintillation counter.

B. Functional assay. Functional cell based assays were developed to discriminate melanocortin receptor agonists from antagonists.

Cells (for example, CHO- or L-cells or other eukaryotic cells) expressing a human melanocortin receptor (see e.g. Yang-YK; Ollmann-MM; Wilson-BD; Dickinson-C; Yamada-T; Barsh-GS; Gantz-I; Mol-Endocrinol. 1997 March; 11(3): 274-80) were dissociated from tissue culture flasks by rinsing with Ca and Mg free phosphate buffered saline (14190-136, Life Technologies, Gaithersburg, Md.) and detached following 5 min incubation at 37° C. with enzyme free dissociation buffer (S-014-B, Specialty Media, Lavellette, N.J.). Cells were collected by centrifugation and resuspended in Earle's Balanced Salt Solution (14015-069, Life Technologies, Gaithersburg, Md.) with additions of 10 mM HEPES pH 7.5, 5 mM $MgCl_2$, 1 mM glutamine and 1 mg/ml bovine serum albumin. Cells were counted and diluted to 1 to 5×10$^6$/mL. The phosphodiesterase inhibitor 3-isobutyl-1-methylxanthine was added to cells to 0.6 mM.

Test compounds were diluted in dimethylsulfoxide (DMSO) ($10^{-5}$ to $10^{-10}$ M) and 0.1 volume of compound solution was added to 0.9 volumes of cell suspension; the final DMSO concentration was 1%. After room temperature incubation for 45 min, cells were lysed by incubation at 100° C. for 5 min to release accumulated cAMP.

cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH which was defined as a 100% agonist. The $EC_{50}$ is defined as the compound concentration which results in half maximal stimulation, when compared to its own maximal level of stimulation.

Antagonist assay: Antagonist activity was defined as the ability of a compound to block cAMP production in response to alpha-MSH. Solution of test compounds and suspension of receptor containing cells were prepared and mixed as described above; the mixture was incubated for 15 min, and an $EC_{50}$ dose (approximately 10 nM alpha-MSH) was added to the cells. The assay was terminated at 45 min and cAMP quantitated as above. Percent inhibition was determined by comparing the amount of cAMP produced in the presence to that produced in the absence of test compound.

C. In Vivo Food Intake Models

1) Overnight food intake. Sprague Dawley rats are injected intracerebroventricularly with a test compound in 400 nL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 h post compound administration is measured.

2) Food intake in diet induced obese mice. Male C57/B16J mice maintained on a high fat diet (60% fat calories) for 6.5 months from 4 weeks of age are are dosed intraperitoneally with test compound. Food intake and body weight are measured over an eight day period. Biochemical parameters relating to obesity, including leptin, insulin, triglyceride, free fatty acid, cholesterol and serum glucose levels are determined.

D. Rat Ex Copula Assay

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests. This conditioning takes ~4 days. Day 1, the animals are placed in a darkened restrainer and left for 15–30 minutes. Day 2, the animals are restrained in a supine position in the restrainer for 15–30 minutes. Day 3, the animals are restrained in the supine position with the penile sheath retracted for 15–30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation animals are given a treat to ensure positive reinforcement.

2) Ex Copula Reflex Tests. Rats are gently restrained in a supine position with their anterior torso placed inside a cylinder of adequate size to allow for normal head and paw grooming. For a 400–500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copula genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and or vehicle evaluations are conducted to determine how and if an animal will respond. Some animals have a long duration until the first response while others are non-responders altogether. During this baseline evaluation latency to first response, number and type of responses are recorded. The testing time frame is 15 minutes after the first response.

After a minimum of 1 day between evaluations, these same animals are administered the test compound at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunction

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna K E et al, *A Model For The Study of Sexual Function In Anesthetized Male And Female Rats*, Am. J. Physiol. (Regulatory Integrative Comp. Physiol 30): R1276-R1285, 1991; McKenna K E et al, *Modulation By Peripheral Serotonin of The Threshold For Sexual Reflexes In Female Rats*, Pharm. Bioch. Behav., 40:151–156, 1991; and Takahashi L K et al, *Dual Estradiol Action In The Diencephalon And The Regulation Of Sociosexual Behavior In Female Golden Hamsters*, Brain Res., 359:194–207, 1985.

Representative compounds of the present invention were tested and found to bind to the melanocortin-4 receptor. These compounds were generally found to have $IC_{50}$ values less than 2 $\mu$M. Representative compounds of the present invention were also tested in the functional assay and found generally to activate the melanocortin-4 receptor with $EC_{50}$ values less than 1 $\mu$M.

EXAMPLES OF A PHARMACEUTICAL COMPOSITION

As a specific embodiment of an oral composition of a composition of the present invention, 5 mg of Example 168 is formulated with sufficient finely divided lactose to provide a total amount of 580 to 590 mg to fill a size O hard gelatin capsule.

As another specific embodiment of an oral composition of a compound of the present invention, 2.5 mg of Example 104 is formulated with sufficient finely divided lactose to provide a total amount of 580 to 590 mg to fill a size O hard gelatin capsule.

As another specific embodiment of an oral composition of a compound of the present invention, 10 mg of Example 88 is formulated with sufficient finely divided lactose to provide a total amount of 580 to 590 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound selected from the group consisting of:

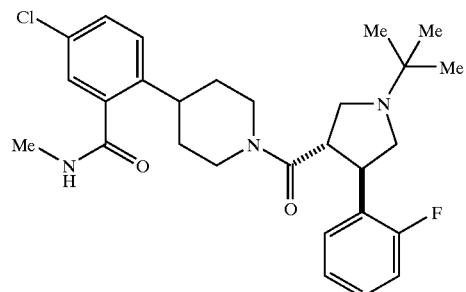

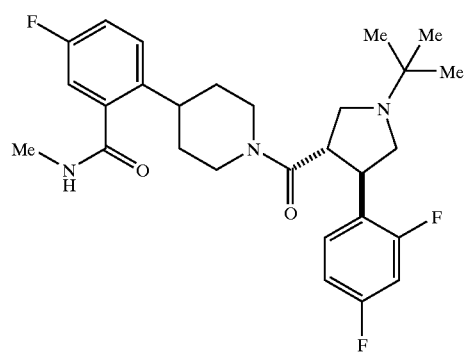

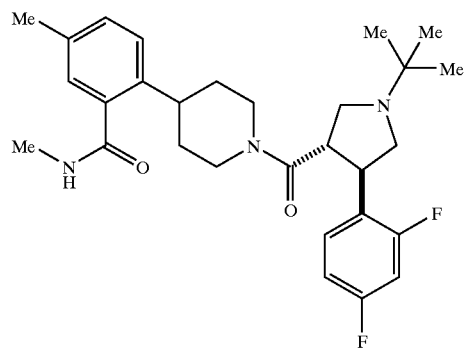

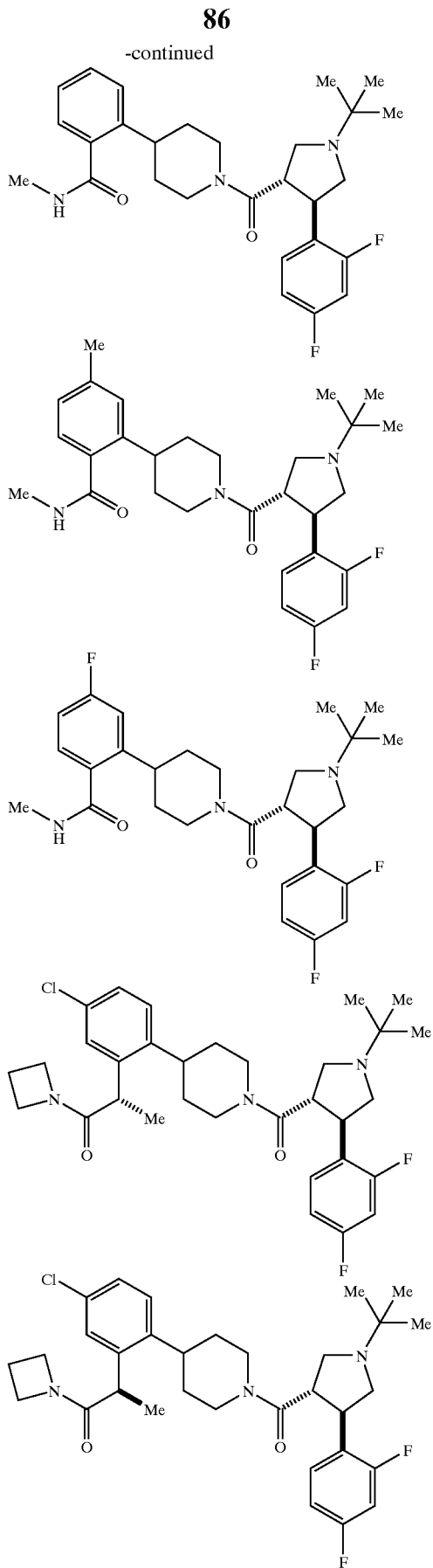

87
-continued
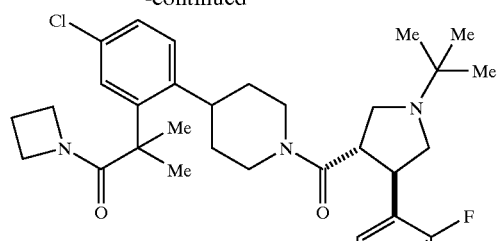
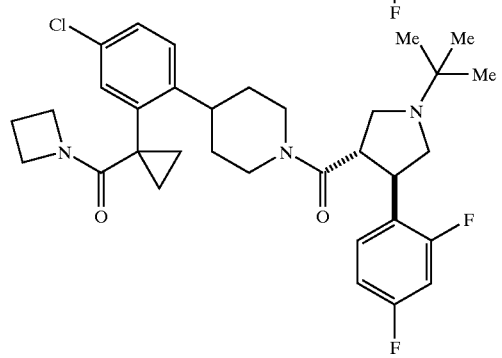
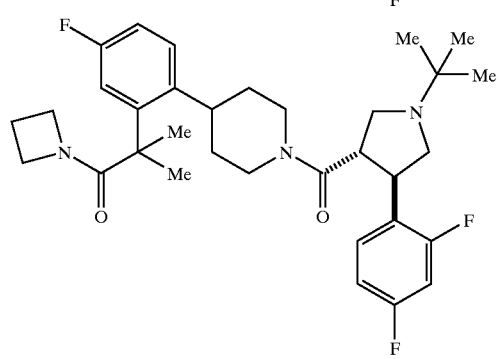
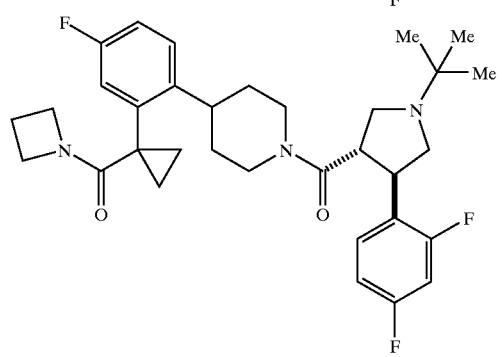
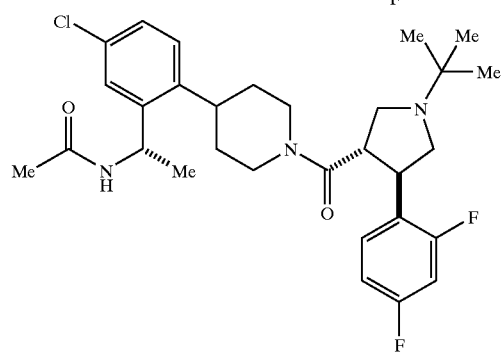
88
-continued
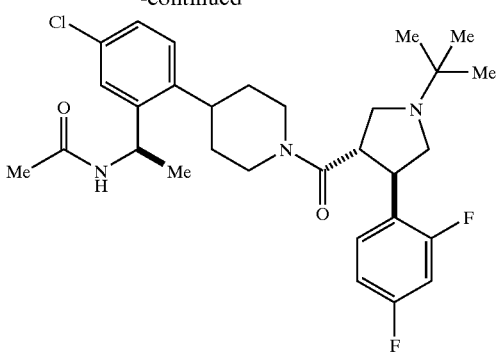
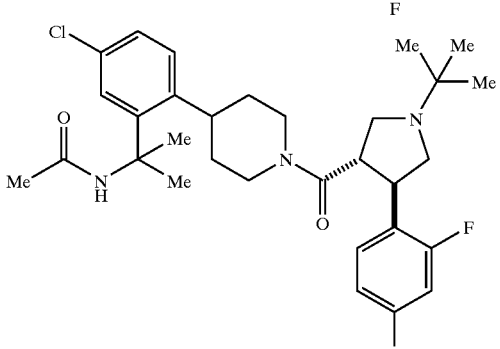
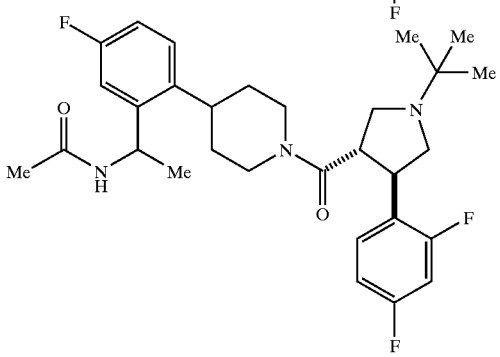
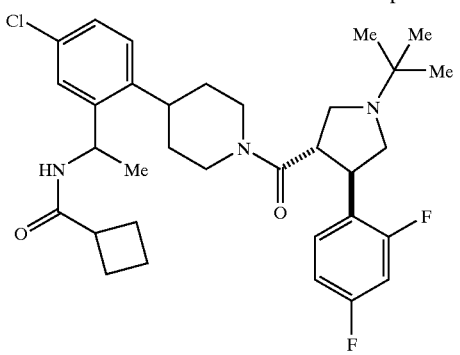
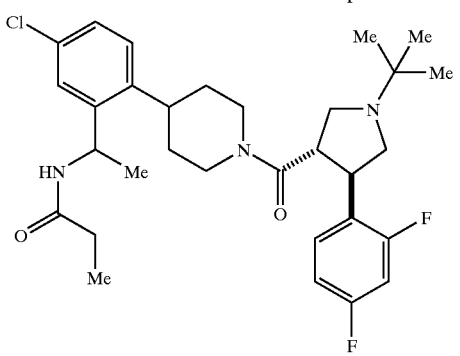

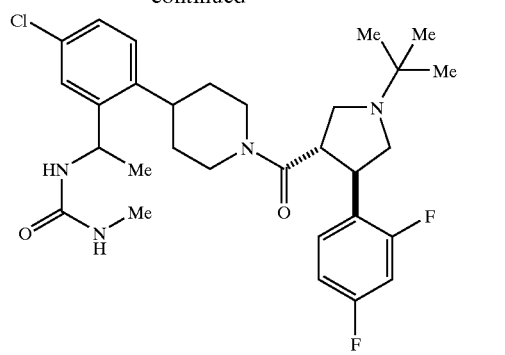
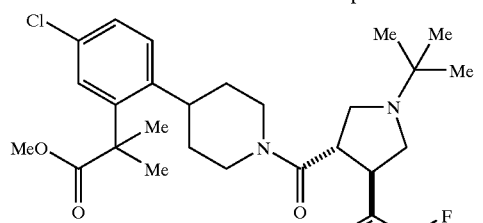
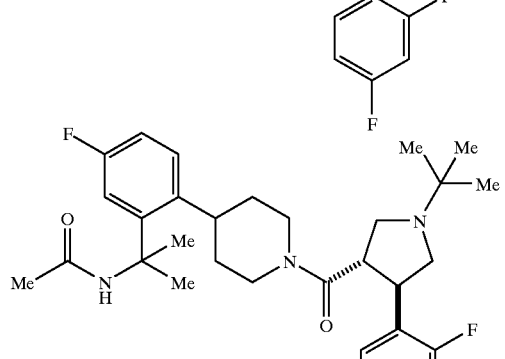
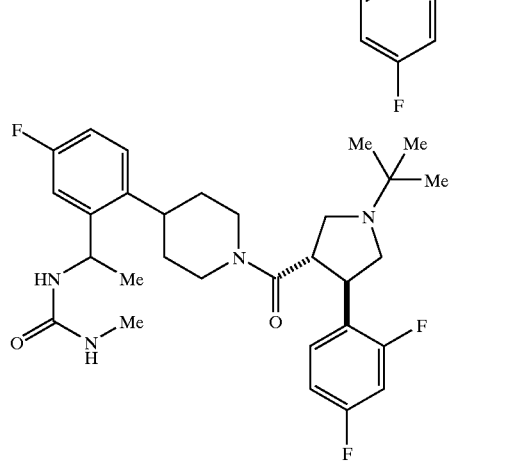
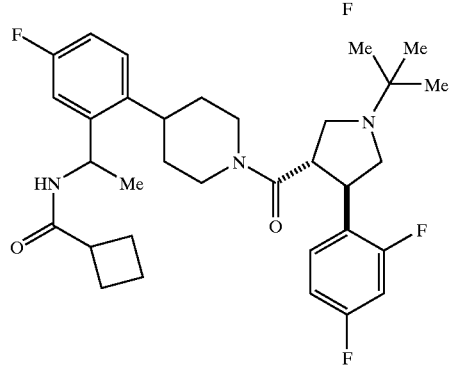
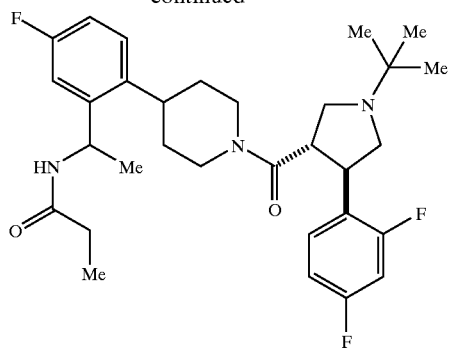
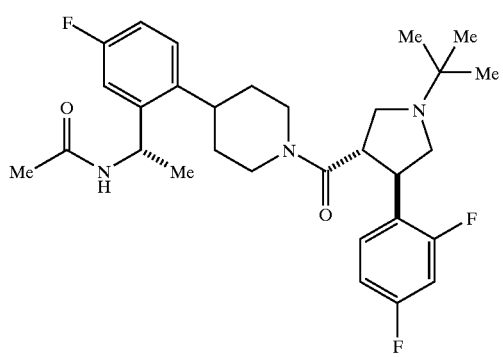
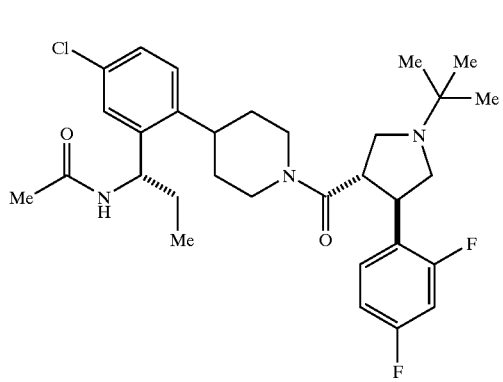
and
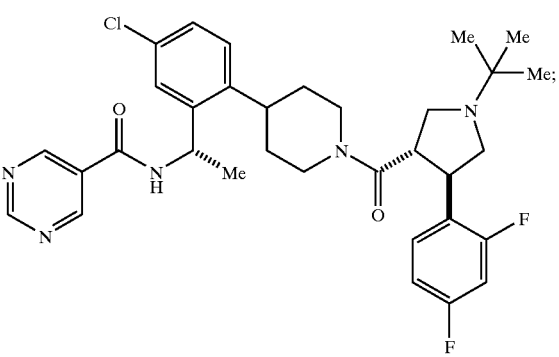
or a pharmaceutically acceptable salt thereof.

2. The compound of claim 1 which is selected from the group consisting of:
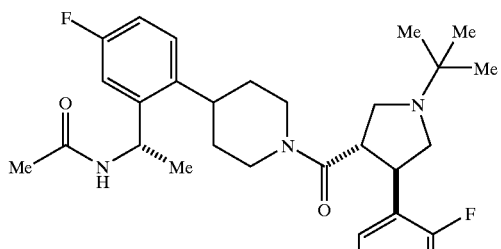
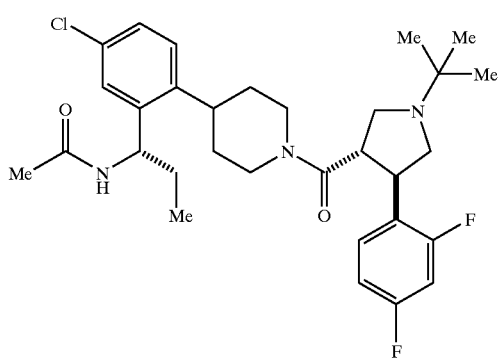
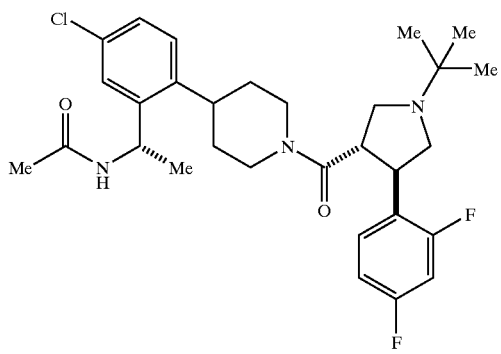
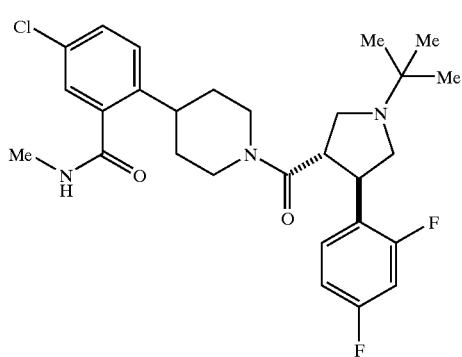
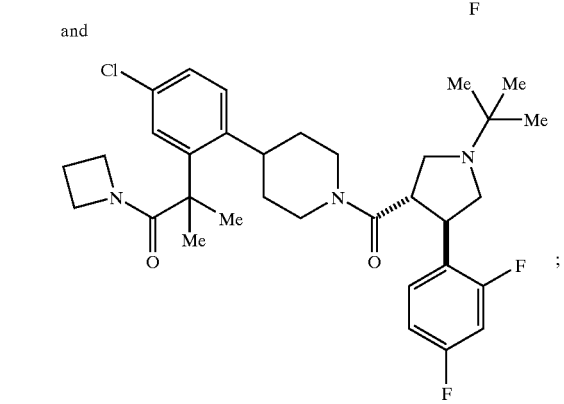
and
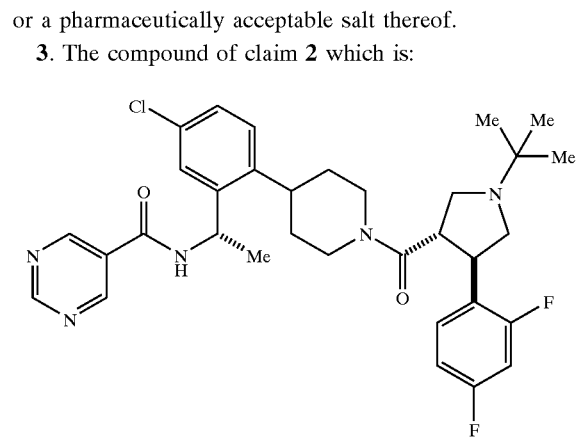
or a pharmaceutically acceptable salt thereof.
3. The compound of claim 2 which is:
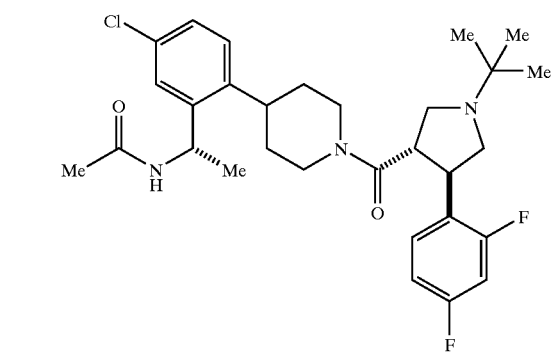
or a pharmaceutically acceptable salt thereof.
4. The compound of claim 2 which is:
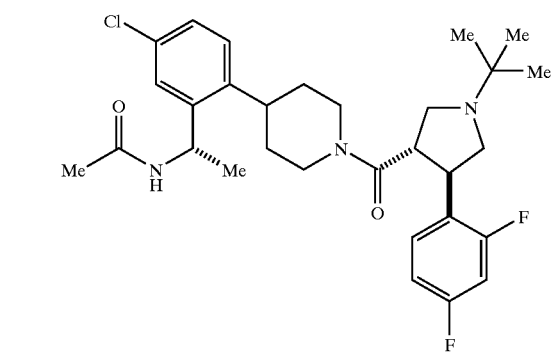
or a pharmaceutically acceptable salt thereof.

5. The compound of claim 2 which is:

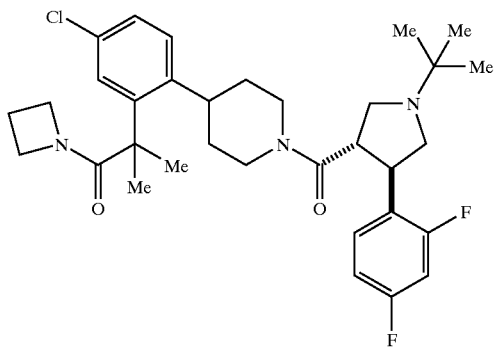

or a pharmaceutically acceptable salt thereof.

6. The compound of claim 1 wherein the pharmaceutically acceptable salt thereof is the hydrochloride salt.

7. The compound of claim 3 wherein the pharmaceutically acceptable salt thereof is the hydrochloride salt.

8. The compound of claim 4 wherein the pharmaceutically acceptable salt thereof is the hydrochloride salt.

9. The compound of claim 5 wherein the pharmaceutically acceptable salt thereof is the hydrochloride salt.

10. A compound selected from the group consisting of:

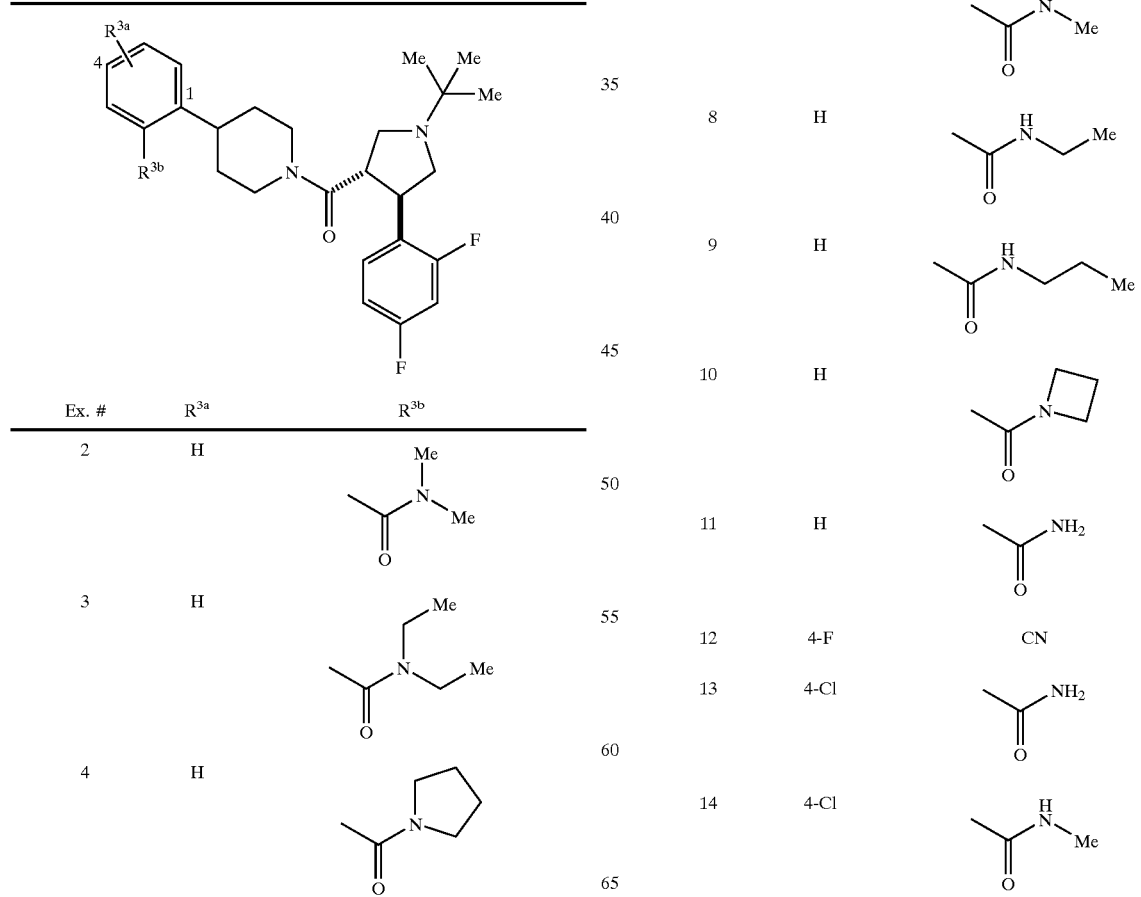

-continued

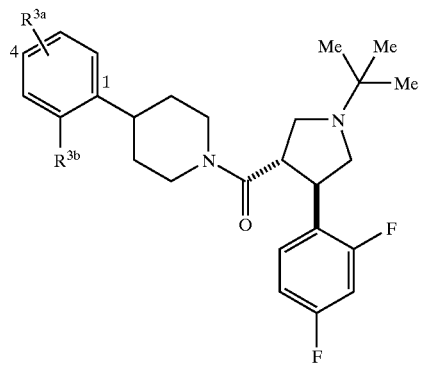

| Ex. # | R³ᵃ | R³ᵇ |
|---|---|---|
| 15 | H | propanoate-O-Me |
| 16 | H | propanamide-NHMe |
| 17 | H | propanamide-NMe₂ |
| 18 | H | propanamide-NHEt |
| 19 | H | propanamide-NH-iPr |
| 20 | H | propanamide-NH-cyclobutyl |
| 21 | H | propanoyl-azetidine |
| 22 | H | propanamide-NH-tBu |
| 23 | H | propanamide-N(Me)(Et) |

-continued

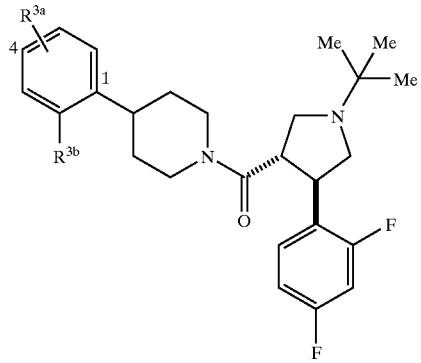

| Ex. # | R³ᵃ | R³ᵇ |
|---|---|---|
| 24 | H | propanamide-N(Me)CH(Me)₂ |
| 25 | H | propanamide-NEt₂ |
| 26 | H | propanoyl-pyrrolidine |
| 27 | 4-Cl | propanamide-NHEt |
| 28 | 4-Cl | propanamide-NH-nPr |
| 29 | 4-Cl | propanamide-NH-iPr |
| 30 | 4-Cl | propanamide-NH-tBu |
| 31 | 4-Cl | propanamide-NH-cyclopropyl |
| 32 | 4-Cl | propanamide-NH-cyclobutyl |

-continued
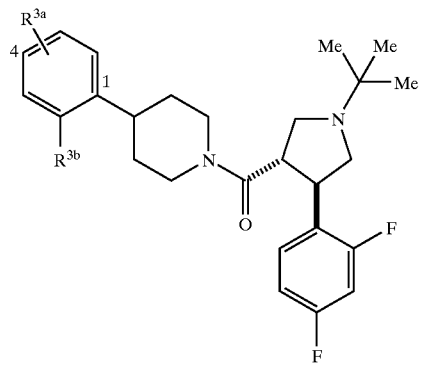
| Ex. # | R³ᵃ | R³ᵇ |
|---|---|---|
| 33 | 4-Cl | 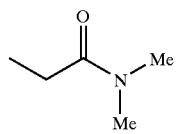 |
| 34 | 4-Cl | 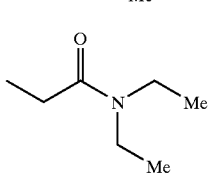 |
| 35 | 4-Cl | 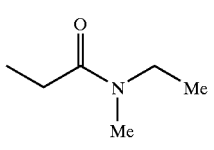 |
| 36 | 4-Cl | 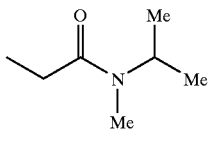 |
| 37 | 4-Cl | 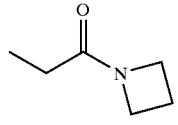 |
| 38 | 4-Cl | 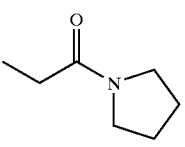 |
| 39 | 4-Cl | 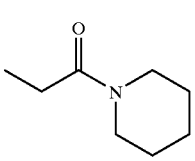 |
| 40 | 4-Cl | 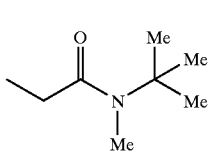 |
-continued
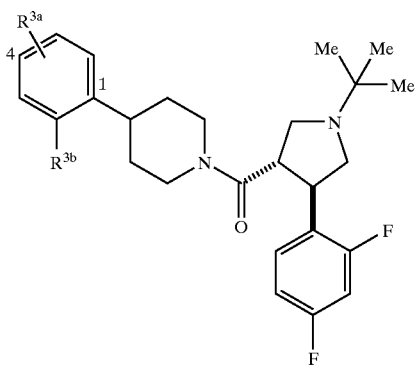
| Ex. # | R³ᵃ | R³ᵇ |
|---|---|---|
| 41 | 4-Cl | 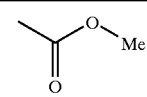 |
| 42 | 4-Cl | 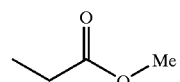 |
| 43 | H | 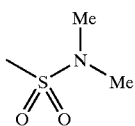 |
| 44 | 5-F | 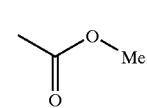 |
| 45 | 3-CH₃ | 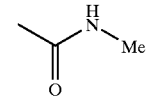 |
| 46 | 3-CH₃ | 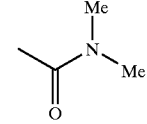 |
| 47 | 3-CH₃ | 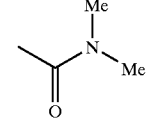 |
| 48 | 4-CH₃ | 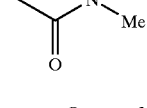 |
| 49 | 4-CH₃ | 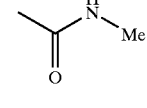 |
| 50 | 4-Cl | 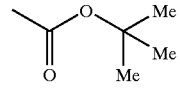 |

-continued
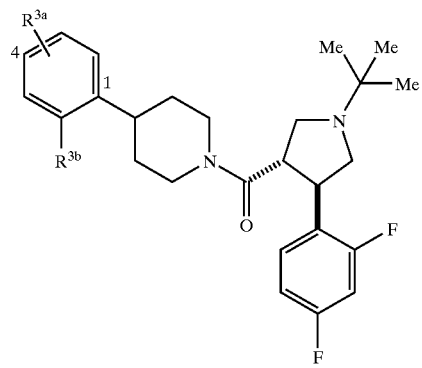
| Ex. # | R³ᵃ | R³ᵇ |
|---|---|---|
| 51 | 5-Me | 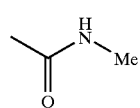 |
| 52 | 4-F | 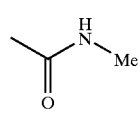 |
| 53 | 4-Cl | 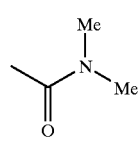 |
| 54 | 4-Cl | 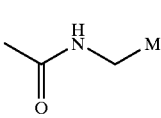 |
| 55 | 4-Cl | 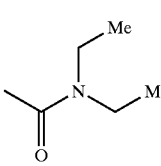 |
| 56 | 4-Cl | 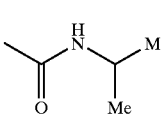 |
| 57 | 4-Cl | 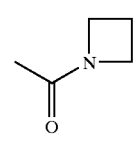 |
| 58 | 4-Cl | 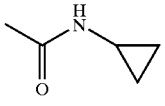 |
| 59 | 4,5-di-F | 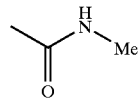 |
-continued
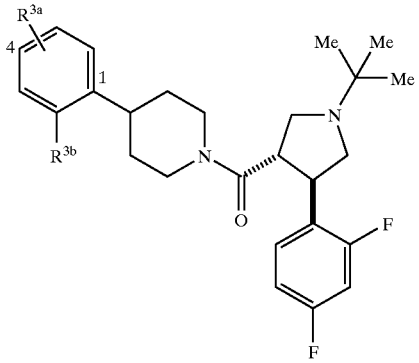
| Ex. # | R³ᵃ | R³ᵇ |
|---|---|---|
| 60 | 4-F | 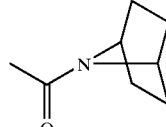 |
| 61 | 4-CF₃ | 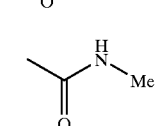 |
| 62 | | 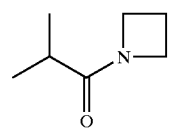 |
or a pharmaceutically acceptable salt thereof.
11. A compound selected from the group consisting of:
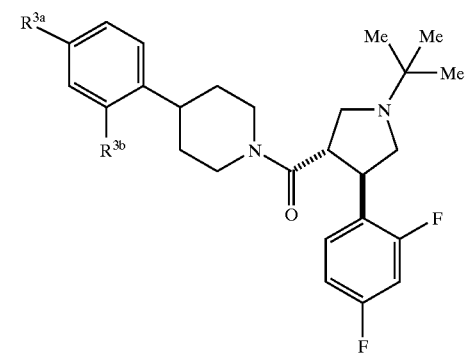
| Ex. # | R³ᵃ | R³ᵇ |
|---|---|---|
| 63 | Cl | 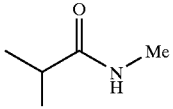 |
| 64 | F | 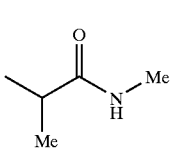 |

-continued
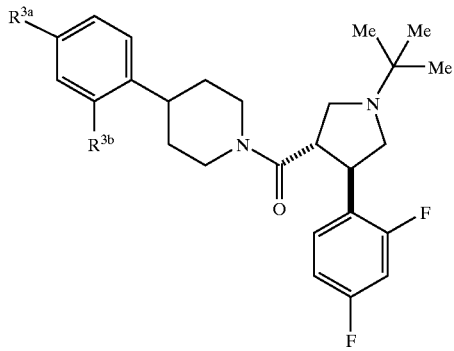
| Ex. # | R³ᵃ | R³ᵇ |
|---|---|---|
| 65 | Cl | 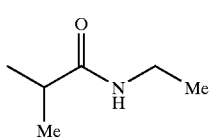 |
| 66 | Cl | 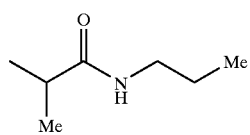 |
| 67 | Cl | 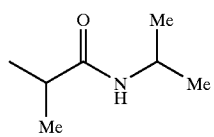 |
| 68 | Cl | 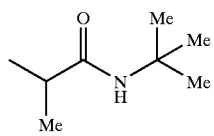 |
| 69 | Cl | 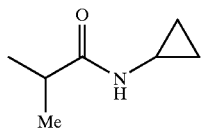 |
| 70 | Cl | 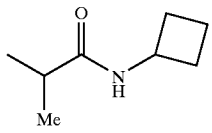 |
| 71 | Cl | 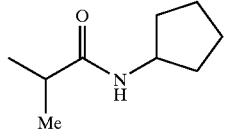 |
| 72 | Cl | 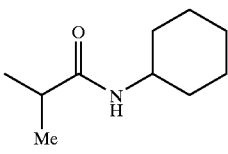 |
-continued
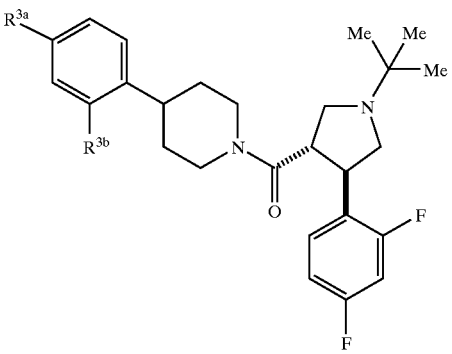
| Ex. # | R³ᵃ | R³ᵇ |
|---|---|---|
| 73 | Cl | 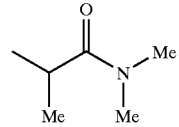 |
| 74 | Cl | 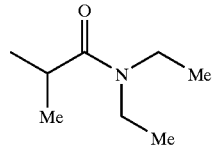 |
| 75 | Cl | 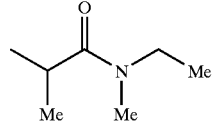 |
| 76 | Cl | 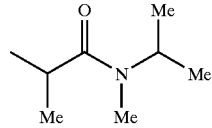 |
| 77 | Cl | 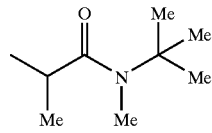 |
| 78 | Cl | 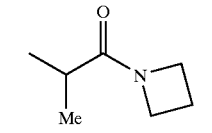 |
| 79 | Cl | 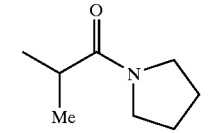 |
| 80 | Cl | 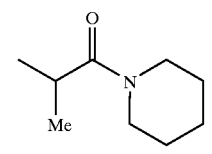 |

-continued
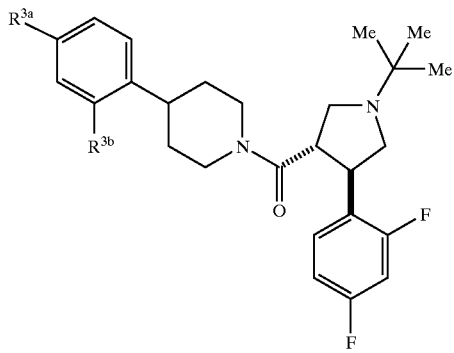
| Ex. # | R³ᵃ | R³ᵇ |
|---|---|---|
| 81 | Cl | 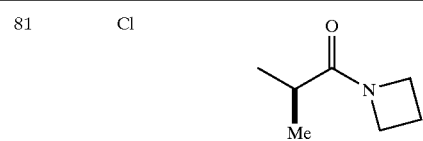 |
| 82 | Cl | 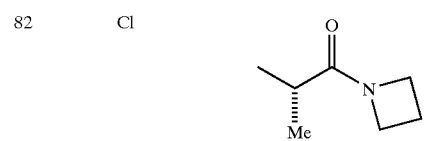 |
| 83 | Cl | 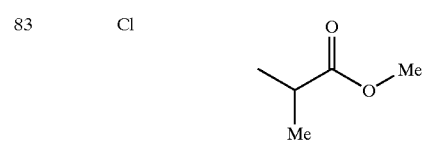 |
| 84 | Cl | 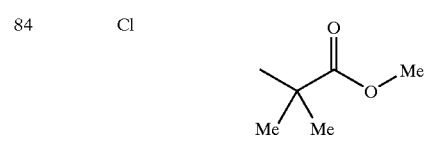 |
| 85 | H | 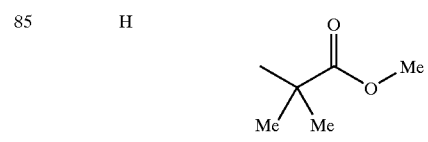 |
| 86 | Cl | 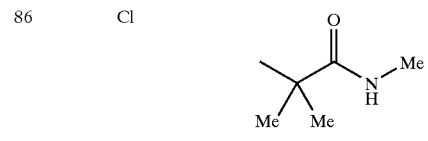 |
| 87 | H | 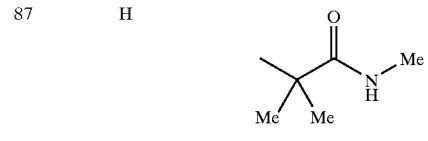 |
| 88 | Cl | 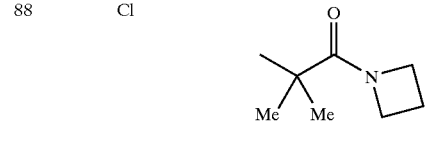 |
-continued
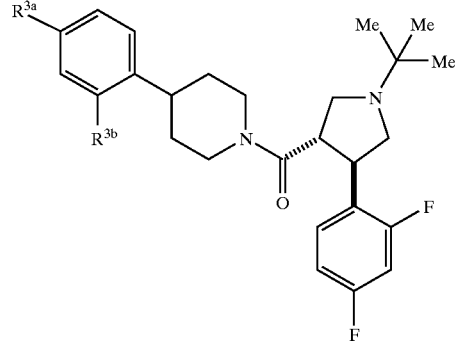
| Ex. # | R³ᵃ | R³ᵇ |
|---|---|---|
| 89 | F | 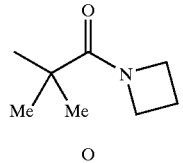 |
| 90 | H | 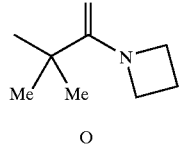 |
| 91 | Cl | 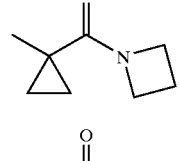 |
| 92 | F | 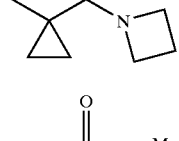 |
| 93 | Cl | 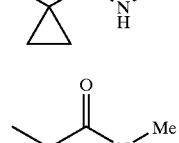 |
| 94 | Cl | 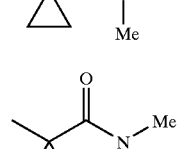 |
| 95 | F | 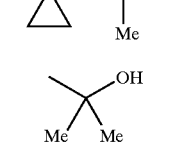 |
| 96 | Cl | 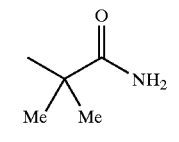 |
| 97 | Cl | 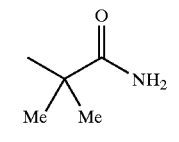 |

-continued

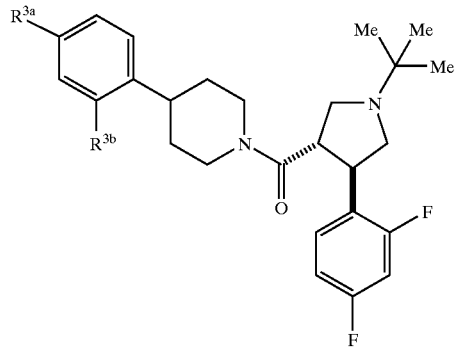

| Ex. # | R³ᵃ | R³ᵇ |
|---|---|---|
| 98 | 5-F | (2-methyl-N-methylpropanamide, Me₂C(Me)C(O)NHMe) |
| 99 | F | (N-(2-hydroxyethyl)-N,2,2-trimethylpropanamide) |
| 100 | F | (1-morpholino-2,2-dimethylpropan-1-one) |
| 101 | Cl | (2,2-dimethylpropanehydrazide) |
| 102 | Cl | (N'-isopropyl-2,2-dimethylpropanehydrazide) |
| 103 | Cl | (N'-acetyl-2,2-dimethylpropanehydrazide) |
| 104 | Cl | ((S)-N-(1-methylethyl)acetamide) |
| 105 | H | NH₂ |
| 106 | H | (N-methylacetamide) |

-continued

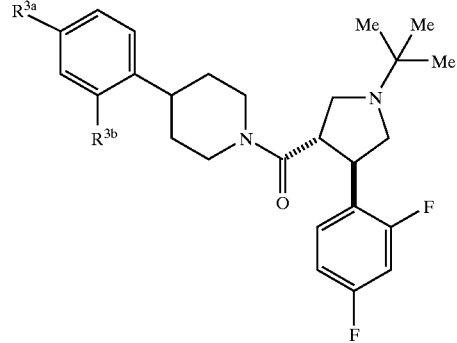

| Ex. # | R³ᵃ | R³ᵇ |
|---|---|---|
| 107 | H | (N-methylpropanamide) |
| 108 | H | (N,2-dimethylpropanamide) |
| 109 | H | (N,2,2-trimethylpropanamide) |
| 110 | H | (N-methylcyclohexanecarboxamide) |
| 111 | H | (2-ethyl-N-methylbutanamide) |
| 112 | H | (N-methylcyclopentanecarboxamide) |
| 113 | H | (N,2-dimethylcyclohexanecarboxamide) |
| 114 | H | (N-methylbicyclo[2.2.1]heptane-2-carboxamide) |

-continued

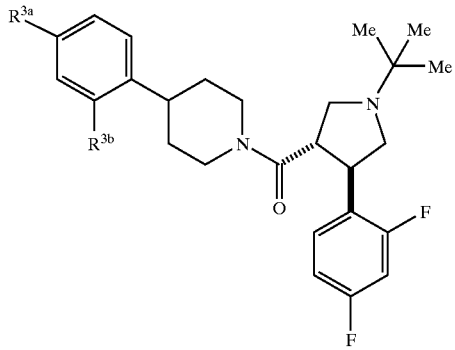

| Ex. # | R³ᵃ | R³ᵇ |
|---|---|---|
| 115 | H | N-methylbenzamide |
| 116 | H | N-methyl methanesulfonamide |
| 117 | H | ethylamine |
| 118 | H | 1-ethyl-3,3-diethylurea |
| 119 | H | 1-ethyl-3-isopropyl-3-methylurea |
| 120 | H | 1-ethyl-3-methylurea |
| 121 | H | 1-ethyl-3,3-dimethylurea |
| 122 | H | 1-ethyl-3-tert-butylurea |
| 123 | H | N-ethylacetamide |

-continued

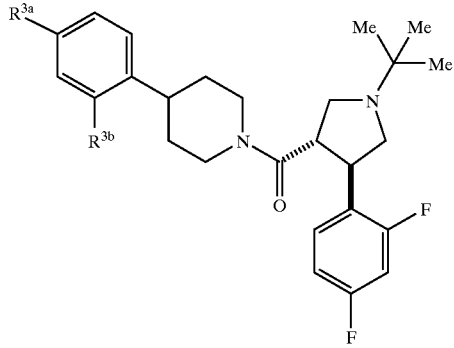

| Ex. # | R³ᵃ | R³ᵇ |
|---|---|---|
| 124 | H | N-ethylpropanamide |
| 125 | H | N-ethylisobutyramide |
| 126 | H | N-ethylpivalamide |
| 127 | H | 3-ethyl-4,4-dimethyloxazolidin-2-one |
| 128 | H | 3-ethyloxazolidin-2-one |
| 129 | H | 3-isopropyloxazolidin-2-one |
| 130 | H | 3-tert-butyloxazolidin-2-one |
| 131 | H | N,3,5-trimethylisoxazole-4-sulfonamide |

-continued

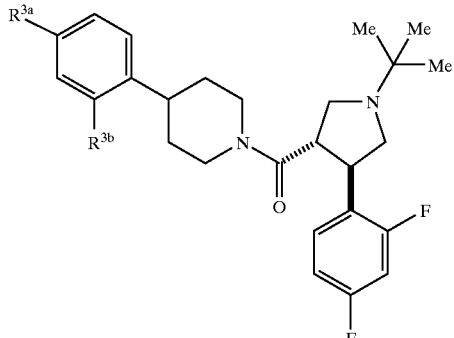

| Ex. # | R3a | R3b |
|---|---|---|
| 132 | H | N-methylcarboxamide-furazan |
| 133 | H | N-methylcarboxamide-thiadiazole |
| 134 | H | N-methylcarboxamide-oxazole |
| 135 | H | N-methylcarboxamide-oxazole (isomer) |
| 136 | H | N-methylcarboxamide-5-methyl-oxadiazole |
| 137 | H | N-methylcarboxamide-isoxazole |
| 138 | H | N-methylcarboxamide-3-methyl-triazole |
| 139 | H | CH(Me)NH₂ |

-continued

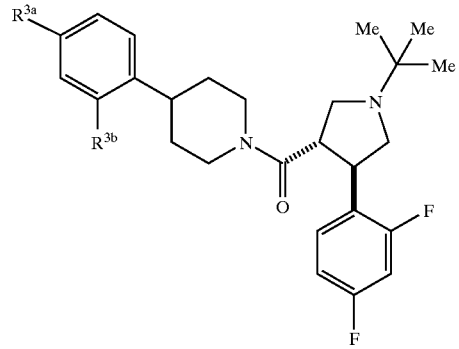

| Ex. # | R3a | R3b |
|---|---|---|
| 140 | Cl | CH(Me)NH₂ |
| 141 | Cl | CH(Me)NHC(O)Me |
| 142 | F | CH(Me)NHC(O)Me |
| 143 | Cl | CH(Me)NHC(O)Me |
| 144 | Cl | CH(Me)NHC(O)Me |
| 145 | Cl | CH(Me)NHC(O)-cyclobutyl |
| 146 | F | CH(Me)NHC(O)-cyclobutyl |
| 147 | Cl | CH(Me)NHC(O)Et |
| 148 | F | CH(Me)NHC(O)Et |
| 149 | Cl | CH(Me)NHC(O)CH(Me)₂ |

-continued
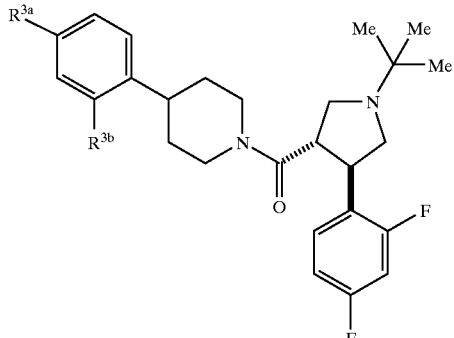
| Ex. # | R³ᵃ | R³ᵇ |
|---|---|---|
| 150 | Cl | 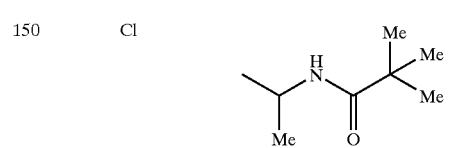 |
| 151 | Cl | 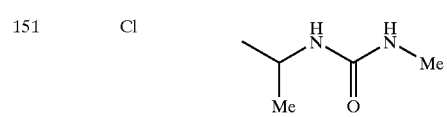 |
| 152 | F | 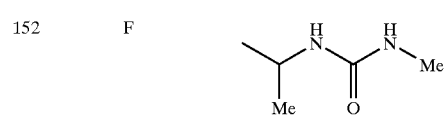 |
| 153 | Cl | 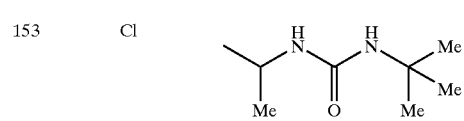 |
| 154 | Cl | 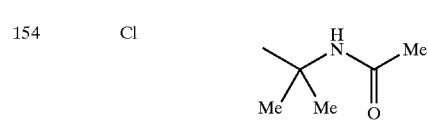 |
| 155 | F | 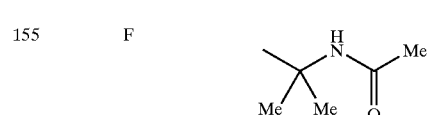 |
| 156 | H | 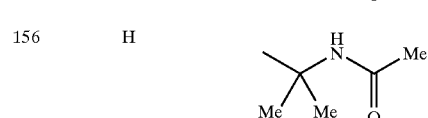 |
| 157 | H |  |
| 158 | Cl | 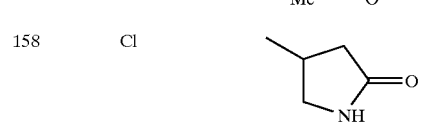 |
| 159 | Cl |  |
-continued
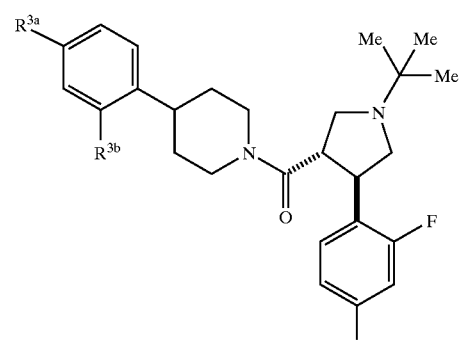
| Ex. # | R³ᵃ | R³ᵇ |
|---|---|---|
| 160 | F | 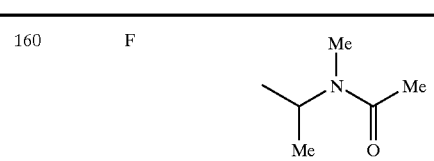 |
| 161 | CF₃ |  |
| 162 | Cl |  |
| 163 | Et | 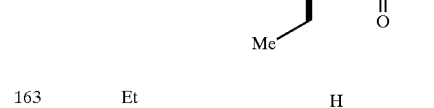 |
| 164 | Cl |  |
| 165 | Cl | 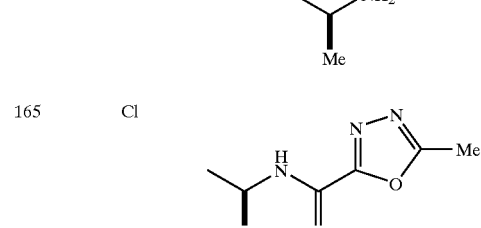 |
| 166 | Cl | 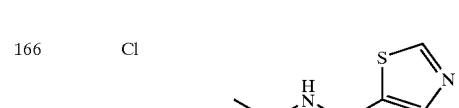 |
| 167 | Cl | 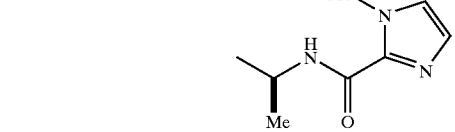 |

-continued

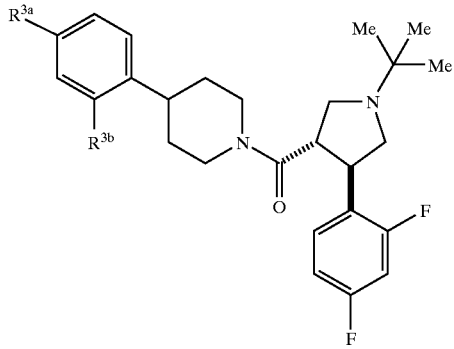

| Ex. # | R³ᵃ | R³ᵇ |
|---|---|---|
| 168 | Cl | 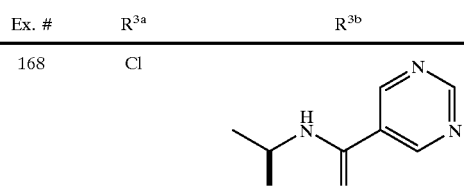 |
| 169 | Cl |  |
| 170 | Cl |  |
| 171 | Cl |  |
| 172 | Cl |  |
| 173 | Cl |  |
| 174 | Cl |  |
| 175 | Cl |  |
| 176 | Cl |  |

-continued

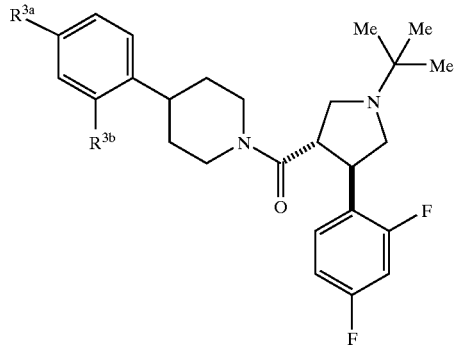

| Ex. # | R³ᵃ | R³ᵇ |
|---|---|---|
| 177 | Cl | |
| 178 | Cl | |
| 179 | F | |
| 180 | F | |
| 181 | H | COOMe |
| 182 | H | |
| 183 | H | CH₂CH₂CN |
| 184 | Cl | COOMe |
| 185 | Cl | | or a pharmaceutically acceptable salt thereof.

12. A method for the treatment of obesity in a mammal in need thereof which comprises administering to the mammal a therapeutically effective amount of a compound according to claim 1.

13. A pharmaceutical composition which comprises a therapeutically effective amount of a compound of claim 1 and a pharmaceutically acceptable carrier.

* * * * *